United States Patent
Adams et al.

(10) Patent No.: US 7,629,462 B2
(45) Date of Patent: Dec. 8, 2009

(54) TETRASUBSTITUTED PYRIMIDINE COMPOUNDS AS CHEMICAL INTERMEDIATES

(75) Inventors: Jerry L. Adams, Wayne, PA (US); Jeffrey C. Boehm, King of Prussia, PA (US); John J. Taggart, Elkins Park, PA (US); Ralph F. Hall, Villanova, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 127 days.

(21) Appl. No.: 11/613,598

(22) Filed: Dec. 20, 2006

(65) Prior Publication Data

US 2007/0167467 A1 Jul. 19, 2007

Related U.S. Application Data

(63) Continuation of application No. 10/220,103, filed as application No. PCT/US01/06688 on Mar. 2, 2001, now Pat. No. 7,235,551.

(60) Provisional application No. 60/186,419, filed on Mar. 2, 2000.

(51) Int. Cl.
C07D 239/47 (2006.01)
(52) U.S. Cl. ..................... 544/317; 514/274
(58) Field of Classification Search ............... 544/317; 514/274
See application file for complete search history.

(56) References Cited

U.S. PATENT DOCUMENTS

| | | | |
|---|---|---|---|
| 3,843,663 A | 10/1974 | Williams et al. |
| 4,560,691 A | 12/1985 | Lesher et al. |
| 4,886,807 A | 12/1989 | Kitamura et al. |
| 4,897,395 A | 1/1990 | Duch et al. |
| 5,304,560 A | 4/1994 | Shimazaki et al. |
| 5,409,930 A | 4/1995 | Spada et al. |
| 5,426,110 A | 6/1995 | Gossett et al. |
| 5,466,692 A | 11/1995 | Ellingboe |
| 5,547,954 A | 8/1996 | Henrie, II et al. |
| 5,597,776 A | 1/1997 | Bratz et al. |
| 5,620,981 A | 4/1997 | Blankley et al. |
| 5,733,913 A | 3/1998 | Blankley et al. |
| 5,733,914 A | 3/1998 | Blankley et al. |
| 5,760,220 A | 6/1998 | Giguere et al. |
| 5,767,097 A | 6/1998 | Tam |
| 5,817,670 A | 10/1998 | Takayama et al. |
| 5,945,422 A | 8/1999 | Doherty et al. |
| 6,083,948 A | 7/2000 | Wilde |
| 6,200,977 B1 | 3/2001 | Cusing et al. |
| 6,277,989 B1 | 8/2001 | Chakravarty et al. |
| 6,476,031 B1 | 11/2002 | Chakravarty et al. |
| 6,479,463 B1 | 11/2002 | Wang et al. |
| 6,492,520 B1 | 12/2002 | Chen |
| 6,498,163 B1 | 12/2002 | Boschelli et al. |
| 6,528,508 B2 | 3/2003 | Salituro et al. |
| 6,528,513 B2 | 3/2003 | Cusing et al. |
| 6,593,333 B1 | 7/2003 | Cumming |
| 6,800,626 B2 | 10/2004 | Salituro et al. |
| 6,809,199 B2 | 10/2004 | Doherty et al. |
| 6,838,559 B2 | 1/2005 | Vaccaro et al. |
| 6,875,769 B2 | 4/2005 | Chen |
| 2003/0114671 A1 | 6/2003 | Chen |
| 2004/0009993 A1 | 1/2004 | Angiolini |
| 2004/0063658 A1 | 4/2004 | Roberts et al. |
| 2004/0116697 A1 | 6/2004 | Adams et al. |
| 2004/0142945 A1 | 7/2004 | Barbosa et al. |
| 2004/0209901 A1 | 10/2004 | Adams et al. |
| 2004/0224958 A1 | 11/2004 | Booth et al. |
| 2004/0235847 A1 | 11/2004 | Quan et al. |
| 2004/0236084 A1 | 11/2004 | Biwersi et al. |
| 2004/0242604 A1 | 12/2004 | Bhattacharya et al. |
| 2005/0187217 A1 | 8/2005 | Wilson et al. |
| 2005/0203109 A1 | 9/2005 | Adams et al. |
| 2005/0272728 A1 | 12/2005 | Altenbach et al. |
| 2006/0217401 A1 | 9/2006 | Boehm et al. |
| 2006/0235029 A1 | 10/2006 | Boehm et al. |
| 2006/0258687 A1 | 11/2006 | Boehm et al. |

FOREIGN PATENT DOCUMENTS

| | | |
|---|---|---|
| EP | 0 278 686 | 2/1988 |
| EP | 0 530 994 | 3/1993 |
| GB | 2 123 830 | 2/1984 |
| JP | 1-261306 | 10/1989 |
| JP | 20000038350 | 2/2000 |
| JP | 2003/127542 | 5/2003 |
| JP | 2004-203751 | 7/2004 |
| WO | WO 92/12154 | 7/1992 |
| WO | WO 94/19350 | 9/1994 |
| WO | WO 95/15952 | 6/1995 |
| WO | WO 95/19774 | 7/1995 |
| WO | WO 95/33750 | 12/1995 |
| WO | WO 97/38992 | 10/1997 |
| WO | WO 98/05661 | 2/1998 |
| WO | WO 98/08846 | 3/1998 |
| WO | WO 98/27098 | 6/1998 |
| WO | WO 98/33798 | 8/1998 |
| WO | 99/32121 | 7/1999 |
| WO | WO 99/41253 | 8/1999 |
| WO | WO 99/61444 | 12/1999 |
| WO | WO 99/64400 | 12/1999 |
| WO | WO 00/23444 | 4/2000 |
| WO | WO 00/43374 | 7/2000 |

(Continued)

OTHER PUBLICATIONS

El-Reedy et al., CAPLUS Abstract 112:35791, 1990.*

(Continued)

*Primary Examiner*—Deepak Rao
(74) *Attorney, Agent, or Firm*—Dara L. Dinner; Charles M. Kinzig; Theodore R. Furman

(57) ABSTRACT

Novel substituted pyrimido[4,5-d]pyrimidin-2-one compounds and compositions for use in therapy as CSBP/p38 kinase inhibitors.

16 Claims, 4 Drawing Sheets

FOREIGN PATENT DOCUMENTS

| | | |
|---|---|---|
| WO | WO 01/19828 | 3/2001 |
| WO | WO 01/42243 | 6/2001 |
| WO | WO 01/55147 | 8/2001 |
| WO | WO 01/70741 | 9/2001 |
| WO | WO 02/058695 | 8/2002 |
| WO | WO 02/059083 | 8/2002 |
| WO | WO02/060869 | 8/2002 |
| WO | WO 02/102315 | 12/2002 |
| WO | WO 2005/014558 | 2/2005 |

OTHER PUBLICATIONS

Ram Vishnu J., CAPLUS Abstract 112:77090, 1990.*
Ram Vishnu J., CAPLUS Abstract 113:78321, 1990.*
Ram Vishnu Ji, CAPLUS Abstract 113;97564, 1990.*
Ram Vishnu J., CAPLUS Abstract 114:42726, 1991.*
Ram et al., CAPLUS Abstract 115:256109, 1991.*
Manhi et al., CAPLUS Abstract 121:83254, 1994.*
Upadhyay et al., CAPLUS Abstract 131:18977, 1999.*
El-Assiery et al., CAPLUS Abstract 132:151761, 1999.*
Agarwal et al., Suitably functionalised pyrimidines as potential antimycotic agents, Bioorganic & Medicinal Chemistry Letters, 10(8), 703-706, Apr. 2000.*
U.S. Appl. No. 11/613,517, filed Dec. 20, 2006, Adams, et al.
U.S. Appl. No. 11/871,039, filed Oct. 11, 2007, Adams, et al.
U.S. Appl. No. 11/839,830, filed Aug. 16, 2007, Adams, et al.
U.S. Appl. No. 11/839,833, filed Aug. 16, 2007, Adams, et al.
U.S. Appl. No. 11/839,834, filed Aug. 16, 2007, Adams, et al.
U.S. Appl. No. 11/908,340, filed Sep. 11, 2007, Boehm, et al.
U.S. Appl. No. 11/908,435, filed Sep. 12, 2007, Callahan, et al.
U.S. Appl. No. 11/908,440, filed Sep. 12, 2007, Callahan, et al.
U.S. Appl. No. 11/908,839, filed Sep. 17, 2007, Callahan, et al.
Adams et al., Progress in Medicinal Chemistry, vol. 38, pp. 2-61 (2001).
Armarcgo, W., Chem. Soc., Quinazolines, Part IV (JCS OA9) p. 561 (1962).
Boehm et al., J. Med. Chem. vol. 39, pp. 3929-3937 (1996).
Votta et al., Bone, vol. 15 (5) pp. 533-538 (1994).
Bradlerova et al., Chem. Zvesti, vol. 29 (6), pp. 795-802 (1975).
de Silva et al., J. Chem. Soc., vol. 4, pp. 685-690 (1995).
Engel & Steglich, Liebigs Ann. Chem., p. 1916 (1978).
Ferles et al., Collect. Czech. Chem. Commun., 5 (46), pp. 1167-1172 (1981).
Fischer et al., Rec. Trav. Chim. Pays. Bas., vol. 84, p. 439 (1965).
Fulmer et al., J. Heterocycl. Chem., vol. 17 (4), pp. 799-800 (1980).
Gilbert, E., Synthesis, pp. 30-32 (1972).
Han et al., Science, vol. 265, pp. 808-811 (1994).
Hunter et al., Academic Press, San Diego, vol. 200, p. 3 (1991).
Irwin et al., Archives of Internal Medicine, vol. 157 (17), pp. 1981-1987 (1997).
Ishibashi et al., Chem. Pharm. Bull., vol. 37(8), pp. 2214-2216 (1989).
Johnson et al., PG.A., J.Chem.Soc., Perkin Trans., vol. 1, pp. 895-905 (1996).
Jurkowska-Kowalczyk, R., Chem., vol. 51(6), pp. 1191-1199 (1977).
Katritzky et al., Synthesis, pp. 45-47 (Jan. 1993).
Kawasaki et al., J. Bio. Chem., vol. 272(30), pp. 18518-18521 (1997).
Mikailu et al., Zh. Obshch. Khim., vol. 56 (7), pp. 1513-1517 (1986).
Morton et al., Tetrahedron Letters, p. 4123 (1982).
Protecting Groups in Organic Synthesis, 2$^{nd}$ Edition, Greene TW and Wuts PSM, Wiley-Interscience, NewYork, pp. 10-174 (Hydroxyl and Phenolic) and pp. 309-403 (NH protection) (1991).

Santilli et al., J. Heterocycl Chem., vol. 8, pp. 445-453 (1971).
Snieckus, V., Tetrahedron Letters, vol. 29, p. 2135 (1988).
Stille et al., J. Amer. Chem. Soc., vol. 109, p. 5478 (1978).
Strzybny et al., J. Org. Chem., vol. 28, p. 3381 (1963).
Terashimia et al., M., Chem. Pharm. Bull., vol. 11, p. 4755 (1985).
Thompson et al., J. Org. Chem., vol. 49, p. 5237 (1984).
Uno et al., Bull. Chem. Soc. Japan., vol. 69, pp. 1763-1767 (1996).
Vartanyan et al., vol. 40, (9), pp. 552-560 (1987).
Borrel, et al., Coll. Czech. Chem. Commun., 1996, 61(6) pp. 901-909.
Hurlbert, et al., J. Med. Chem., 1968, vol. 11, pp. 703-707.
Baker et al., J. Heterocyclic Chem., 1964, vol. 1, pp. 263-270.
Anderson et al., J. Org. Chem., 1977, vol. 42, p. 993.
Schoffstall et al., J. Org. Chem., 1971, 36(16), pp. 2385-2387.
Victory et al., Heterocycles, 1985, 23(5), pp. 1135-1141.
Gallagher et al., Bioorganic and Med Chem, vol. 5(1), pp. 49-64 (1997).
Garigipati, R., Tetrahedron Letters, vol. 31,p. 190 (1989).
Kumada et al., Tetrahedron Letters, vol. 22, p. 5319 (1981).
Lamartina et al., Boll. Chim. Farm., vol. 129 (12), pp. 314-316 (1990).
Victory et al., Heterocycles, 1985, 23(8), pp. 1947-1950.
Victory et al., AFINIDAD, Mar. 1989, vol. 46, pp. 107-113 (Spanish).
Victory et al., J. Heterocycl. Chem, 1988, vol. 25, pp. 245-247.
Klotzer et al., Monatsh Chem., 1965, vol. 96, p. 1567.
Nishikawa et al., Chemical Pharm. Bull., 1976, vol. 24(9), pp. 2057-2077.
Carboni et al., *Gazzetta Chimica Italiana*, vol. 97(8) pp. 1262-1273 (1967).
Carboni et al., *Gazzetta Chimica Italiana*, vol. 98(10) pp. 1174-1188 (1968).
Ferrarini et al., *Journal of Heterocyclic Chemistry*, vol. 21(2) pp. 417-419 (1984).
Ferrarini et al., *Journal of Heterocyclic Chemistry*, vol. 34(5) pp. 1501-1510 (1997).
Rewcastle et al., Journal of Medicinal Chemistry, 1996 39(6), pp. 1823-1835.
Zavyalov, et al., Khim Farm Zh, vol. 26(3), p. 88 (1992) (With Translation).
Foster, et al., *Drug News Perspect.*, vol. 13(8) pp. 488-497 (2000).
Hanson, G., *Expert Opinion on Therapeutic Patents*, vol. 7(7) pp. 729-733 (1997).
Henry, et al., *Bioorganic & Medicinal Chemistry Letters*, vol. 8 pp. 3335-3340 (1998).
Herlaar, et al., *Molecular Medicine Today*, vol. 5 pp. 439-447 (1999).
Khabar, Khalid, *Journal of Interferon & Cytokine Research*, vol. 25 pp. 1-10 (2005).
Lee, et al., *Immunopharmacology*, vol. 47(2-3) pp. 185-201 (2000).
Marin, et al., *Blood*, vol. 98(3) pp. 667-673 (2001).
Underwood, et al., *Journal of Pharmacology and Experimental Therapeutics*, vol. 293 (1) pp. 281-288 (2000).
Wadsworth, et al., *Journal of Pharmacology and Experimental Therapeutics*, vol. 291(2) pp. 680-687 (1999).
Hare, et al., *J. Med Chem.*, vol. 47 pp. 4731-4740 (2004).
Hunt, et al., *Bioorganic & Medicinal Chemistry Letters*, vol. 13 pp. 467-470 (2003).
Tanji, et al., Chem. Pharm. Bull., vol. 35 (12) pp. 4972-4976 (1987).
Tumkevicius, Liebigs Ann., pp. 1703-1705 (1995).
Tumkevicius, Chem. Hetero. Compounds, vol. 36 (7) pp. 841-846 (2000).
Solberg, et al., Acta Chemica Scandinavica, vol. 43 pp. 62-68 (1989).

* cited by examiner

Citric Acid Induced Cough Model

Antigen- or LTD$_4$-Induced Hypertussive Model in the Guinea Pig

Effects of Dextromethorphan or Codeine On Citric Acid-Induced Cough in Guinea Pigs

US 7,629,462 B2

TETRASUBSTITUTED PYRIMIDINE COMPOUNDS AS CHEMICAL INTERMEDIATES

This application is a continuation of U.S. Ser. No. 10/220,103 filed 28 Aug. 2002 (Allowed) now U.S. Pat. No. 7,235,551, which is the national stage entry of PCT/US01/06688, filed 2 Mar. 2001, and claims the benefit of priority of U.S. Provisional Application 60/186,419 filed 2 Mar. 2000.

FIELD OF THE INVENTION

This invention relates to a novel group of 1,5-disubstituted-3,4-dihydro-1H-pyrimido[4,5-d]pyrimidin-2-one compounds, processes for the preparation thereof, the use thereof in treating CSBP/p38 kinase mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell, 80, 179-278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995); Seger, R., and Krebs, E. G. FASEB J., 726-735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). The first indications suggesting that the signal transduction pathway leading to LPS-induced cytokine biosynthesis involved protein kinases came from studies of Weinstein [Weinstein, et al., J. Immunol. 151, 3829 (1993)] but the specific protein kinases involved were not identified. Working from a similar perspective, Han [Han, et al., Science 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., Int. J. Immunopharmac. 10(7), 835(1988)] and exhibited activity in animal models which are refractory to cyclooxygenase inhibitors [Lee; et al., Annals N. Y. Acad. Sci., 696, 149(1993)].

It is now firmly established that CSBP/p38 is a one of several kinases involved in a stress-response signal transduction pathway, which is parallel to and largely independent of the analogous mitogen-activated protein kinase (MAP) kinase cascade. Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 1). Additional downstream substrates known to be phosphorylated by p38 include kinases (Mnk1/2, MSK1/2 and PRAK) and transcription factors (CHOP, MEF2, ATF2 and CREB). While many of the signaling pathways required for cytokine biosynthesis remain unknown it appears clear that many of the substrates for p38 listed above are involved. [Cohen, P. Trends Cell Biol., 353-361(1997) and Lee, J. C. et al, Pharmacol. Ther. vol. 82, nos. 2-3, pp. 389-397, 1999].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. Trends Cell Biol., 353-361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic B cells [review of the biological activities which have been attributed to IL-1 Dinarello, J. Clinical Immunology, 5 (5), 287-297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds, which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453-1461. (1996); Griswold, et al, *Pharmacol. Comm.* 7, 323-229 (1996)].

The field of patents and patent applications disclosing compounds useful for the treatment of p38 mediated diseases has expanded rapidly over the last several years. In most instances the central core molecule has been an imidazole, oxazole or pyrazole derivative, such as those disclosed in WO 93/14081; WO 93/14082; WO 95/02591; WO 95/13067; WO 95/31451; WO 99/58523; WO 98/56377; WO 97/16442; WO 99/57101; WO 00/39116; and WO 00/31063. Newer ring systems include cycloalkenyl, pyrimidine, pyrazine, and triazole cores such as WO 00/25791; WO 98/24782; WO 99/17776; WO 00/10563; WO 00/25791; and WO 00/35911; and multi ring systems, such as WO 99/64400; WO 98/22457; WO 00/20402; WO 00/12497; WO 99/61426 and WO 99/58502.

However, despite all of this research effort there still remains a need for treatments in this field, for compounds which inhibit the CSBP/p38/RK kinase, and are useful in the treatment of disease mediated thereby.

SUMMARY OF THE INVENTION

Figure 1:
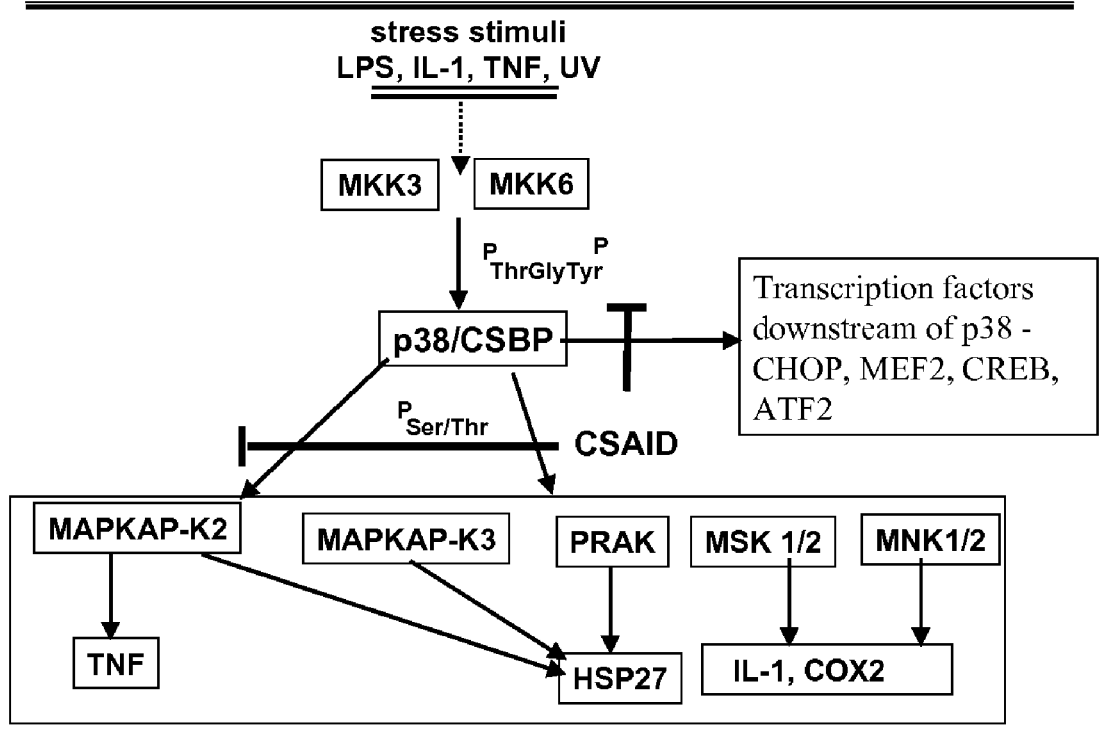
FIG. 1 demonstrates the p38 kinase cascade.

This invention relates to the novel compounds of Formulas (I) to (V) and (Ia) to (Va), and pharmaceutical compositions comprising a compound of Formula (I) to (V) and (Ia) to (Va), and a pharmaceutically acceptable diluent or carrier.

This invention relates to a method of treating, including prophylaxis, of a CSBP/RK/p38 kinase mediated disease in a mammal in need thereof, which comprises administering to said mammal an effective amount of a compound of Formulas (I) to (V) and (Ia) to (Va).

Accordingly, the present invention provides a compound of Formula (I):

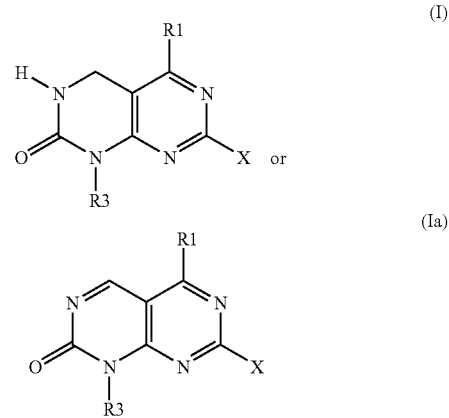

wherein $R_1$ is an aryl or heteroaryl ring, which ring is optionally substituted;

$R_2$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety; and wherein each of these moieties, excluding hydrogen, are optionally substituted;

$R_3$ is a $C_{1-10}$ alkyl, $C_{3-7}$cycloalkyl, $C_{3-7}$ cycloalkyl$C_{1-10}$ alkyl, aryl$C_{1-10}$ alkyl, heteroaryl$C_{1-10}$ alkyl, or heterocyclyl$C_{1-10}$ alkyl moiety; and wherein each of these moieties are optionally substituted;

X is $R_2$, $OR_2$, $S(O)_m R_2$ or $(CH_2)_n NR_4 R_{14}$, or $(CH_2)_n NR_2 R_4$;

n is 0 or an integer having a value of 1 to 10;

m is 0 or an integer having a value of 1 or 2;

$R_4$ and $R_{14}$ are each independently selected from hydrogen, optionally substituted $C_{1-4}$ alkyl, optionally substituted aryl, or an optionally substituted aryl$C_{1-4}$alkyl, or $R_4$ and $R_{14}$ together with the nitrogen to which they are attached form a heterocyclic ring of 5 to 7 members, which ring optionally contains an additional heteroatom selected from oxygen, sulfur or $NR_9$, and which ring may be optionally substituted;

$R_6$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or a heteroaryl$C_{1-10}$ alkyl moiety; and wherein each of these moieties, excluding hydrogen, may be optionally substituted;

R9 is hydrogen, C(Z)R6, optionally substituted $C_{1-10}$ alkyl, optionally substituted aryl or optionally substituted aryl$C_{1-4}$ alkyl;

Z is oxygen or sulfur;

or a pharmaceutically acceptable salt thereof.

Another aspect of the present invention is the novel compounds of Formula (II) represented by the structure:

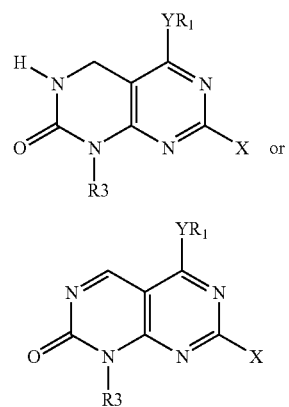

wherein

R1 is an aryl or a heteroaryl ring, which ring may be optionally substituted;

R2 is hydrogen, $C_{1-10}$ alkyl, $C_{3-7}$cycloalkyl, $C_{3-7}$cycloalkyl$C_{1-10}$ alkyl, aryl, aryl$C_{1-10}$ alkyl, heteroaryl, heteroaryl$C_{1-10}$ alkyl, heterocyclic, or a heterocyclyl$C_{1-10}$ alkyl moiety; and wherein each of these moieties, excluding hydrogen, are optionally substituted;

R3 is an $C_{1-10}$alkyl, $C_{3-7}$cycloalkyl, $C_{3-7}$cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety; and wherein each of these moieties are optionally substituted;

Y is $CR_b$, C(O), N($R_d$), oxygen, or S(O)m;

$R_b$ is hydrogen, $C_{1-2}$ alkyl, $NR_c$, hydroxy, thio, $C_{1-2}$ alkoxy, or $S(O)_mC_{1-2}$ alkyl;

$R_c$ is hydrogen or $C_{1-2}$ alkyl;

$R_d$ is hydrogen or $C_{1-2}$ alkyl;

X is $R_2$, $OR_2$, $S(O)_mR_2$, $(CH_2)_nNR_4R_{14}$, or $(CH_2)_nNR_2R_4$;

m is 0 or an integer having a value of 1 or 2;

n is 0 or an integer having a value of 1 to 10;

R4 and R14 are each independently selected from hydrogen, optionally substituted $C_{1-4}$ alkyl, optionally substituted aryl, or an optionally substituted aryl$C_{1-4}$alkyl, or R4 and R14 together with the nitrogen which they are attached form a heterocyclic ring of 5 to 7 members which ring optionally contains an additional heteroatom selected from oxygen, sulfur or $NR_9$, and which ring may be optionally substituted;

R6 is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl; and wherein each of these moieties, excluding hydrogen, may be optionally substituted;

R9 is hydrogen, C(Z)R6 or optionally substituted $C_{1-10}$ alkyl, optionally substituted aryl or optionally substituted aryl-$C_{1-4}$ alkyl;

Z is oxygen or sulfur;

or a pharmaceutically acceptable salt thereof.

Another aspect of the present invention are the novel compounds of Formula (III) represented by the structure:

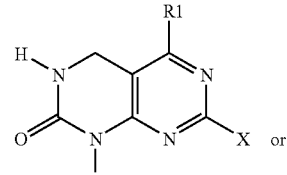

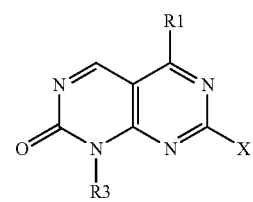

wherein

R1 is an aryl, or a heteroaryl ring, which ring may be optionally substituted;

R2 is a heterocyclic or heterocyclic$C_{1-10}$ alkyl ring, which is ring is optionally substituted;

R2, is a heterocyclic, heterocyclic$C_{1-10}$ alkyl, aryl, or heteroaryl ring, which ring is optionally substituted;

R3 is an aryl or heteroaryl ring, which ring is optionally substituted;

X is $R_{2'}$, $OR_2$, $S(O)_mR_2$ or $(CH_2)_nNR_4R_{14}$, or $(CH_2)_nNR_2R_4$; provided that when X is $(CH_2)_nNR_4R_{14}$, then $R_4R_{14}$ must form the optionally substituted cyclized ring optionally comprising an oxygen, sulfur or nitrogen moiety;

n is 0 or an integer having a value of 1 to 10;

m is 0 or an integer having a value of 1 or 2;

R4 and R14 are independently selected from hydrogen, optionally substituted $C_{1-4}$ alkyl, optionally substituted aryl, or optionally substituted aryl$C_{1-4}$ alkyl; or R4 and R14 together with the nitrogen which they are attached form a heterocyclic ring of 5 to 7 members which ring optionally contains an additional heteroatom selected from oxygen, sulfur or $NR_9$, and which ring is optionally substituted;

R6 is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety; and wherein each of these moieties, excluding hydrogen, is optionally substituted;

R9 is hydrogen, C(Z)R6, optionally substituted $C_{1-10}$ alkyl, optionally substituted aryl, or optionally substituted aryl$C_{1-4}$ alkyl;

Z is oxygen or sulfur;

or a pharmaceutically acceptable salt thereof.

Another aspect of the present invention are the novel compounds of Formula (IV) represented by the structures:

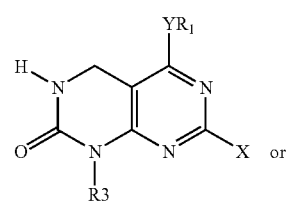

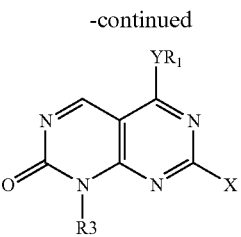

(IVa)

wherein $R_1$ is an aryl or a heteroaryl ring, which ring is optionally substituted;

$R_2$ is hydrogen, $C_{1-10}$alkyl, $C_{3-7}$ cycloalkyl, $C_{3-7}$ cycloalkyl$C_{1-10}$alkyl, aryl, aryl$C_{1-10}$alkyl, heteroaryl, heteroaryl$C_{1-10}$ alkyl, heterocyclic, or a heterocyclyl$C_{1-10}$ alkyl moiety; and wherein each of these moieties, excluding hydrogen, are optionally substituted;

$R_3$ is a $C_{1-10}$ alkyl, $C_{3-7}$ cycloalkyl, $C_{3-7}$ cycloalkyl$C_{1-10}$alkyl, aryl, aryl$C_{1-10}$alkyl, heteroaryl, heteroaryl$C_{1-10}$ alkyl, heterocyclic, or a heterocyclyl$C_{1-10}$ alkyl moiety; and wherein each of these moieties are optionally substituted;

Y is a bond, $CR_b$, $C(O)$, $N(R_d)$, oxygen, or $S(O)m$;

$R_b$ is hydrogen, $C_{1-2}$alkyl, $NR_c$, hydroxy, thio, $C_{1-2}$alkoxy, $S(O)_mC_{1-2}$alkyl;

$R_c$ is hydrogen or $C_{1-2}$alkyl;

$R_d$ is hydrogen or $C_{1-2}$alkyl;

X is $R_2$, $OR_2$, $S(O)_mR_2$ or $(CH_2)_nNR_4R_{14}$, or $(CH_2)_nNR_2R_4$;

n is 0 or an integer having a value of 1 to 10;

m is 0 or an integer having a value of 1 or 2;

$R_4$ and $R_{14}$ are each independently selected from hydrogen, optionally substituted $C_{1-4}$ alkyl, optionally substituted aryl, or optionally substituted aryl$C_{1-4}$ alkyl, or $R_4$ and $R_{14}$ together with the nitrogen which they are attached form a heterocyclic ring of 5 to 7 members which ring optionally contains an additional heteroatom selected from oxygen, sulfur or $NR_9$, and which ring is optionally substituted;

$R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety, and wherein each of these moieties, excluding hydrogen, is optionally substituted;

$R_9$ is hydrogen, $C(Z)R_6$, optionally substituted $C_{1-10}$ alkyl, optionally substituted aryl or an optionally substituted aryl-$C_{1-4}$ alkyl;

Z is oxygen or sulfur;

or a pharmaceutically acceptable salt thereof.

Accordingly, the present invention also provides for a compound of Formula (V):

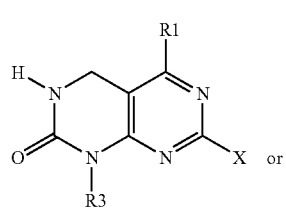

(V)

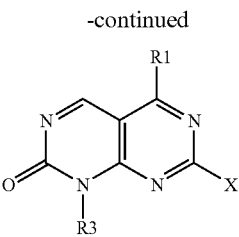

(Va)

wherein

X is $R_2$, $OR_2$, $S(O)_mR_2$ or $(CH_2)_nNR_4R_{14}$, or $(CH_2)_nNR_2R_4$;

n is 0 or an integer having a value of 1 to 10;

m is 0 or an integer having a value of 1 or 2;

$R_1$ is an optionally substituted aryl ring;

$R_2$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$ alkyl, heteroaryl, heteroaryl$C_{1-10}$ alkyl, heterocyclic, or a heterocyclyl$C_{1-10}$ alkyl moiety; and wherein each of these moieties, excluding hydrogen are optionally substituted;

$R_3$ is an optionally substituted aryl ring;

$R_4$ and $R_{14}$ are each independently selected from hydrogen, optionally substituted $C_{1-4}$ alkyl, optionally substituted aryl, or optionally substituted aryl-$C_{1-4}$ alkyl, or $R_4$ and $R_{14}$ together with the nitrogen which they are attached form a heterocyclic ring of 5 to 7 members which ring optionally contains an additional heteroatom selected from oxygen, sulfur or $NR_9$, and which ring is optionally substituted;

$R_6$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or a heteroaryl$C_{1-10}$ alkyl moiety; and wherein each of these moieties, excluding hydrogen, may be optionally substituted;

$R_9$ is hydrogen, $C(Z)R_6$, optionally substituted $C_{1-10}$ alkyl, optionally substituted aryl or an optionally substituted aryl$C_{1-4}$ alkyl;

Z is oxygen or sulfur;

or a pharmaceutically acceptable salt thereof.

DETAILED DESCRIPTION OF THE INVENTION

The present invention is directed to the novel compounds of Formulas (I) to (V), and Formula (Ia) to (Va), or a pharmaceutically acceptable salt thereof, pharmaceutical compositions comprising a compound of Formula (I) to (V), and (Ia) to (Va), or a pharmaceutically acceptable salt thereof, and a pharmaceutically acceptable carrier or diluent thereof, and also to the use of these compounds in the treatment or prophylaxis of CSBP mediated diseases in a mammal in need thereof.

As will be readily recognized, the difference between compounds of Formula (I) to (V) and (Ia) to (Va) lie in the unsaturation of the pyrimidine-2-one ring. The respective $R_1$, $R_2$, X and $R_3$ terms are the same for both groups within a formula set, i.e. I and Ia. For purposes herein, everything applicable to Formula (T) is also applicable to Formula (Ia), Formula (II) and (Ia), Formula (III) and (IIIa), and Formula (V) and (Va) unless otherwise indicated. It should be noted that compounds of Formula (I), (II), (III) and (V) are all subsets of compounds of Formula (IV).

More specifically, the present invention is directed to the novel compounds of Formulas (I) and (Ia), or pharmaceutically acceptable salts thereof.

Suitably, for these compounds of Formula (I) and (Ia), $R_1$ is an aryl, or a heteroaryl ring, which ring is optionally substituted. The ring may be substituted one or more times, in any ring, suitably 1 to 4 times, preferably 1 to 2 times, independently, by halogen, $C_{1-4}$ alkyl, halo-substituted-$C_{1-4}$ alkyl, cyano, nitro, $(CR_{10}R_{20})_v NR_4R_{14}$, $(CR_{10}R_{20})_v C(Z)NR_4R_{14}$, $(CR_{10}R_{20})_v C(Z)OR_8$, $(CR_{10}R_{20})_v COR_a$, $(CR_{10}R_{20})_v C(O)H$, $S(O)_m R_5$, $(CR_{10}R_{20})_v OR_8$, $ZC(Z)R_{11}$, $NR_{10}C(Z)R_{11}$, or $NR_{10}S(O)_2R_7$. Preferably the ring is an aryl ring, more preferably phenyl, which ring is unsubstituted or substituted one or more times by halogen, preferably chloro or fluoro, or alkyl, preferably methyl. Suitably, the ring is substituted in the 4-position, and if di-substituted, it is in the 2-,4-position of the phenyl ring.

Suitably m is 0 or an integer having a value of 1 or 2.

Suitably, v is 0 or an integer having a value of 1 or 2.

Suitably, Z is oxygen or sulfur.

Suitably, $R_a$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_v OR_7$, $(CR_{10}R_{20})_v S(O)_m R_7$, $(CR_{10}R_{20})_v NHS(O)_2 R_7$, or $(CR_{10}R_{20})_v NR_4R_{14}$; and wherein the alkyl, cycloalkyl, cycloalkenyl, aryl, arylalkyl, heterocyclyl, heterocyclylalkyl, heteroaryl, and heteroaryl alkyl moieties may be optionally substituted.

Suitably, $R_4$ and $R_{14}$ are each independently selected from hydrogen, optionally substituted $C_{1-6}$ alkyl, optionally substituted aryl, or an optionally substituted aryl-$C_{1-6}$ alkyl, or $R_4$ and $R_{14}$ together with the nitrogen to which they are attached in $NR_4R_{14}$ substituent may form a heterocyclic ring of 5 to 7 members which ring optionally contains an additional heteroatom selected from oxygen, sulfur or $NR_9$, and which ring may be optionally substituted.

Suitably, $R_5$ is hydrogen, $C_{1-4}$ alkyl, $C_{2-4}$ alkenyl, $C_{2-4}$ alkynyl or $NR_4R_{14}$, excluding the moieties $SR_5$ (wherein m is 0) being $SNR_4R_{14}$, $S(O)_2R_5$ being $SO_2H$ (wherein m is 2) and $S(O)R_5$ being SOH, (wherein m is 1).

Suitably, $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$alkyl, heteroaryl or a heteroaryl$C_{1-10}$ alkyl moiety, and wherein each of these moieties may be optionally substituted. It is recognized herein that hydrogen can not be substituted and is therefore excluded.

Suitably, $R_7$ is $C_{1-6}$alkyl, aryl, aryl$C_{1-6}$alkyl, heterocyclic, heterocyclyl$C_{1-6}$ alkyl, heteroaryl, or a heteroaryl$C_{1-6}$alkyl moiety; and wherein each of these moieties may be optionally substituted.

Suitably, $R_8$ is hydrogen, $C_{1-4}$ alkyl, halo-substituted $C_{1-4}$ alkyl, $C_{2-4}$alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_t OR_7$, $(CR_{10}R_{20})_t S(O)_m R_7$, $(CR_{10}R_{20})_t NHS(O)_2 R_7$, or $(CR_{10}R_{20})_t NR_4R_{14}$; and wherein the alkyl, cycloalkyl, cycloalkenyl, aryl, arylalkyl, heterocyclyl, heterocyclyl alkyl, heteroaryl, and heteroaryl alkyl moieties, may be optionally substituted.

Suitably, t is an integer having a value of 1 to 3.

Suitably, $R_9$ is hydrogen, $C(Z)R_6$, optionally substituted $C_{1-10}$ alkyl, optionally substituted aryl, or optionally substituted aryl-$C_{1-4}$ alkyl.

Suitably, $R_{10}$ and $R_{20}$ are each independently selected from hydrogen or $C_{1-4}$ alkyl.

Suitably, $R_{11}$ is $C_{1-4}$ alkyl, halo-substituted $C_{1-4}$ alkyl, $C_{2-4}$ alkenyl, $C_{2-4}$alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_t OR_7$, $(CR_{10}R_{20})_t S(O)_m R_7$, $(CR_{10}R_{20})_t NHS(O)_2 R_7$, or $(CR_{10}R_{20})_t NR_4R_{14}$; and wherein the alkyl, cycloalkyl, cycloalkenyl, aryl, arylalkyl, heterocyclyl, heterocyclylalkyl, heteroaryl, and heteroaryl alkyl moieties may be optionally substituted.

Suitably, $R_3$ is a $C_{1-10}$alkyl, $C_{3-7}$ cycloalkyl, $C_{3-7}$ cycloalkyl$C_{1-10}$alkyl, aryl$C_{1-10}$ alkyl, heteroaryl$C_{1-10}$ alkyl, or a heterocyclyl$C_{1-10}$ alkyl moiety, and wherein each of these moieties may be optionally substituted, independently, one or more times, suitably 1 to 4 times, preferably 1 to 2 times, (in any applicable ring) with $C_{1-10}$ alkyl, halosubstituted $C_{1-10}$ alkyl, $C_{2-10}$alkenyl, $C_{2-10}$alkynyl, $C_{3-7}$ cycloalkyl, $C_{3-7}$cycloalkyl$C_{1-10}$alkyl, $C_{5-7}$ cycloalkenyl, $C_{5-7}$cycloalkenyl$C_{1-10}$ alkyl, halogen, $(CR_{10}R_{20})_n OR_6$, $(CR_{10}R_{20})_n SH$, $(CR_{10}R_{20})_n S(O)_m R_7$, $(CR_{10}R_{20})_n NHS(O)_2 R_7$, $(CR_{10}R_{20})_n NR_4R_{14}$, $(CR_{10}R_{20})_n CN$, $(CR_{10}R_{20})_n S(O)_2 NR_4R_{14}$, $(CR_{10}R_{20})_n C(Z)R_6$, $(CR_{10}R_{20})_n OC(Z)R_6$, $(CR_{10}R_{20})_n C(Z)OR_6$, $(CR_{10}R_{20})_n C(Z)NR_4R_{14}$, $(CR_{10}R_{20})_n NR_{10}C(Z)R_6$, $(CR_{10}R_{20})_n NR_{10}C(=NR_{10})NR_4R_{14}$, $(CR_{10}R_{20})_n OC(Z)NR_4R_{14}$, $(CR_{10}R_{20})_n NR_{10}C(Z)NR_4R_{14}$, or $(CR_{10}R_{20})_n NR_{10}C(Z)OR_7$.

Preferably, $R_3$ is an optionally substituted $C_{3-7}$ cycloalkyl, or aryl$C_{1-10}$ alkyl, more preferably optionally substituted cyclohexyl, benzyl or phenethyl. Preferably, the ring is unsubstituted or substituted one or more times, independently with halogen, more preferably fluorine, or chlorine, or alkyl, such as methyl. The ring is preferably substituted in the 2-position or di-substituted in the 2-,6-position, more preferably with fluorine, methyl, difluoro, or dimethyl.

Suitably, n is 0, or an integer having a value of 1 to 10.

Suitably, $R_2$ is hydrogen, $C_{1-10}$alkyl, $C_{3-7}$ cycloalkyl, $C_{3-7}$cycloalkyl$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety; and wherein these moieties, excluding hydrogen, may be optionally substituted one or more times, suitably 1 to 4 times, independently (in any applicable ring) with $C_{1-10}$ alkyl, halo-substituted $C_{1-10}$ alkyl, $C_{2-10}$ alkenyl, $C_{2-10}$ alkynyl, $C_{3-7}$cycloalkyl, $C_{3-7}$cycloalkyl$C_{1-10}$alkyl, $C_{5-7}$cycloalkenyl, $C_{5-7}$cycloalkenyl$C_{1-10}$alkyl, halogen, $(CR_{10}R_{20})_n OR_6$, $(CR_{10}R_{20})_n SH$, $(CR_{10}R_{20})_n S(O)_m R_7$, $(CR_{10}R_{20})_n NHS(O)_2 R_7$, $(CR_{10}R_{20})_n NR_4R_{14}$, $(CR_{10}R_{20})_n CN$, $(CR_{10}R_{20})_n S(O)_2 NR_4R_{14}$, $(CR_{10}R_{20})_n C(Z)R_6$, $(CR_{10}R_{20})_n OC(Z)R_6$, $(CR_{10}R_{20})_n C(Z)OR_6$, $(CR_{10}R_{20})_n C(Z)NR_4R_{14}$, $(CR_{10}R_{20})_n NR_{10}C(Z)R_6$, $(CR_{10}R_{20})_n NR_{10}C(=NR_{10})NR_4R_{14}$, $(CR_{10}R_{20})_n OC(Z)NR_4R_{14}$, $(CR_{10}R_{20})_n NR_{10}C(Z)NR_4R_{14}$, $(CR_{10}R_{20})_n NR_{10}C(Z)OR_7$, or a dioxyalkylene group of the formula $-O-(CH_2)_s-O-$, wherein s is 1 to 3, preferably s is 2 yielding a 1,3-dioxyethylene moiety.

Suitably, X is $R_2$, $OR_2$, $S(O)_m R_2$ or $(CH_2)_n NR_4R_{14}$, or $(CH_2)_n NR_2R_4$.

Suitably, when X is the group $OR_2$, then $R_2$ is preferably an optionally substituted $C_{1-10}$ alkyl, an optionally substituted aryl, arylalkyl, heteroaryl, heteroarylalkyl, heterocyclic or heterocyclicalkyl moiety. Preferably, when the $R_2$ moiety is an alkyl it is a substituted or unsubstituted $C_{1-6}$ alkyl, Suitably, the alkyl substituents are as defined herein, but are preferably, halogen, hydroxy, or $NR_4R_{14}$. When $R_2$ is an optionally substituted heterocyclic, or heterocyclic alkyl ring, it is preferably a pyrrolidine, piperidine, piperazine, morpholine ring or a pyrrolidinyl alkyl, piperidinyl alkyl, piperazinyl alkyl, or a morpholinyl alkyl. More preferably, it is a piperidine or an alkyl substituted piperidine, such as N-methyl piperidine.

Preferably, when X is the group $S(O)_m R_2$, $R_2$ is a substituted or unsubstituted alkyl, aryl or aryl alkyl.

Preferably, when X is the group $(CH_2)_n NR_4R_{14}$, n is preferably 0 or 1, more preferably 0. Preferably, if the $R_4$ and $R_{14}$ moiety cyclize the ring is a 5 or 6 membered ring, such as a pyrrolidine, piperidine, piperazine, or morpholine containing ring, which ring may be optionally substituted. Preferably when $R_4$ or $R_{14}$ is an optionally substituted $C_{1-6}$alkyl, which chain may be a straight or branched chain, it is substituted one or more times, suitably 1 to 4 times, preferably 1 or 2 times, with halogen; hydroxy; hydroxy substituted $C_{1-10}$alkyl; $C_{1-10}$alkoxy; halosubstituted $C_{1-10}$ alkoxy; S(O)m $C_{1-4}$alkyl, wherein m is 0, 1 or 2; $NR_4R_{14}$, such as amino or mono or -disubstituted $C_{1-6}$ alkyl or wherein the $R_4R_{14}$ can cyclize together with the nitrogen to which they are attached to form a 5 to 7 membered ring which optionally contains an additional heteroatom selected from O/N/S; $C_{3-7}$cycloalkyl; $C_{3-7}$cycloalkyl $C_{1-10}$ alkyl group; halosubstituted $C_{1-10}$ alkyl, such $CF_2CF_2H$, or $CF_3$; optionally substituted aryl, such as phenyl, or an optionally substituted arylalkyl, such as benzyl or phenethyl; and wherein these aryl or arylalkyl moieties may also themselves be substituted one to two times by halogen; hydroxy; hydroxy substituted alkyl; $C_{1-10}$ alkoxy; $S(O)_m$ $C_{1-4}$ alkyl; amino, mono & di-substituted $C_{1-6}$ alkyl amino, such as in the $NR_4R_{14}$ group; $C_{1-4}$ alkyl, or $CF_3$.

Preferably, the alkyl chain is branched, such as in t-butyl or isopropyl. More preferably the alkyl chain is substituted one or more times, independently by halogen, hydroxy, amino, or mono or di $C_{1-4}$ alkyl substituted amino.

Preferably, when X is the group $(CH_2)_nNR_2R_4$, n is preferably 0 or 1, more preferably 0. The $R_2$ moiety is preferably, hydrogen, substituted or unsubstituted alkyl, substituted or unsubstituted heterocyclic, substituted or unsubstituted heterocyclic alkyl, substituted or unsubstituted heteroaryl, or substituted or unsubstituted heteroarylalkyl. Such groups preferably include imidazole, tetrazole, pyrrolidine, piperidine, piperazine, morpholine, pyrrolidinyl alkyl, piperidinyl alkyl, piperazinyl alkyl, or morpholinyl alkyl.

Preferably, when X is the group $R_2$, then $R_2$ is preferably an optionally substituted heteroaryl, such as an imidazole, or tetrazole, or is an optionally substituted heterocyclic ring, such as a pyrrolidine, piperidine, piperazine, or a morpholine ring Another aspect of the present invention is directed to the compounds of Formula (II) and (IIa).

Suitably, for compounds of Formula (II) and (IIa), $R_1$ is an aryl or a heteroaryl ring, which ring may be optionally substituted. The ring may be substituted one or more times, in any ring, suitably 1 to 4 times, preferably 1 to 2 times, independently, by halogen, $C_{1-4}$ alkyl, halo-substituted-$C_{1-4}$ alkyl, cyano, nitro, $(CR_{10}R_{20})_vNR_4R_{14}$, $(CR_{10}R_{20})_vC(Z)NR_4R_{14}$, $(CR_{10}R_{20})_vC(Z)OR_8$, $(CR_{10}R_{20})_vCOR_a$, $(CR_{10}R_{20})_vC(O)H$, $S(O)_mR_5$, $(CR_{10}R_{20})_vOR_8$, $ZC(Z)R_{11}$, $NR_{10}C(Z)R_{11}$, or $NR_{10}S(O)_2R_7$. Preferably the ring is an aryl ring, more preferably phenyl, which ring is unsubstituted or substituted one or more times by halogen, preferably chloro or fluoro, or alkyl, preferably methyl. Suitably, the ring is substituted in the 4-position, and if di-substituted, it is in the 2-,4-position of the phenyl ring.

Suitably, v is 0 or an integer having a value of 1 or 2.

Suitably, Z is oxygen or sulfur.

Suitably, $R_a$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_vNHS(O)_2R_7$, or $(CR_{10}R_{20})_vNR_4R_{14}$; and wherein the cycloalkyl, $C_{5-7}$ cycloalkenyl, aryl, arylalkyl, heterocyclyl, heterocyclylalkyl, heteroaryl, or heteroarylalkyl moiety may be optionally substituted.

Suitably, $R_4$ and $R_{14}$ is each independently selected from hydrogen, optionally substituted $C_{1-6}$ alkyl, optionally substituted aryl, or optionally substituted aryl-$C_{1-6}$ alkyl, or $R_4$ and $R_{14}$ together with the nitrogen which they are attached form a heterocyclic ring of 5 to 7 members which ring optionally contains an additional heteroatom selected from oxygen, sulfur or $NR_9$, and which ring may be optionally substituted.

Suitably, $R_5$ is hydrogen, $C_{1-4}$ alkyl, $C_{2-4}$ alkenyl, $C_{2-4}$ alkynyl or $NR_4R_{14}$, excluding the moieties $SR_5$ (wherein m is 0) being $SNR_4R_{14}$, $S(O)_2R_5$ being $SO_2H$ (wherein m is 2) and $S(O)R_5$ being SOH, (wherein m is 1).

Suitably, $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety, and wherein each of these moieties may be optionally substituted (excluding hydrogen).

Suitably, $R_7$ is $C_{1-6}$alkyl, aryl, aryl$C_{1-6}$alkyl, heterocyclic, heterocyclyl$C_{1-6}$ alkyl, heteroaryl, or a heteroaryl$C_{1-6}$alkyl; and wherein each of these moieties may be optionally substituted.

Suitably, $R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_tNHS(O)_2R_7$, or $(CR_{10}R_{20})_t NR_4R_{14}$; and wherein the alkyl, cycloalkyl, cycloalkenyl, aryl, arylalkyl, heterocyclyl, heterocyclylalkyl heteroaryl, and heteroaryl alkyl moieties may be optionally substituted.

Suitably, t is an integer having a value of 1 to 3.

Suitably, $R_9$ is hydrogen, $C(Z)R_6$, optionally substituted $C_{1-10}$ alkyl, optionally substituted aryl, or optionally substituted aryl-$C_{1-4}$ alkyl.

Suitably, $R_{10}$ and $R_{20}$ are each independently selected from hydrogen or $C_{1-4}$ alkyl.

Suitably, $R_{11}$ is $C_{1-4}$ alkyl, halo-substituted $C_{1-4}$ alkyl, $C_{2-4}$ alkenyl, $C_{2-4}$alkynyl, $C_{3-7}$cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$alkyl, $(CR_{10}R_{20})_tOR_7$, $(CR_{10}R_{20})_tS(O)_mR_7$, $(CR_{10}R_{20})_tNHS(O)_2R_7$, or $(CR_{10}R_{20})_tNR_4R_{14}$; and wherein the alkyl, cycloalkyl, cycloalkenyl, aryl, arylalkyl, heterocyclyl, heterocyclylalkyl, heteroaryl, and heteroaryl alkyl moieties may be optionally substituted.

Suitably m is 0 or an integer having a value of 1 or 2.

Suitably, X is $R_2$, $OR_2$, $S(O)_mR_2$ or $(CH_2)_nNR_4R_{14}$, or $(CH_2)_nNR_2R_4$.

Suitably, Y is $CR_b$, C(O), $N(R_d)$, oxygen, or S(O)m.

Suitably, $R_b$ is hydrogen, $C_{1-2}$ alkyl, $NR_c$, hydroxy, thio, $C_{1-2}$ alkoxy, $S(O)_mC_{1-2}$ alkyl.

Suitably, $R_c$ is hydrogen or $C_{1-2}$ alkyl.

Suitably, $R_d$ is hydrogen or $C_{1-2}$ alkyl.

Suitably, $R_3$ is a $C_{1-10}$ alkyl, $C_{3-7}$ cycloalkyl, $C_{3-7}$ cycloalkyl$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, and wherein each of these moieties may be optionally substituted, independently, one or more times, suitably 1 to 4 times, preferably 1 to 2 times, (in any applicable ring) with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_n$ CN, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

Preferably, $R_3$ is an optionally substituted $C_{3-7}$ cycloalkyl, aryl, or aryl$C_{1-10}$ alkyl, more preferably optionally substituted cyclohexyl, phenyl, benzyl or phenethyl. Preferably, the ring is unsubstituted or substituted one or more times, independently with halogen, more preferably fluorine, or chlorine, or alkyl, such as methyl. The ring is preferably substituted in the 2-position or di-substituted in the 2-,6-position, more preferably with fluorine, methyl, difluoro, or dimethyl.

Suitably, n is 0, or an integer having a value of 1 to 10.

Suitably, $R_2$ is hydrogen, $C_{1-10}$ alkyl, $C_{3-7}$cycloalkyl, $C_{3-7}$cycloalkyl$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety; and wherein each of these moieties, excluding hydrogen, may be optionally substituted one or more times, suitably 1 to 4 times, independently (in any applicable ring), with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_n$CN, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, $(CR_{10}R_{20})_nNR_{10}C(Z)OR_7$, or a dioxyalkylene group of the formula —O—$(CH_2)_s$—O—, wherein s is 1 to 3, preferably s is 2 yielding a 1,3-dioxyethylene moiety.

Suitably, when X is the group $OR_2$, then $R_2$ is preferably an optionally substituted $C_{1-10}$ alkyl, an optionally substituted aryl, arylalkyl, heteroaryl, heteroarylalkyl, heterocyclic or heterocyclicalkyl moiety. Preferably, when the $R_2$ moiety is an alkyl it is a substituted or unsubstituted $C_{1-6}$ alkyl moiety as defined above. Preferably, the alkyl substituents are independently selected from halogen, $(CR_{10}R_{20})_nOR_6$, or $(CR_{10}R_{20})_nNR_4R_{14}$.

When $R_2$ is an optionally substituted heterocyclic or heterocyclic alkyl ring, it is preferably a pyrrolidine, piperidine, piperazine, or morpholine ring, or a pyrrolidinyl alkyl, piperidinyl alkyl, piperazinyl alkyl, or a morpholinyl alkyl ring. More preferably, it is a piperidine or an alkyl substituted piperidine, such as N-methyl piperidine.

Preferred substituents include halogen, $C_{1-10}$alkyl, halo-substituted $C_{1-10}$alkyl, $(CR_{10}R_{20})_nNR_4R_{14}$, $(CR_{10}R_{20})_nOR_6$, and $(CR_{10}R_{20})_nC(Z)OR_6$.

Preferably, when X is the group $S(O)_mR_2$, $R_2$ is a substituted or unsubstituted $C_{1-10}$alkyl, aryl or arylalkyl.

Preferably, when X is the group $(CH_2)_nNR_4R_{14}$, n is preferably 0 or 1, more preferably 0. Preferably if the $R_4$ and $R_{14}$ moiety cyclize the ring is a 5 or 6 membered ring, such as a pyrrolidine, piperidine, piperazine, or morpholine containing ring, which ring may be optionally substituted. Preferably, when $R_4$ or $R_{14}$ is an optionally substituted $C_{1-6}$alkyl, which chain may be a straight or branched chain, it is substituted one or more times, suitably 1 to 4 times, preferably 1 or 2 times, with halogen; hydroxy; hydroxy substituted $C_{1-10}$alkyl; $C_{1-10}$ alkoxy; halosubstituted $C_{1-10}$ alkoxy; $S(O)m$ $C_{1-4}$alkyl, wherein m is 0, 1 or 2; $NR_4R_{14}$, such as amino or mono or -disubstituted $C_{1-6}$ alkyl or wherein the $R_4R_{14}$ can cyclize together with the nitrogen to which they are attached to form a 5 to 7 membered ring which optionally contains an additional heteroatom selected from O/N/S; $C_{3-7}$cycloalkyl; $C_{3-7}$cycloalkyl $C_{1-10}$ alkyl group; halosubstituted $C_{1-10}$ alkyl, such $CF_2CF_2H$, or $CF_3$; optionally substituted aryl, such as phenyl, or an optionally substituted arylalkyl, such as benzyl or phenethyl; and wherein these aryl or arylalkyl moieties may also themselves be substituted one to two times by halogen; hydroxy; hydroxy substituted alkyl; $C_{1-10}$ alkoxy; $S(O)_m$ $C_{1-4}$ alkyl; amino, mono & di-substituted $C_{1-6}$ alkyl amino, such as in the $NR_4R_{14}$ group; $C_{1-4}$ alkyl, or $CF_3$.

Preferably, the alkyl chain is branched, such as in t-butyl or isopropyl. More preferably the alkyl chain is substituted one or more times, independently by halogen, hydroxy, amino, or mono or di $C_{1-4}$ alkyl substituted amino.

Preferably, when X is the group $(CH_2)_nNR_2R_4$, n is preferably 0 or 1, more preferably 0. The $R_2$ moiety is preferably, hydrogen, substituted or unsubstituted alkyl, substituted or unsubstituted heterocyclic, substituted or unsubstituted heterocyclic alkyl, substituted or unsubstituted heteroaryl, or substituted or unsubstituted heteroarylalkyl. Such groups preferably include imidazole, tetrazole, pyrrolidine, piperidine, piperazine, morpholine, and 2-,3- or 4-pyridyl, pyrrolidinyl alkyl, piperidinyl alkyl, piperazinyl alkyl, or morpholinyl alkyl.

Preferably, when X is the group $R_2$, then $R_2$ is preferably an optionally substituted heteroaryl, such as an imidazole, or tetrazole, or is an optionally substituted heterocyclic ring, such as a pyrrolidine, piperidine, piperazine, or a morpholine ring Another aspect of the present invention are the novel compounds of Formula (III) and (IIIa).

Suitably, for compounds of Formula (III) and (IIa), $R_1$ is an aryl or heteroaryl ring, which ring may be optionally substituted. The ring may be substituted one or more times, in any ring, suitably 1 to 4 times, preferably 1 to times, independently, by halogen, $C_{1-4}$ alkyl, halo-substituted-$C_{1-4}$ alkyl, cyano, nitro, $(CR_{10}R_{20})_vNR_4R_{14}$, $(CR_{10}R_{20})_vC(Z)NR_4R_{14}$, $(CR_{10}R_{20})_vC(Z)OR_8$, $(CR_{10}R_{20})_vCOR_a$, $(CR_{10}R_{20})_vC(O)H$, $S(O)_mR_5$, $(CR_{10}R_{20})_vOR_8$, $ZC(Z)R_{11}$, $NR_{10}C(Z)R_{11}$, or $NR_{10}S(O)_2R_7$. Preferably the ring is an aryl ring, more preferably phenyl, which ring is unsubstituted or substituted one or more times by halogen, preferably chloro or fluoro, or alkyl, preferably methyl. Suitably, the ring is substituted in the 4-position, and if di-substituted, it is in the 2-,4-position of the phenyl ring.

Suitably m is 0 or an integer having a value of 1 or 2.

Suitably, v is 0 or an integer having a value of 1 or 2.

Suitably, Z is oxygen or sulfur.

Suitably, $R_a$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_m R_7$, $(CR_{10}R_{20})_vNHS(O)_2R_7$, or $(CR_{10}R_{20})_vNR_4R_{14}$; and wherein the alkyl, cycloalkyl, cycloalkenyl, aryl, arylalkyl, heterocyclyl, heterocyclylalkyl, heteroaryl, and heteroarylalkyl moieties may be optionally substituted.

Suitably, $R_4$ and $R_{14}$ are each independently selected from hydrogen, optionally substituted $C_{1-6}$ alkyl, optionally substituted aryl, or an optionally substituted aryl-$C_{1-6}$ alkyl; or $R_4$ and $R_{14}$ together with the nitrogen which they are attached form a heterocyclic ring of 5 to 7 members which ring optionally contains an additional heteroatom selected from oxygen, sulfur or $NR_9$, and which ring may be optionally substituted.

Suitably, $R_5$ is hydrogen, $C_{1-4}$ alkyl, $C_{2-4}$ alkenyl, $C_{2-4}$ alkynyl or $NR_4R_{14}$, excluding the moieties $SR_5$ (wherein m is 0) being $SNR_4R_{14}$, $S(O)_2R_5$ being $SO_2H$ (wherein m is 2) and $S(O)R_5$ being SOH, (wherein m is 1).

Suitably, $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety; and wherein each of these moieties, excluding hydrogen, may be optionally substituted.

Suitably, $R_7$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl moiety; and wherein each of these moieties may be optionally substituted.

Suitably, $R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$alkyl, heteroaryl, heteroaryl$C_{1-4}$ alkyl, heterocyclyl, heterocyclylC$_{1-4}$ alkyl, (CR$_{10}$R$_{20}$)$_t$OR$_7$, (CR$_{10}$R$_{20}$)$_t$S(O)$_m$ R$_7$, (CR$_{10}$R$_{20}$)$_t$NHS(O)$_2$R$_7$, or (CR$_{10}$R$_{20}$)$_t$NR$_4$R$_{14}$; and wherein the alkyl, cycloalkyl, cycloalkenyl, aryl, arylalkyl, heterocyclyl, heterocyclylalkyl, heteroaryl, and heteroaryl alkyl moieties, may be optionally substituted.

Suitably, t is an integer having a value of 1 to 3.

Suitably, R$_9$ is hydrogen, C(Z)R$_6$, optionally substituted C$_{1-10}$ alkyl, optionally substituted aryl or optionally substituted aryl-C$_{1-4}$ alkyl.

Suitably, R$_{10}$ and R$_{20}$ are each independently selected from hydrogen or C$_{1-4}$ alkyl.

Suitably, R$_{11}$ is C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{5-7}$ cycloalkenyl, aryl, arylC$_{1-4}$ alkyl, heteroaryl, heteroarylC$_{1-4}$ alkyl, heterocyclyl, heterocyclylC$_{1-4}$ alkyl, (CR$_{10}$R$_{20}$)$_t$OR$_7$, (CR$_{10}$R$_{20}$)$_t$S(O)$_m$R$_7$, (CR$_{10}$R$_{20}$)$_t$NHS(O)$_2$R$_7$, or (CR$_{10}$R$_{20}$)$_t$NR$_4$R$_{14}$; and wherein the alkyl, cycloalkyl, cycloalkenyl, aryl, arylalkyl, heterocyclyl, heterocyclylalkyl, heteroaryl, and heteroaryl alkyl moieties may be optionally substituted.

Suitably X is R$_{2'}$, OR$_2$, S(O)$_m$R$_2$ or (CH$_2$)$_n$NR$_4$R$_{14}$, or (CH$_2$)$_n$NR$_2$R$_4$; provided that when is X is (CH$_2$)$_n$NR$_4$R$_{14}$, then R$_4$R$_{14}$ forms the optionally substituted cyclized ring optionally comprising an oxygen, sulfur or nitrogen moiety as defined herein.

Suitably, R$_3$ is an optionally substituted aryl, or optionally substituted heteroaryl moiety. The R$_3$ moieties be optionally substituted one or more times independently with C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$ cycloalkenyl C$_{1-10}$ alkyl, halogen, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$NHS(O)$_2$R$_7$, (CR$_{10}$R$_{20}$)$_n$NR$_4$R$_{14}$, (CR$_{10}$R$_{20}$)$_n$CN, (CR$_{10}$R$_{20}$)$_n$S(O)$_2$NR$_4$R$_{14}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_4$R$_{14}$, (CR$_{10}$R$_{20}$)$_n$NR$_{10}$C(Z)R$_6$, (CR$_{10}$R$_{20}$)$_n$NR$_{10}$C(=NR$_{10}$)NR$_4$R$_{14}$, (CR$_{10}$R$_{20}$)$_n$OC(Z)NR$_4$R$_{14}$, (CR$_{10}$R$_{20}$)$_n$NR$_{10}$C(Z)NR$_4$R$_{14}$, or (CR$_{10}$R$_{20}$)$_n$NR$_{10}$C(Z)OR$_7$.

Preferably, R$_3$ is an optionally substituted aryl, more preferably optionally substituted phenyl. Preferably, the ring is unsubstituted or substituted one or more times, independently with halogen, more preferably fluorine, or chlorine, or alkyl, such as methyl. The ring is preferably substituted in the 2-position or di-substituted in the 2-,6-position, more preferably with fluorine, methyl, difluoro, or dimethyl.

Suitably, n is 0, or an integer having a value of 1 to 10.

Suitably, R$_2$ is a heterocyclic, or heterocyclylC$_{1-10}$ alkyl ring, which ring or rings(s) are optionally substituted one or more times, suitably 1 to 4, independently with C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$ cycloalkenyl C$_{1-10}$ alkyl, halo (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$NHS(O)$_2$R$_7$, (CR$_{10}$R$_{20}$)$_n$NR$_4$R$_{14}$, (CR$_{10}$R$_{20}$)$_n$CN, (CR$_{10}$R$_{20}$)$_n$S(O)$_2$NR$_4$R$_{14}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_4$R$_{14}$, (CR$_{10}$R$_{20}$)$_n$NR$_{10}$C(Z)R$_6$, (CR$_{10}$R$_{20}$)$_n$NR$_{10}$C(=NR$_{10}$)NR$_4$R$_{14}$, (CR$_{10}$R$_{20}$)$_n$OC(Z)NR$_4$R$_{14}$, (CR$_{10}$R$_{20}$)$_n$NR$_{10}$C(Z)NR$_4$R$_{14}$, (CR$_{10}$R$_{20}$)$_n$NR$_{10}$C(Z)OR$_7$, or a dioxyalkylene group of the formula —O—(CH$_2$)$_s$—O—, wherein s is 1 to 3, preferably s is 2 yielding a 1,3-dioxyethylene moiety.

Suitably, R$_{2'}$ is a heterocyclic, heterocyclylC$_{1-10}$ alkyl, aryl, or heteroaryl ring, which ring or rings(s) are optionally substituted one or more times, suitably 1 to 4 times, in any ring, independently with C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$ cycloalkenyl C$_{1-10}$ alkyl, halogen, (CR$_{10}$R$_{20}$)$_n$OR$_6$, (CR$_{10}$R$_{20}$)$_n$SH, (CR$_{10}$R$_{20}$)$_n$S(O)$_m$R$_7$, (CR$_{10}$R$_{20}$)$_n$NHS(O)$_2$R$_7$, (CR$_{10}$R$_{20}$)$_n$NR$_4$R$_{14}$, (CR$_{10}$R$_{20}$)$_n$CN, (CR$_{10}$R$_{20}$)$_n$S(O)$_2$NR$_4$R$_{14}$, (CR$_{10}$R$_{20}$)$_n$C(Z)R$_6$, (CR$_{10}$R$_{20}$)$_n$OC(Z)R$_6$, (CR$_{10}$R$_{20}$)$_n$C(Z)OR$_6$, (CR$_{10}$R$_{20}$)$_n$C(Z)NR$_4$R$_{14}$, (CR$_{10}$R$_{20}$)$_n$NR$_{10}$C(Z)R$_6$, (CR$_{10}$R$_{20}$)$_n$NR$_{10}$C(=NR$_{10}$)NR$_4$R$_{14}$, (CR$_{10}$R$_{20}$)$_n$OC(Z)NR$_4$R$_{14}$, (CR$_{10}$R$_{20}$)$_n$NR$_{10}$C(Z)NR$_4$R$_{14}$, (CR$_{10}$R$_{20}$)$_n$NR$_{10}$C(Z)OR$_7$, or a dioxyalkylene group of the formula —O—(CH$_2$)$_s$—O—, wherein s is 1 to 3, preferably s is 2 yielding a 1,3-dioxyethylene moiety.

Suitably, the optionally substituted R$_2$ or R$_{2'}$ heterocyclic ring is a pyrrolidine, piperidine, piperazine, or morpholine ring or a pyrrolidinyl alkyl, piperidinyl alkyl, piperazinyl alkyl, or a morpholinyl alkyl. More preferably, it is a piperidine or an alkyl substituted piperidine, such as N-methyl piperidine.

Suitably, when R$_{2'}$ is an optionally substituted aryl or heteroaryl ring, the ring is an optionally substituted phenyl, imidazole or tetrazole ring.

Another aspect of the present invention is the novel compounds of Formula (IV) and (IVa).

Suitably, for compounds of Formula (IV) and (IVa), R$_1$ is an aryl or heteroaryl ring, which ring is optionally substituted. The ring may be substituted one or more times, in any ring, suitably 1 to 4 times, preferably 1 to 2 times, independently, by halogen, C$_{1-4}$ alkyl, halo-substituted-C$_{1-4}$ alkyl, cyano, nitro, (CR$_{10}$R$_{20}$)$_v$NR$_4$R$_{14}$, (CR$_{10}$R$_{20}$)$_v$C(Z)NR$_4$R$_{14}$, (CR$_{10}$R$_{20}$)$_v$C(Z)OR$_8$, (CR$_{10}$R$_{20}$)$_v$COR$_a$, (CR$_{10}$R$_{20}$)$_v$C(O)H, S(O)$_m$R$_5$, (CR$_{10}$R$_{20}$)$_v$OR$_8$, ZC(Z)R$_{11}$, NR$_{10}$C(Z)R$_{11}$, or NR$_{10}$S(O)$_2$R$_7$. Preferably the ring is an aryl ring, more preferably phenyl, which ring is unsubstituted or substituted one or more times by halogen, preferably chloro or fluoro, or alkyl, preferably methyl. Suitably, the ring is substituted in the 4-position, and if di-substituted, it is in the 2-,4-position of the phenyl ring. Most preferably R$_1$ is a 2-methyl-4-fluoro phenyl.

Suitably m is 0 or an integer having a value of 1 or 2.

Suitably, v is 0 or an integer having a value of 1 or 2.

Suitably, Z is oxygen or sulfur.

Suitably, R$_a$ is C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{5-7}$ cycloalkenyl, aryl, arylC$_{1-4}$ alkyl, heteroaryl, heteroarylC$_{1-4}$ alkyl, heterocyclyl, heterocyclylC$_{1-4}$ alkyl, (CR$_{10}$R$_{20}$)$_v$OR$_7$, (CR$_{10}$R$_{20}$)$_v$S(O)$_m$R$_7$, (CR$_{10}$R$_{20}$)$_v$NHS(O)$_2$R$_7$, or (CR$_{10}$R$_{20}$)$_v$NR$_4$R$_{14}$; and wherein the alkyl, cycloalkyl, cycloalkenyl, aryl, arylalkyl, heterocyclyl, heterocyclylalkyl, heteroaryl, and heteroarylalkyl moieties may be optionally substituted.

Suitably, R$_4$ and R$_{14}$ are each independently selected from hydrogen, optionally substituted C$_{1-6}$ alkyl, optionally substituted aryl or an optionally substituted aryl-C$_{1-6}$ alkyl, or R$_4$ and R$_{14}$ together with the nitrogen which they are attached form a heterocyclic ring of 5 to 7 members which ring optionally contains an additional heteroatom selected from oxygen, sulfur or NR$_9$, and which ring may be optionally substituted.

Suitably, R$_5$ is hydrogen, C$_{1-4}$ alkyl, C$_{2-4}$ alkenyl, C$_{2-4}$ alkynyl or NR$_4$R$_{14}$, excluding the moieties SR$_5$ (wherein m is 0) being SNR$_4$R$_{14}$, S(O)$_2$R$_5$ being SO$_2$H (wherein m is 2) and S(O)R$_5$ being SOH, (wherein m is 1).

Suitably, R$_6$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl; and wherein each of these moieties, excluding hydrogen, may be optionally substituted.

Suitably, R$_7$ is C$_{1-6}$alkyl, aryl, arylC$_{1-6}$alkyl, heterocyclic, heterocyclylC$_{1-6}$ alkyl, heteroaryl, or heteroarylC$_{1-6}$alkyl; and wherein each of these moieties may be optionally substituted.

Suitably, $R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_nOR_7$, $(CR_{10}R_{20})_sS(O)_mR_7$, $(CR_{10}R_{20})_nNHS(O)_2R_7$, or $(CR_{10}R_{20})_nNR_4R_{14}$; and wherein the alkyl, cycloalkyl, cycloalkenyl, aryl, arylalkyl, heterocyclyl, heterocyclyl alkyl, heteroaryl, and heteroaryl alkyl moieties may be optionally substituted.

Suitably, t is an integer having a value of 1 to 3.

Suitably, $R_9$ is hydrogen, $C(Z)R_6$, optionally substituted $C_{1-10}$ alkyl, optionally substituted aryl or optionally substituted aryl-$C_{1-4}$ alkyl.

Suitably, $R_{10}$ and $R_{20}$ are each independently selected from hydrogen or $C_{1-4}$ alkyl.

Suitably, $R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_sS(O)_mR_7$, $(CR_{10}R_{20})_tNHS(O)_2R_7$, or $(CR_{10}R_{20})_tNR_4R_{14}$; and wherein the alkyl, cycloalkyl, cycloalkenyl, aryl, arylalkyl, heterocyclyl, heterocyclylalkyl, heteroaryl, and heteroaryl alkyl moieties may be optionally substituted.

Suitably, $R_3$ is hydrogen, an $C_{1-10}$ alkyl, $C_{3-7}$ cycloalkyl, $C_{3-7}$cycloalkyl$C_{1-10}$alkyl, aryl, aryl$C_{1-10}$ alkyl, heteroaryl, heteroaryl$C_{1-10}$alkyl, heterocyclic, or a heterocyclyl$C_{1-10}$ alkyl moiety; and wherein each of these moieties, excluding hydrogen, may be optionally substituted, independently, one or more times, suitably 1 to 4 times, preferably 1 to 2 times, in any ring if applicable, with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$ $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

Preferably, $R_3$ is an optionally substituted $C_{1-10}$alkyl, aryl, aryl$C_{1-10}$alkyl, or a cycloalkyl moiety, more preferably optionally substituted $C_{1-5}$ alkyl, cyclohexyl, phenyl, benzyl or phenethyl. Preferably, the ring is unsubstituted or substituted one or more times, independently with halogen, more preferably fluorine, or chlorine, or alkyl, such as methyl. The ring is preferably substituted in the 2-position or di-substituted in the 2-,6-position, more preferably with fluorine, methyl, difluoro, or dimethyl.

Suitably, X is $R_2$, $OR_2$, $S(O)_mR_2$, $(CH_2)_nNR_4R_{14}$, or $(CH_2)_n NR_2R_4$.

Suitably, $R_2$ is hydrogen, $C_{1-10}$ alkyl, $C_{3-7}$ cycloalkyl, $C_{3-7}$ cycloalkyl$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety; and wherein each of these moieties, excluding hydrogen, may optionally substituted one or more times, suitable 1 to 4 times, independently, and in any ring, with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, $(CR_{10}R_{20})_nNR_{10}C(Z)OR_7$, or a dioxyalkylene group of the formula $—O—(CH_2)_s—O—$, wherein s is 1 to 3, preferably s is 2 yielding a 1,3-dioxyethylene moiety.

Suitably, n is 0, or an integer having a value of 1 to 10.

Suitably, when X is the group $OR_2$, then $R_2$ is preferably an optionally substituted $C_{1-10}$ alkyl, an optionally substituted aryl, arylalkyl, heteroaryl, heteroarylalkyl, heterocyclic or heterocyclicalkyl moiety. Preferably, when the $R_2$ moiety is an alkyl it is a substituted or unsubstituted $C_{1-6}$ alkyl. Suitably, the alkyl substituents are halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

Preferably, the alkyl substituents are halogen, $(CR_{10}R_{20})_nOR_6$, or $(CR_{10}R_{20})_nNR_4R_{14}$.

When $R_2$ is an optionally substituted heterocyclic or heterocyclic alkyl ring, it is preferably a pyrrolidine, piperidine, piperazine, or morpholine ring, or is a pyrrolidinyl alkyl, piperidinyl alkyl, piperazinyl alkyl, or morpholinyl alkyl ring. More preferably, it is a piperidine or an alkyl substituted piperidine, such as N-methyl piperidine.

Preferred substituents include halogen, $C_{1-10}$alkyl, halo-substituted $C_{1-10}$alkyl, $(CR_{10}R_{20})_nNR_4R_{14}$, $(CR_{10}R_{20})_nOR_6$, and $(CR_{10}R_{20})_nC(Z)OR_6$.

Preferably when X is the group $S(O)_mR_2$, $R_2$ is a substituted or unsubstituted $C_{1-10}$alkyl, aryl or arylalkyl. While the X group $S(O)_mR_2$ moiety is a compound of Formula (IV) it is also a key intermediate in the process of making other compounds of Formula (IV) as can be seen by Scheme I herein. Preferably for this use, m is 0 and $R_2$ is a short chain alkyl, such as methyl.

Preferably, when X is the group $(CH_2)_nNR_4R_{14}$, n is preferably 0 or 1, more preferably 0. Preferably, if the $R_4$ and $R_{14}$ moiety cyclize the ring is a 5 or 6 membered ring, such as a pyrrolidine, piperidine, piperazine, or morpholine containing ring, which ring may be optionally substituted. Preferably, when $R_4$ or $R_{14}$ is an optionally substituted $C_{1-6}$alkyl, which chain may be a straight or branched chain, it is substituted one or more times, independently, suitably 1 to 4 times, preferably 1 or 2 times, with halogen; hydroxy; hydroxy substituted $C_{1-10}$alkyl; $C_{1-10}$ alkoxy; halosubstituted $C_{1-10}$ alkoxy; $S(O)m$ $C_{1-4}$alkyl, wherein m is 0, 1 or 2; $NR_4R_{14}$, such as amino or mono or -disubstituted $C_{1-4}$ alkyl or wherein the $R_4R_{14}$ can cyclize together with the nitrogen to which they are attached to form a 5 to 7 membered ring which optionally contains an additional heteroatom selected from O/N/S; $C_{3-7}$cycloalkyl; $C_{3-7}$cycloalkyl $C_{1-10}$ alkyl group; halosubstituted $C_{1-10}$ alkyl, such $CF_2CF_2H$, or $CF_3$; optionally substituted aryl, such as phenyl, or an optionally substituted arylalkyl, such as benzyl or phenethyl; and wherein these aryl or arylalkyl moieties may also themselves be substituted one to two times by halogen; hydroxy; hydroxy substituted alkyl; $C_{1-10}$ alkoxy; $S(O)_m$ $C_{1-4}$ alkyl; amino, mono & di-substituted $C_{1-4}$ alkyl amino, such as in the $NR_4R_{14}$ group; $C_{1-4}$ alkyl, or $CF_3$.

Preferably, the alkyl chain is branched, such as in t-butyl or isopropyl. More preferably the alkyl chain is substituted one or more times, independently by halogen, hydroxy, amino, or mono or di $C_{1-4}$ alkyl substituted amino.

Preferably, when X is the group $(CH_2)_nNR_2R_4$, n is preferably 0 or 1, more preferably 0. Preferably one of $R_2$ or $R_4$ is hydrogen and the other is an optionally substituted moiety. The $R_2$ moiety is preferably, hydrogen, substituted or unsubstituted alkyl, substituted or unsubstituted heterocyclic, substituted or unsubstituted heterocyclic alkyl, substituted or unsubstituted heteroaryl, or substituted or unsubstituted heteroarylalkyl. When $R_2$ is an optionally substituted heterocyclic, heterocyclic alkyl, or heteroaryl group such groups are preferably an imidazole, tetrazole, pyrrolidine, piperidine, piperazine, morpholine and 2-, 3- or 4-pyridyl; pyrrolidinyl alkyl, piperidinyl alkyl, piperazinyl alkyl, or morpholinyl alkyl.

When the $R_2$ moiety is an optionally substituted $C_{1-10}$ alkyl, the chain may be straight or branched, and substituted one or more times, suitably 1 to 4 times, independently by halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_n CN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_n C(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_n NR_{10}C(Z)NR_4R_{14}$, $(CR_{10}R_{20})_nNR_{10}C(Z)OR_7$, or dioxyalkylene group of the formula $—O—(CH_2)_s—O—$, wherein s is 1 to 3, preferably s is 2 yielding a 1,3-dioxyethylene moiety.

Preferably, when X is the group $R_2$, then $R_2$ is preferably an optionally substituted heteroaryl, such as an imidazole, or tetrazole, or is an optionally substituted heterocyclic ring, such as a pyrrolidine, piperidine, piperazine, or morpholine ring.

Suitably, Y is a bond, $CR_b$, $C(O)$, $N(R_d)$, oxygen, or $S(O)m$. Preferably Y is a bond.

Suitably, $R_b$ is hydrogen, $C_{1-2}$ alkyl, $NR_c$, hydroxy, thio, $C_{1-2}$ alkoxy, $S(O)_mC_{1-2}$ alkyl.

Suitably, $R_c$ is hydrogen or $C_{1-2}$ alkyl.

Suitably, $R_d$ is hydrogen or $C_{1-2}$ alkyl.

Suitably, m is 0 or an integer having a value of 1 or 2.

Another aspect of the present invention is the novel compounds of Formula (V) and (Va).

Suitably, for compounds of Formula (V) and (Va), $R_1$ is an optionally substituted aryl ring, preferably a phenyl ring. The phenyl or napthyl ring or ring(s) may be substituted one or more times, in any ring, preferably 1 to 4 times, independently, by substituents selected from halogen, $C_{1-4}$ alkyl, halo-substituted-$C_{1-4}$ alkyl, cyano, nitro, $(CR_{10}R_{20})_v NR_4R_{14}$, $(CR_{10}R_{20})_vC(Z)NR_4R_{14}$, $(CR_{10}R_{20})_vC(Z)OR_8$, $(CR_{10}R_{20})_vCOR_a$, $(CR_{10}R_{20})_vC(O)H$, $S(O)_mR_5$, $(CR_{10}R_{20})_v OR_8$, $ZC(Z)R_{11}$, $NR_{10}C(Z)R_{11}$, or $NR_{10}S(O)_2R_7$. Preferably the ring is unsubstituted or substituted one or more times by halogen, preferably chloro or fluoro, or alkyl, preferably methyl. Suitably, the ring is substituted in the 4-position, and if di-substituted, in the 2-,4-position of the phenyl ring.

Suitably, v is 0 or an integer having a value of 1 or 2.

Suitably, Z is oxygen or sulfur.

Suitably, $R_a$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, arylC$_{1-4}$ alkyl, heteroaryl, heteroarylC$_{1-4}$ alkyl, heterocyclyl, heterocyclylC$_{1-4}$ alkyl, $(CR_{10}R_{20})_vOR_7$, $(CR_{10}R_{20})_vS(O)_mR_7$, $(CR_{10}R_{20})_vNHS(O)_2R_7$, or $(CR_{10}R_{20})_vNR_4R_{14}$; and wherein the alkyl, cycloalkyl, cycloalkenyl, aryl, arylalkyl, heterocyclyl, heterocyclyl alkyl, heteroaryl, and heteroaryl alkyl moieties may be optionally substituted.

Suitably, $R_4$ and $R_{14}$ is each independently selected from hydrogen, optionally substituted $C_{1-6}$ alkyl, optionally substituted aryl or optionally substituted aryl-$C_{1-6}$ alkyl, or together with the nitrogen which they are attached form a heterocyclic ring of 5 to 7 members which ring optionally contains an additional heteroatom selected from oxygen, sulfur or $NR_9$, which ring may be optionally substituted.

Suitably, $R_5$ is hydrogen, $C_{1-4}$ alkyl, $C_{2-4}$ alkenyl, $C_{2-4}$ alkynyl or $NR_4R_{14}$, excluding the moieties $SR_5$ (wherein m is 0) being $SNR_4R_{14}$, $S(O)_2R_5$ being $SO_2H$ (wherein m is 2) and $S(O)R_5$ being SOH, (wherein m is 1).

Suitably, $R_6$ is hydrogen, $C_{1-10}$ alkyl, $C_{3-7}$ cycloalkyl, heterocyclyl, heterocyclyl $C_{1-10}$alkyl, aryl, arylC$_{1-10}$ alkyl, heteroaryl or heteroarylC$_{1-10}$ alkyl; and wherein each of these moieties, excluding hydrogen, may be optionally substituted.

Suitably, $R_7$ is $C_{1-6}$alkyl, aryl, arylC$_{1-6}$alkyl, heterocyclic, heterocyclylC$_{1-6}$ alkyl, heteroaryl, or heteroarylC$_{1-6}$alkyl; and wherein each of these moieties may be optionally substituted.

Suitably, $R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, arylC$_{1-4}$ alkyl, heteroaryl, heteroarylC$_{1-4}$ alkyl, heterocyclyl, heterocyclylC$_{1-4}$ alkyl, $(CR_{10}R_{20})_tOR_7$, $(CR_{10}R_{20})_tS(O)_mR_7$, $(CR_{10}R_{20})_tNHS(O)_2R_7$, or $(CR_{10}R_{20})_t NR_4R_{14}$; and wherein the alkyl, cycloalkyl, cycloalkenyl, aryl, arylalkyl, heterocyclyl, heterocyclyl alkyl, heteroaryl, and heteroaryl alkyl moieties may be optionally substituted.

Suitably, t is an integer having a value of 1 to 3.

Suitably, $R_9$ is hydrogen, $C(Z)R_6$, optionally substituted $C_{1-10}$ alkyl, optionally substituted aryl or optionally substituted aryl-$C_{1-4}$ alkyl.

Suitably, $R_{10}$ and $R_{20}$ are each independently selected from hydrogen or $C_{1-4}$ alkyl.

Suitably, $R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, arylC$_{1-4}$ alkyl, heteroaryl, heteroarylC$_{1-4}$ alkyl, heterocyclyl, heterocyclylC$_{1-4}$alkyl, $(CR_{10}R_{20})_tOR_7$, $(CR_{10}R_{20})_tS(O)_mR_7$, $(CR_{10}R_{20})_tNHS(O)_2R_7$, or $(CR_{10}R_{20})_vNR_4R_{14}$; and wherein the alkyl, cycloalkyl, cycloalkenyl, aryl, arylalkyl, heterocyclyl, heterocyclylalkyl, heteroaryl, and heteroaryl alkyl moieties may be optionally substituted.

Suitably m is 0 or an integer having a value of 1 or 2.

Suitably, $R_2$ is hydrogen, $C_{1-10}$ alkyl, $C_{3-7}$ cycloalkyl, $C_{3-7}$cycloalkylC$_{1-10}$alkyl, aryl, arylC$_{1-10}$ alkyl, heteroaryl, heteroarylC$_{1-10}$ alkyl, heterocyclic, or a heterocyclylC$_{1-10}$ alkyl moiety; and wherein each of these moieties, excluding hydrogen, may optionally substituted one or more times independently, preferably 1 to 2 times, with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkylC$_{1-10}$ alkyl, $C_{5-7}$ cycloalkenyl, $C_{5-7}$ cycloalkenyl $C_{1-10}$ alkyl, halo $(CR_{10}R_{20})_nOR_6$, $(CR_{10}R_{20})_n SH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2 NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_n NR_{10}C(Z)R_6$, $(CR_{10}R_{20})_nNR_{10}C(=NR_{10})$ $NR_4R_{14}$, $(CR_{10}R_{20})_nOC(Z)NR_4R_{14}$, $(CR_{10}R_{20})_nNR_{10}C(Z)NR_4R_{14}$, $(CR_{10}R_{20})_nNR_{10}C(Z)OR_7$, or a dioxyalkylene group of the formula $—O—(CH_2)_s—O—$, wherein s is 1 to 3, preferably s is 2 yielding a 1,3-dioxyethylene moiety.

Suitably, $R_3$ is an optionally substituted aryl ring, which ring may be optionally substituted one or more times, independently, in any ring, with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkylC$_{1-10}$alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_n NR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z) NR_4R_{14}$, $(CR_{10}R_{20})_nNR_{10}C(Z)NR_4R_{14}$, or $(CR_{10}R_{20})_n NR_{10}C(Z)OR_7$.

Preferably, $R_3$ is an optionally substituted phenyl. Preferably, the ring is unsubstituted or substituted one or more times, independently with halogen, more preferably fluorine, or chlorine, or alkyl, such as methyl. The ring is preferably substituted in the 2-position or di-substituted in the 2-,6-position, more preferably with fluorine, methyl, difluoro, or dimethyl.

Suitably, n is 0, or an integer having a value of 1 to 10.

Suitably, X is $R_2$, $OR_2$, $S(O)_mR_2$, $(CH_2)_nNR_4R_{14}$, or $(CH_2)_n NR_2R_4$.

Suitably, when X is the group $OR_2$, then $R_2$ is preferably an optionally substituted $C_{1-10}$ alkyl, an optionally substituted aryl, arylalkyl, heteroaryl, heteroarylalkyl, heterocyclic or heterocyclicalkyl moiety. Preferably, when the $R_2$ moiety is an alkyl it is a substituted or unsubstituted $C_{1-6}$ alkyl moiety. Preferably, the alkyl substituents are independently selected from halogen, $(CR_{10}R_{20})_nOR_6$, or $(CR_{10}R_{20})_nNR_4R_{14}$.

When $R_2$ is an optionally substituted heterocyclic or heterocyclic alkyl ring, it is preferably a pyrrolidine, piperidine, piperazine, or morpholine ring, or a pyrrolidinyl alkyl, piperidinyl alkyl, piperazinyl alkyl, or a morpholinyl alkyl ring. More preferably, it is a piperidine or an alkyl substituted piperidine, such as N-methyl piperidine.

Preferred substituents include halogen, $C_{1-10}$alkyl, halosubstituted $C_{1-10}$alkyl, $(CR_{10}R_{20})_nNR_4R_{14}$, $(CR_{10}R_{20})_nOR_6$, and $(CR_{10}R_{20})_nC(Z)OR_6$.

Preferably when X is the group $S(O)_mR_2$, and $R_2$ is a substituted or unsubstituted $C_{1-10}$alkyl, aryl or arylalkyl.

Preferably, when X is the group $(CH_2)_nNR_4R_{14}$, n is preferably 0 or 1, more preferably 0. Preferably if the $R_4$ and $R_{14}$ moiety cyclize the ring is a 5 or 6 membered ring, such as a pyrrolidine, piperidine, piperazine, or morpholine containing ring, which ring may be optionally substituted. Preferably, when $R_4$ or $R_{14}$ is an optionally substituted $C_{1-6}$alkyl, which chain may be a straight or branched chain, it is substituted one or more times, suitably 1 to 4 times, preferably 1 or 2 times, with halogen; hydroxy; hydroxy substituted $C_{1-10}$alkyl; $C_{1-10}$ alkoxy; halosubstituted $C_{1-10}$ alkoxy; $S(O)m$ $C_{1-4}$alkyl, wherein m is 0, 1 or 2; $NR_4R_{14}$, such as amino or mono or -disubstituted $C_{1-6}$ alkyl or wherein the $R_4R_{14}$ can cyclize together with the nitrogen to which they are attached to form a 5 to 7 membered ring which optionally contains an additional heteroatom selected from O/N/S; $C_{3-7}$cycloalkyl; $C_{3-7}$cycloalkyl $C_{1-10}$ alkyl group; halosubstituted $C_{1-10}$ alkyl, such $CF_2CF_2H$, or $CF_3$; optionally substituted aryl, such as phenyl, or an optionally substituted arylalkyl, such as benzyl or phenethyl; and wherein these aryl or arylalkyl moieties may also themselves be substituted one to two times by halogen; hydroxy; hydroxy substituted alkyl; $C_{1-10}$ alkoxy; $S(O)_m$ $C_{1-4}$ alkyl; amino, mono & di-substituted $C_{1-6}$ alkyl amino, such as in the $NR_4R_{14}$ group; $C_{1-4}$ alkyl, or $CF_3$.

Preferably, the alkyl chain is branched, such as in t-butyl or isopropyl. More preferably the alkyl chain is substituted one or more times, independently by halogen, hydroxy, amino, or mono or di $C_{1-4}$ alkyl substituted amino.

Preferably, when X is the group $(CH_2)_nNR_2R_4$, n is preferably 0 or 1, more preferably 0. The $R_2$ moiety is preferably, hydrogen, substituted or unsubstituted alkyl, substituted or unsubstituted heterocyclic, substituted or unsubstituted heterocyclic alkyl, substituted or unsubstituted heteroaryl, or substituted or unsubstituted heteroarylalkyl. Such groups preferably include morpholinoethyl, pyrroleethyl, piperidineethyl, pyridylethyl, or piperidine.

Preferably, when X is the group $R_2$, then $R_2$ is preferably an optionally substituted heteroaryl, such as an imidazole, or tetrazole, or an optionally substituted heterocyclic ring, such as a pyrrolidine, piperidine, piperazine, or a morpholine ring As used herein, "optionally substituted" unless specifically defined shall mean, substituent groups which may be substituted on the applicable moiety one or more times, independently, by halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; $S(O)m$ alkyl, wherein m is 0, 1 or 2, such as methyl thio, methylsulfinyl or methyl sulfonyl; $NR_4R_{14}$, such as amino or mono or -disubstituted $C_{1-4}$ alkyl or wherein the $R_4R_{14}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; optionally substituted aryl, such as phenyl, or an optionally substituted arylalkyl, such as benzyl or phenethyl; and wherein the aryl or arylalkyl moieties may also themselves be substituted one to two times by halogen; hydroxy; hydroxy substituted alkyl; $C_{1-10}$ alkoxy; $S(O)_m$alkyl; amino, mono & di-substituted $C_{1-4}$ alkyl amino, such as in the $NR_4R_{14}$ group; $C_{1-4}$ alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

In addition, pharmaceutically acceptable salts of compounds of Formulas (I) to (IV) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

The term "$C_{1-10}$alkyl" or "alkyl" or "alkyl$_{1-10}$" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to, cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl and naphthyl.

The term "heteroaryl" (on its own or in any combination, such as "heteroaryloxy", or "heteroaryl alkyl") is used herein to mean a 5-10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

The term "heterocyclic" (on its own or in any combination, such as "heterocyclylalkyl") is used herein to mean a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "aralkyl" or "heteroarylalkyl" or "heterocyclicalkyl" or "cycloalkyl alkyl" or cycloalkenylalkyl" is used herein to mean a $C_{1-4}$ alkyl chain, as defined above, which chain is attached to the respective aryl, heteroaryl, heterocyclic, cycloalkyl or cycloalkenyl moiety as also defined herein unless otherwise indicated.

The term "sulfinyl" is used herein to mean the oxide S(O) of the corresponding sulfide; the term "thio" refers to the sulfide; and the term "sulfonyl" refers to the fully oxidized $S(O)_2$ moiety.

The term "aroyl" is used herein to mean C(O)Ar, wherein Ar is as phenyl, naphthyl, or an arylalkyl derivative such as defined above, such group include but are not limited to benzyl and phenethyl.

The term "alkanoyl" is used herein to mean $C(O)C_{1-10}$ alkyl, wherein the alkyl chain is as defined above.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of the compounds of Formulas (I) to (IV) and (Ia) to (IVa) include those described in the synthetic examples, and those noted below, and their pharmaceutically acceptable salt thereof.

Exemplified compounds of Formula (I), include:
7-Methylsulfanyl-5-phenyl-1-(1-phenylethyl)-3,4-dihydro-1H-pyrimido[4,5-d]pyrimidin-2-one
  Exemplified compounds of Formula (Ia), include:
7-Methylsulfanyl-5-phenyl-1-(1-phenylethyl)-1H-pyrimido[4,5-d]pyrimidin-2-one
  Exemplified compounds of Formula (II), include:
5-Benzyl-7-(3-morpholin-4-yl-propylamino)-1-phenyl-3,4-dihydro-1H-pyrimido[4,5-d]pyrimidin-2-one
  Exemplified compounds of Formula (IIa), include:
5-Benzyl-7-(3-morpholin-4-yl-propylamino)-1-phenyl-1H-pyrimido[4,5-d]pyrimidin-2-one
  Exemplified compounds of Formula (III), include:
7-(4-Methyl-piperazin-1-yl)-1,5-diphenyl-3,4-dihydro-1H-pyrimido[4,5-d]pyrimidin-2-one
  Exemplified compounds of Formula (IIIa), include:
7-(4-Methyl-piperazin-1-yl)-1,5-diphenyl-1H-pyrimido[4,5-d]pyrimidin-2-one
  Exemplified compounds of Formula (IV), include, but are not limited to,
1-(2,6-difluorophenyl)-5-(4-fluoro-2-methylphenyl)-7-methylsulfanyl-3,4-dihydro-1H-pyrimido[4,5-d]pyrimidin-2-one;
  Exemplified compounds of Formula (IVa), include:
7-Methylsulfanyl-1,5-diphenyl-1H-pyrimido[4,5-d]pyrimidin-2-one.

The compounds of Formula (I), (II), (III), (IV) and (V) may be obtained by applying synthetic procedures, described herein. The synthesis provided for is applicable to producing compounds of Formula (I) to (V) having a variety of different $R_1$, $R_2$, Y, X, and $R_3$ groups which are reacted, employing optional substituents which are suitably protected, to achieve compatibility with the reactions outlined herein. Subsequent deprotection, in those cases, then affords compounds of the nature generally disclosed.

Once the nucleus has been established, further compounds of Formula (I) may be prepared by applying standard techniques for functional group interconversion, well known in the art. For instance: $C(O)NR_4R_{14}$ from $CO_2CH_3$ by heating with or without catalytic metal cyanide, e.g. NaCN, and $HNR_4R_{14}$ in $CH_3OH$; $OC(O)R_3$ from OH with e.g., $ClC(O)R_3$ in pyridine; $NR_{10}$—$C(S)NR_4R_{14}$ from $NHR_{10}$ with an alkylisothiocyante or thiocyanic acid; $NR_{10}C(O)OR_7$ from $NHR_{10}$ with the alkyl chloroformate; $NR_{10}C(O)NR_4R_{14}$ from $NHR_{10}$ by treatment with an isocyanate, e.g. HN=C=O or $R_{10}N$=C=O; $NR_{10}$—$C(O)R_7$ from $NHR_{10}$ by treatment with Cl—$C(O)R_7$ in pyridine; $C(=NR_{10})NR_4R_{14}$ from $C(NR_4R_{14})SR_3$ with $H_3NR_3^+OAc^-$ by heating in alcohol; $C(NR_4R_{14})SR_3$ from $C(S)NR_4R_{14}$ with $R_6$-I in an inert solvent, e.g. acetone; $C(S)NR_4R_{14}$ (where $R_4$ or $R_{14}$ is not hydrogen) from $C(S)NH_2$ with $HNR_4R_{14}$—$C(=NCN)$—$NR_4R_{14}$ from $C(=NR_4R_{14})$—$SR_3$ with $NH_2CN$ by heating in anhydrous alcohol, alternatively from $C(=NH)$—$NR_4R_{14}$ by treatment with BrCN and NaOEt in EtOH; $NR_{10}SO_2R_3$ from $NHR_{10}$ by treatment with $ClSO_2R_3$ by heating in pyridine; $NR_{10}C(S)R_6$ from $NR_{10}C(O)R_6$ by treatment with Lawesson's reagent [2,4-bis(4-methoxyphenyl)-1,3,2,4-dithiadiphosphetane-2,4-disulfide]; $NR_{10}SO_2CF_3$ from $NHR_6$ with triflic anhydride and base wherein $R_3$, $R_6$, $R_7$, $R_{10}$, $R_4$ and $R_{14}$ are as defined in Formula (IV) herein.

Further, other precursors of the various substituent groups herein may be other groups of compounds of Formula (I) to (V) which may be interconverted by applying standard techniques for this functional group interconversion. Such as use of the S-alkyl intermediate for X in compounds of Formula (IV) which are oxidized and displaced by a suitable nucleophile to yield other final products of Formula (IV). Also for example, wherein a moiety is a halo substituted $C_{1-10}$ alkyl it can be converted to the corresponding $C_{1-10}$ alkyl$N_3$ derivative by reacting with a suitable azide salt, and thereafter if desired can be reduced to the corresponding $C_{1-10}$alkyl$NH_2$ compound, which in turn can be reacted with $R_7S(0)_2X$ wherein X is halo (e.g., chloro) to yield the corresponding $C_{1-10}$alkylNHS$(0)_2R_7$ compound.

Alternatively wherein the moiety is a halo-substituted $C_{1-10}$-alkyl it can be reacted with an amine $R_4R_{14}NH$ to yield the corresponding $C_{1-10}$-alkyl$NR_4R_{14}$ compound, or can be reacted with an alkali metal salt of $R_7SH$ to yield the corresponding $C_{1-10}$alkyl$SR_7$ compound.

Suitable protecting groups for use with hydroxyl groups and nitrogen groups are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, $(CR_{10}R_{20})_n$.

Pharmaceutically acid addition salts of compounds of Formula (I) to (V), and (Ia) to (Va) may be obtained in known manner, for example by treatment thereof with an appropriate amount of acid in the presence of a suitable solvent.

Scheme 1

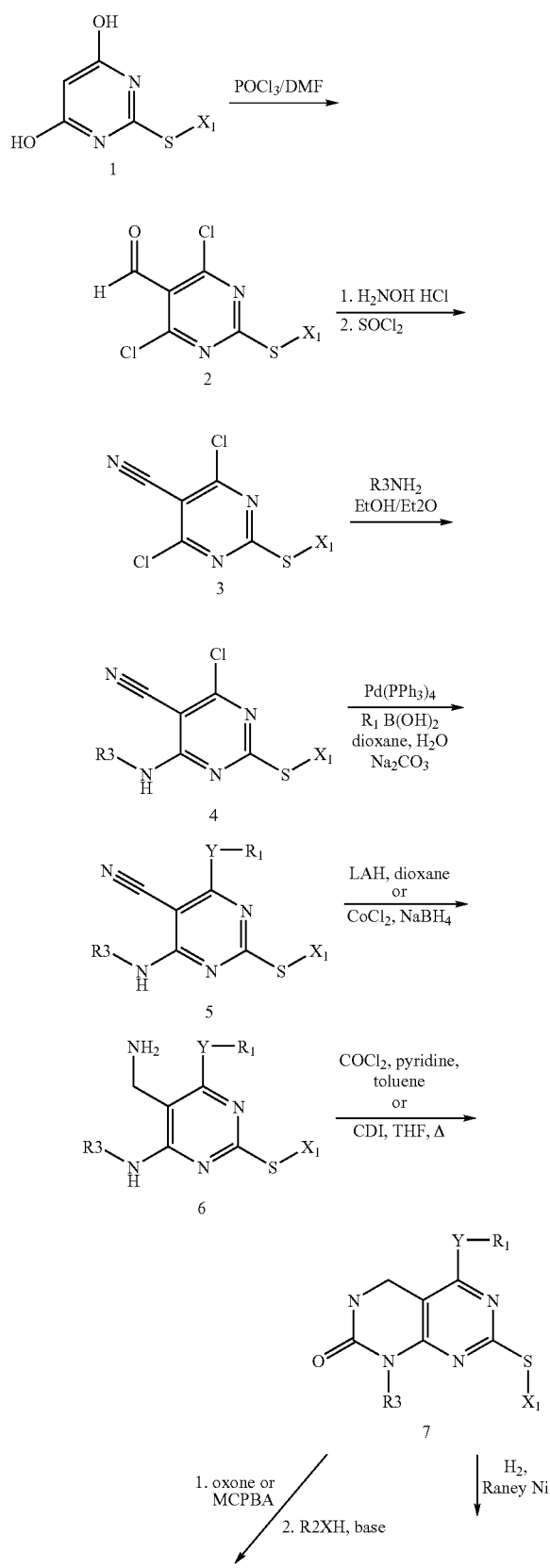

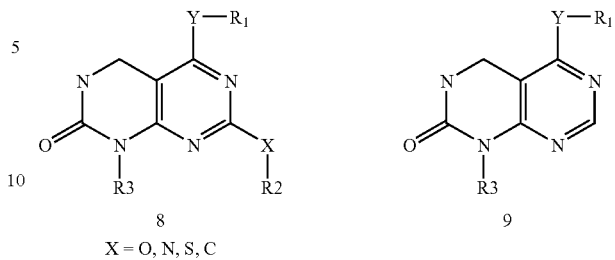

X = O, N, S, C

In Schemes I and II herein, $X_1$ is a $C_{1-10}$ alkyl, aryl, or heteroaryl group, and Y—$R_1$ is as defined for Formula (IV) compounds.

Commercially available 4,6-dihydroxy-2-methylmercaptopyrimidine (1) (which can also be prepared by the literature methods and utilized as described below, with S-alkyl other than S-methyl or S-aryl) was converted to the nitrile (3) by the literature procedure [see Santilli, et al., *J. Heterocycl. Chem.* 1971, 8, 445-453] (Scheme 1). Compound 3 reacts with one equivalent of amine by procedures analogous to those described for related compounds, to afford the 2-methylsulfanyl-4-chloro-6-amino-pyrimidine-5-carbonitrile (4) [See Tumkevicius, S. *Liebigs Ann.* 1995, 1703-1705].

The Suzuki reaction of 4 with aryl boronic acids using a palladium catalyst, such as, tetrakis(triphenylphophine) palladium(0) catalyst proceeds in good to excellent yield. Alternatively, the bi-aryl coupling reaction of (4) can be performed using aryl or heteroaryl organozinc, organcopper, organotin, or other organometallic reagents known to afford bi-aryl cross-coupling products [See for example Solberg, J.; Undheim, K. *Acta Chemica Scandinavia* 1989, 62-68]. Displacement of the chlorine in 4 may also be achieved with nitrogen nucleophiles [For related aminations see U.S. Pat. Nos. 3,631,045 and 3,910,913]. Displacement of the chlorine in 4 is also possible with S nucleophiles, [See Tumkevicius, S. *Liebigs Ann.* 1995, 1703-1705] or O, or alkyl nucleophiles.

The 7-methylsufamyl-1,5-disubstituted-3,4-dihydro-1H-pyrimido[4,5-d]pyrimidin-2-ones (7) are prepared by reduction of the nitriles (5) preferably with a hydride reducing agent, such as lithium aluminum hydride or $NaB_2H_7$ preferably in an ethereal solvent, such as THF, $Et_2O$, glyme or dioxane to produce the di-amine (6). In cases where functionality is incompatible with the more reactive hydride reducing agents, alternative, selective, reduction methods for the nitriles include samarium di-iodide in $H_3PO_4$, Raney Ni catalyzed hydrogenation, or sodium borohydride-cobaltous chloride. The resulting diamines 6 can be cyclized to (7) with carbonyldiimidazole or a mixed anhydride such as ethyl chloroformate, or for less reactive diamines, with phosgene or triphosgene and a suitable tertiary amine base at temperatures between −78° and 100° C.

Oxidation of the sulfides (7) with an oxidant such as one or two equivalents of meta-chloroperoxybenzoic acid or Oxone® affords either the sulfoxides or sulfones. Oxidation of the sulfides to sulfones can also be effected by $OsO_4$ and catalytic tertiary amine N-oxide. Other methods for sulfide oxidation include the use of hydrogen peroxide, other peracids, oxygen, ozone, organic peroxides, potassium and zinc permanganate, potassium persulfate, and sodium hypochlorite.

Both 2-pyrimidininyl sulfones and sulfoxides related to compounds of Formula (IV) wherein X is SO-alkyl or $SO_2$-alkyl have been reported in the literature to be displaced by a wide variety of nucleophiles. Thus the analogs of Formula (IV) compounds wherein X is an alkyl sulfone or sulfoxide may be displaced by primary and secondary alkylamines without additional base catalysis, preferably in a polar aprotic solvent, such as but not limited to, N-methyl pyrrolidin-2-one (NMP), and at varying temperatures depending upon the nucleophilicity of the amine. For instance displacement of the sulfone of analogs of Formula (IV) compounds with ethanolamine, in NMP, occurs in 30 min. at about 65° while a more hindered amine such as Tris(hydroxymethyl)aminomethane requires elevated temperatures and extended reaction times (such as, about 80° and about a 24 hour reaction time). The sulfone may also be displaced with substituted arylamine, or heteroarylamines at elevated temperatures, sometimes requiring formation of the aryl or heteroarylamine anion as with sodium hydride, or other suitable base, in DMSO. In addition, the sulfoxide analogs of Formula (IV) compounds may be readily displaced with aluminum salts of aryl or heteroaryl amines as previously described in the patent literature (WO 9932121).

Likewise, sulfone and sulfoxide analogs of (IV) may be displaced with aryl or heteroaryl or alkyl thiols or alkyl or aryl or heteroaryl alcohols. For instance analogs of IV containing sulfones as the X substituents may be displaced with sodium alkoxide in the alcohol or alternatively reactive alkoxide or phenoxide nucleophiles may be generated from the alcohol or phenol with a suitable base such as NaH or sodium bis-trimethylsilyl amide in a polar aprotic solvent such as DMSO.

Similarly 2-pyrimidinyl sulfones related to (IV) may be displaced with carbon nucleophiles such as aryl or alkyl Grignard reagents or related organometalics such as organo lithium, zinc, tin or boron. These reactions may, in some cases, require transition metal catalysis such as with Pd or Ni catalysts. Displacement of related 2-pyrimidine sulfones with cyanide, malonate anions, unactivated enolates, or heterocyclic C nucleophiles such as 1-methylimidazole anion, by the generation of the anion with NaH or other suitable base in THF also has precedent (see for example, Chem Pharm Bull. 1987, 4972-4976.). For example analogs of (IV) compounds wherein X is an alkyl sulfone may be displaced with the anion of 1-methyl imidazole, generated by treatment of 1-methyl imidazole with n-butyl lithium in a solvent such as THF at temperatures of about −70°, to afford the C-alkylated product substituted on the imidazole C-2.

The 3,4-Dihydro-1H-pyrimido[4,5-d]pyrimidin-2-ones, unsubstituted at the 7 position (9) (Scheme 1) can be obtained by Raney Ni hydrogenolysis of the SMe compound (7) as well as by direct synthesis from the analog of 1 (in Scheme 1) which lacks the S alkyl substituent.

The oxidized series of analogs of Formula (IVa) compounds may be prepared from 5 by partial reduction of the nitrile with a suitable hydride reducing agent such as diisobutylaluminum hydride, preferably at low temperature, and avoiding hydrolytic conditions, to afford the imine (Scheme 2). Cyclization of the imine with phosgene or a less reactive equivalent of phosgene such as carbonyldiimidazole affords 1a (Scheme 2).

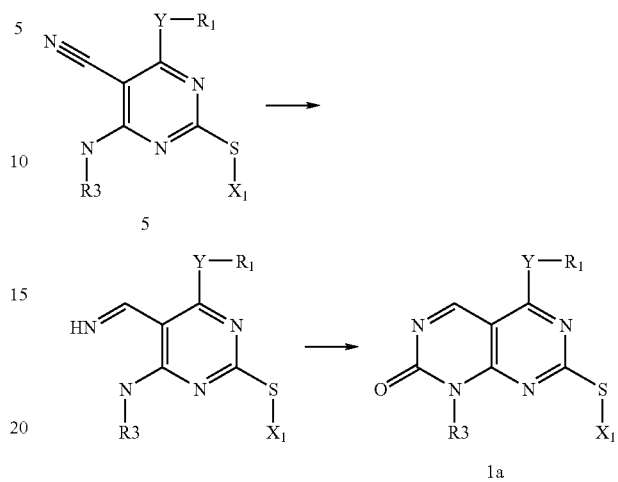

Substitution at the 7 position of the 3,4-dihydro-1H-pyrimido[4,5-d]pyrimidin-2-ones with aryl substituents is also readily achieved by performing the 2-aryl pyrimidines as depicted in Scheme 3 below. While the scheme displays $R_1$ and X as an aryl moiety, it is merely for representation purposes herein.

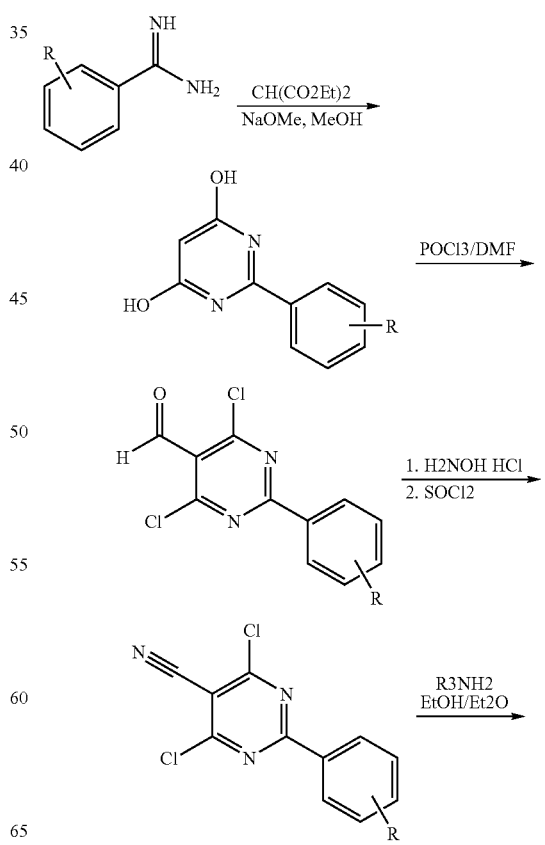

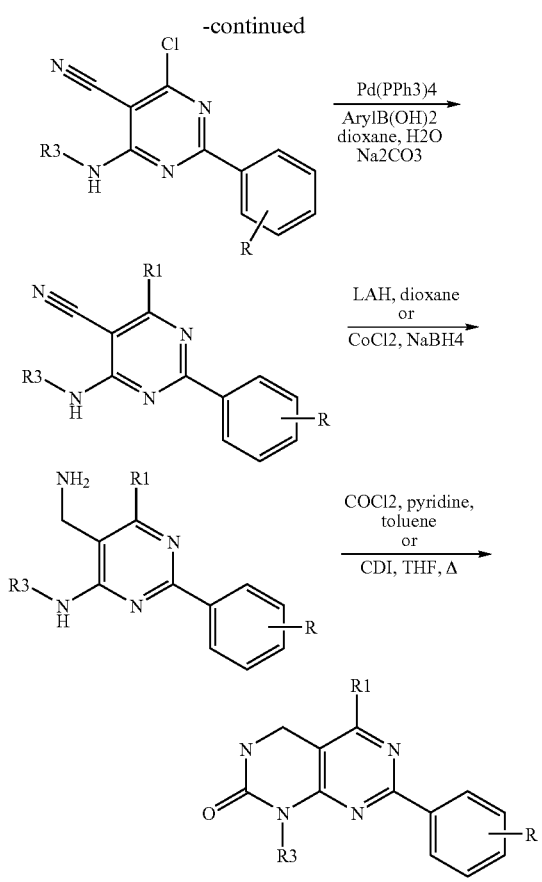

Another aspect of the present invention are the intermediate compounds of Formula (A):

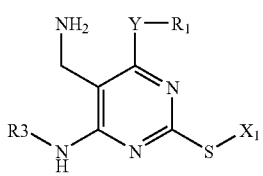

wherein Y—R$_1$ and R$_3$ are as defined herein for Formula (IV); and X$_1$ is a C$_{1-10}$ alkyl, aryl or heteroaryl moiety. Preferably X$_1$ is a C$_{1-10}$ alkyl, more preferably a methyl or propyl.

Another aspect of the present invention are the intermediate compounds of Formula (C):

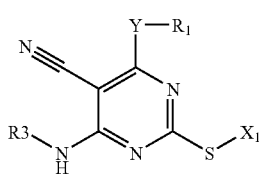

wherein Y—R$_1$ and R$_3$ are as defined herein for Formula (IV); and X$_1$ is a C$_{1-10}$ alkyl, aryl or heteroaryl moiety. Preferably X$_1$ is a C1-10 alkyl, more preferably a methyl or propyl.

Methods of Treatment

The compounds of Formula (I) to (V) and (Ia) to (Va) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages; or by the exacerbation or excessive or unregulated production of the CSBP protein.

For purposes herein, compounds of Formula (I) to (V) and (Ia) to (Va) will all be referred to as compounds of Formula (I) unless otherwise indicated.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cell diseases and Alzheimer's disease.

Use of a CSAID for the treatment of CSBP mediated disease states, can include, but not be limited to neurodegenerative diseases, such as Alzheimer's disease (as noted above), Parkinson's disease and multiple sclerosis, etc.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, chronic pulmonary inflammatory disease and chronic obstructive pulmonary disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al., (1998), Clin. Infec. Dis., Vol 26, p 840; Teren et al., (1997), Am J Respir Crit Care Med vol 155, p 1362; Grunberg et al. (1997), Am J Respir Crit Care Med 156:609 and Zhu et al, J Clin Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac, brain and renal repeRtusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii)

the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-$\beta$). As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-$\beta$ (also known as lymphotoxin) has close structural homology with TNF-$\alpha$ (also known as cachectin) and since each induces similar biologic responses and binds to the same cellular receptor, both TNF-$\alpha$ and TNF-$\beta$ are inhibited by the compounds of the present invention and thus are herein referred to collectively as "TNF" unless specifically delineated otherwise.

A member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, coronary arterial bypass grafting (CABG) surgery, chronic renal failure, angiogenesis & related processes, such as cancer, thrombosis, glomerulonephritis, diabetes and pancreatic $\beta$ cells, multiple sclerosis, muscle degeneration, eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406-1412; Badger, et al., (1989) *Circ. Shock* 27, 51-61; Votta et al., (1994) in vitro. *Bone* 15, 533-538; Lee et al., (1993). *B Ann. N. Y. Acad. Sci.* 696, 149-170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Another aspect of the present invention is a method of treating the common cold or respiratory viral infection caused by human rhinovirus (HRV), other enteroviruses, coronavirus, influenza virus, parainfluenza virus, respiratory syncytial virus, or adenovirus in a human in need thereof which method comprises administering to said human an effective amount of a CBSP/p38 inhibitor.

Another aspect of the present invention is a method of treating, including prophylaxis of influenza induced pneumonia in a human in need thereof which method comprises administering to said human an effective amount of a CBSP/p38 inhibitor The present invention also relates to the use of the CSBP/p38 kinase inhibitor for the treatment, including prophylaxis, of inflammation associated with a viral infection of a human rhinovirus (HRV), other enteroviruses, coronavirus, influenza virus, parainfluenza virus, respiratory syncytial virus, or adenovirus.

In particular, the present invention is directed to the treatment of a viral infection in a human, which is caused by the human rhinovirus (HRV), other enterovirus, coronavirus, influenza virus, parainfluenza virus, respiratory syncytial virus, or an adenovirus. In particular the invention is directed to respiratory viral infections that exacerbate asthma (induced by such infections), chronic bronchitis, chronic obstructive pulmonary disease, otitis media, and sinusitis. While inhibiting IL-8 or other cytokines may be beneficial in treating a rhinovirus may be known, the use of an inhibitor of the p38 kinase for treating HRV or other respiratory viral infections causing the common cold is believed novel.

It should be noted that the respiratory viral infection treated herein may also be associated with a secondary bacterial infection, such as otitis media, sinusitis, or pneumonia.

For use herein treatment may include prophylaxis for use in a treatment group susceptible to such infections. It may also include reducing the symptoms of, ameliorating the symptoms of, reducing the severity of, reducing the incidence of, or any other change in the condition of the patient, which improves the therapeutic outcome.

It should be noted that the treatment herein is not directed to the elimination or treatment of the viral organism itself but is directed to treatment of the respiratory viral infection that exacerbates other diseases or symptoms of disease, such as asthma (induced by such infections), chronic bronchitis, chronic obstructive pulmonary disease, otitis media, and sinusitis.

A preferred virus for treatment herein is the human rhinovirus infection (HRV) or respiratory syncytial virus (RSV).

Another aspect of the present invention is directed to the treatment of inhaled smoke induced airway inflammation, lung chemokine production and cytokine production. The invention may be directed to treatment of the airway induced inflammation which is secondary to other respiratory disorders such as viral infections that exacerbate asthma (induced by such infections), chronic bronchitis, chronic obstructive pulmonary disease, otitis media, and sinusitis. A respiratory viral infection treated in conjunction with the smoke related airway inflammation may also be associated with a secondary bacterial infection, such as otitis media, sinusitis, or pneumonia.

It is noted that the inflammation may be due to cytokines and chemokine release from neutrophile activation and other leukocytes, as well as vascular and airway endothelial cell activation.

For use herein treatment may include prophylaxis for use in a treatment group who may be susceptible to such airway inflammation. It may also include reducing the symptoms of, ameliorating the symptoms of, reducing the severity of, reducing the incidence of, or any other change in the condition of the patient, which improves the therapeutic outcome.

Suitable patient populations for whom this may be prophylactically beneficial could be firemen who routinely inhale smoke in the course of their duties; use in the military, and by civilians in wartime exposure.

As noted, smoke of natural causes, such as plant extracts, natural plants products, synthetic material, chemically treated natural materials, or natural products such as oil and gas or other fossil fuels, may be treated within the scope of this invention. Suitably, the treatment including prophylaxis is related to cigarette smoke or synthetic/composites, such as occur in fires associated with burning buildings or homes.

Another aspect of the present invention relates to the use of a CSBP/p38 kinase inhibitor for the treatment, including prophylaxis, of the hypertussive activity associated with resulting airway inflammation and/or cough in a mammal in need thereof.

The present invention also relates to use of a CSBP/p38 kinase inhibitor for the treatment, including prophylaxis, of the inflammation enhanced cough related disorders in a mammal in need thereof.

The present invention is also directed to the use of a compound of Formula (I) in eosinophilic bronchitis, and in cough variant asthma.

The compounds of Formula (I) may also be used in the treatment, including prophylaxis, of eosinophilic inflammation in the airways and cough. Treatment, including prophylaxis is appropriate for eosinophilic bronchitis (as this differs from asthma) and for the treatment, including prophylaxis of cough variant asthma. These disorders may be directed to treatment of the airway induced inflammation which is secondary to other respiratory disorders such as viral infections that exacerbate asthma (induced by such infections), chronic bronchitis, chronic obstructive pulmonary disease, otitis media, and sinusitis. A respiratory viral infection treated in conjunction with the smoke related airway inflammation may also be associated with a secondary bacterial infection, such as otitis media, sinusitis, or pneumonia.

The hypertussive or inflammation enhanced cough related disorders may either be a direct result of or an association with eosinophilia activity. It may also be a result of, or associated with the blocking production of certain cytokines which may mediate these phenomena.

For use herein treatment may include prophylaxis for use in a treatment group who may be susceptible to such airway inflammation, and/or cough. It may also include reducing the symptoms of, ameliorating the symptoms of, reducing the severity of, reducing the incidence of, or any other change in the condition of the patient, which improves the therapeutic outcome.

Clinically, eosinophilic bronchitis presents as chronic cough and sputum eosinophilia, but without the abnormalities of airway function seen in asthma. In contrast to cough in patients without sputum eosinophilia, the cough responds to anti-inflammatory therapy, such as inhaled corticosteroids (Niimi et al., Eosinophilic inflammation in cough variant asthma, European Respiratory Journal. 11(5): 1064-9, (1998)).

Patients with cough-variant asthma may also have the following criteria: (1) have not been previously diagnosed as having asthma; (2) complain of a cough of at least a 3-week duration; (3) do not complain of wheezing, shortness of breath, or chest tightness; (4) have normal results of physical examinations; (5) have normal or nearly normal results of spirometry; (6) have evidence of bronchial hyperresponsiveness during bronchoprovocation challenge testing; and (7) have a favorable response to asthma medications (Irwin et al., Interpretation of positive results of a methacholine inhalation challenge and 1 week of inhaled bronchodilator use in diagnosing and treating cough-variant asthma (Archives of Internal Medicine. 157(17):1981-1987, (1997)).

Unlike conventional anti-tussive agents, such as codeine or dextromethorphan, a p38 kinase inhibitor appears to have no direct antitussive activity, but reduces the airway eosinophilia and normalizes the hypertussive state. Therefore, use of a p38 inhibitor will reduce the added coughs, or hypertussive state, back to a normal level which can be suitably treated with conventional agents and/or therapies as appropriate. Use of the p38 inhibitors will allow for the maintenance of patients who are subject to increased cough responsiveness, especially unproductive cough, due to other underlying disorders or treatments. This increased cough responsiveness may be modulated, or decreased by use of this innovative anti-inflammatory therapy.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be “acceptable” in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, $H_2O$ and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The invention will now be described by reference to the following biological examples which are merely illustrative and are not to be construed as a limitation of the scope of the present invention.

BIOLOGICAL EXAMPLES

The cytokine-inhibiting effects of compounds of the present invention may be determined by the following in vitro assays:

Assays for Interleukin-1 (IL-1), Interleukin-8 (IL-8), and Tumour Necrosis Factor (TNF) are well known in the art, and may be found in a number of publications, and patents. Representative suitable assays for use herein are described in Adams et al., U.S. Pat. No. 5,593,992, whose disclosure is incorporated by reference in its entirety.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1 \times 10^6$) are plated in 24-well plates at a concentration of 1-2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. Immuno Therapy, 6 (1), 1-12 (1990) (ELISA assay).

In Vivo TNF Assay:

(1) Griswold et al., *Drugs Under Exp. and Clinical Res., XIX* (6), 243-248 (1993); or (2) Boehm, et al., *Journal Of Medicinal Chemistry* 39, 3929-3937 (1996) whose disclosures are incorporated by reference herein in their entirety.

LPS-Induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 min) with compound or vehicle. After the 30 min. pretreat time, the mice are given LPS (lipopolysaccharide from *Esherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 min after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301-306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 min in a TOMY microfuge, plasma was withdrawn and frozen at −80 C.

Cytokine measurement: IL-1 and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP/p38 Kinase Assay:

This assay measures the CSBP/p38-catalyzed transfer of $^{32}$P from [a-$^{32}$P]ATP to threonine residue in an epidermal growth factor receptor (EGFR)-derived peptide (T669) with the following sequence: KRELVEPLTPSGEAPNQALLR (SEQ ID 1) (residues 661-681). (See Gallagher et al., "Regulation of Stress Induced Cytokine Production by Pyridinyl Imidazoles: Inhibition of CSBP Kinase", BioOrganic & Medicinal Chemistry, 1997, 5, 49-64).

Reactions were carried in round bottom 96 well plate (from Corning) in a 30 ml volume. Reactions contained (in final concentration): 25 mM Hepes, pH 7.5; 8 mM MgCl$_2$; 0.17 mM ATP (the KM$_{[ATP]}$ of p38 (see Lee et al., Nature 300, n72 pg. 639-746 (December 1994)); 2.5 uCi of [g-32P]ATP; 0.2 mM sodium orthovanadate; 1 mM DTT; 0.1% BSA; 10% glycerol; 0.67 mM T669 peptide; and 2-4 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 min prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400-450 pmol/pmol enzyme, and the activity was linear for up to 2 hours of incubation. The kinase activity values were obtained after subtracting values generated in the absence of substrate which were 10-15% of total values.

Representative compounds of Formula (I), Examples 1 to 167 have demonstrated positive inhibitory activity in this assay, all having of IC$_{50's}$ of <100 uM in this binding assay.

TNF-α in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

Cigarette Smoke Exposure Model

A murine model of cigarette smoke inhalation was developed to explore a relationship to leukocyte trafficking and lung chemokine and cytokine production. Balb/c mice are exposed to smoke generated from commercial unfiltered cigarettes for a specified period of time and samples are obtained at varying times during the post-exposure. This model is demonstrated in greater detail as shown below, in contrast to other smoke extract models known in the art.

A model of cigarette smoke exposure in the mouse is established in which mice are placed 6 at a time into a small animal plexiglass dosing chamber attached to a peristaltic pump whose intake is connected to a holder for a commercial unfiltered cigarette (Lucky Strike™). Along with fresh air, smoke is delivered into the chamber until the cigarette is consumed (approximately 5 minutes). Varying numbers of cigarettes (2-4 per day, 2-3 hr apart) are utilized for 1-3 consecutive days. Animals are euthanized by pentobarbital overdose approximately 18 hours after the final exposure. Bronchoalveolar lavage with phosphate-buffered saline is performed for inflammatory cell enumeration, and BAL aliquots and lungs are frozen for cytokine analysis. Smoke exposure results in time- and cigarette number-related increases in airway neutrophils, and lung chemokine (KC) and cytokine (IL-6) content.

To evaluate the role of a p38 MAP kinase inhibitor in this inflammatory response, mice are treated with a p38 kinase inhibitor, a compound of Formula (I) at approximately a 30 mg/kg, p.o. b.i.d. Reduction in lung KC (a murine homologue of IL-8) levels are assessed 1 day after exposure (prior to neutrophilia), and attenuated airway neutrophilia and lung IL-6 levels are assessed following 3 days of cigarette exposure.

Hypertussive Cough Models

Described below is an example of how to determine the usefulness of p38 inhibitors in the treatment of hypertussive disorders or inflammation enhanced cough.

Figure 2:
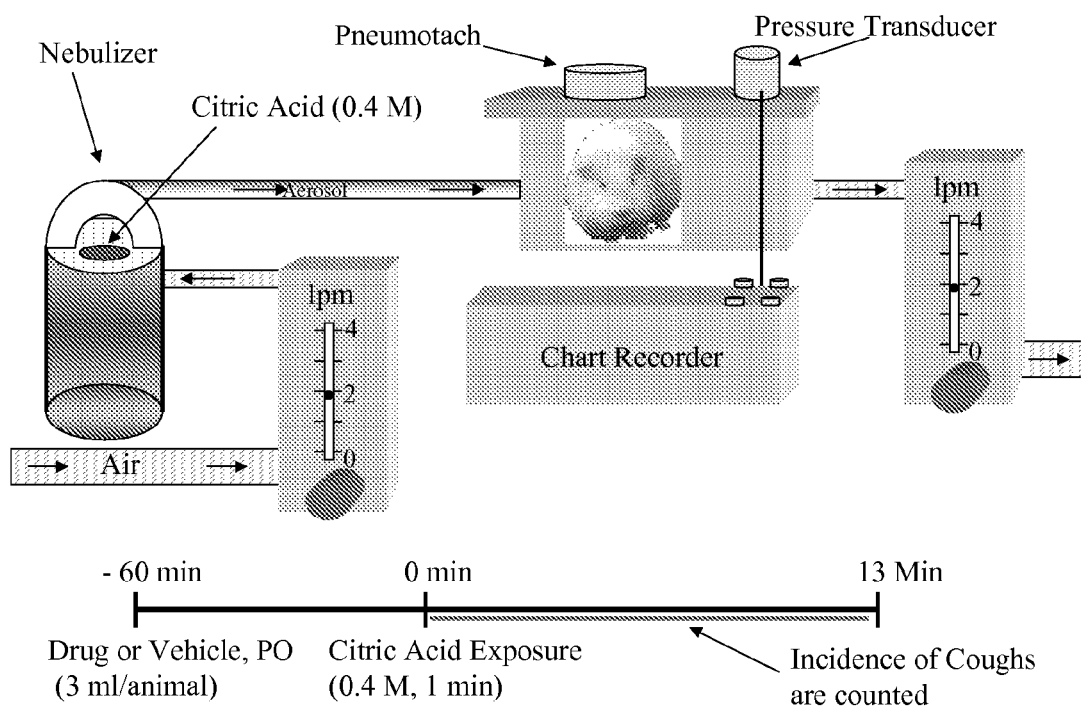
FIG. 2 demonstrates a Citric Acid Induced Cough Model.

The directed antitussive activity of the compound in question if first assessed, by a 10 to 30 minute pretreatment period by intraperitoneal injection or a 1 hour pretreatment period for oral administration. The animals (guinea pigs) are then subjected to an inhaled citric acid-induced cough challenge. The Citric Acid Induced Cough Model is shown in FIG. 2.

Figure 3:
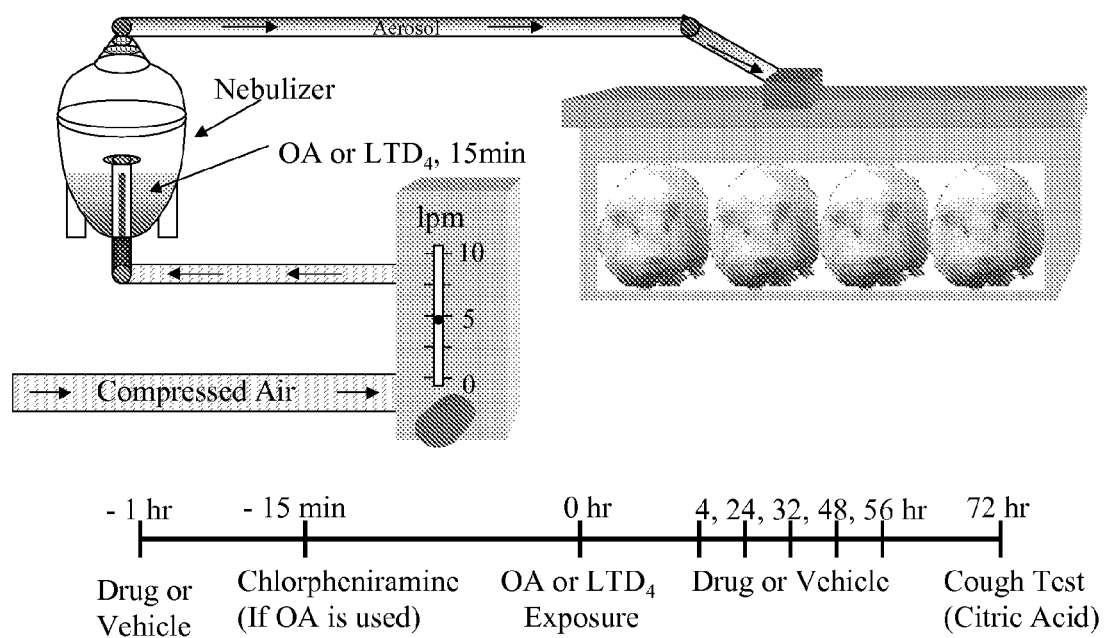
FIG. 3 demonstrates an Antigen- or LTD4-Induced Hypertussive Model in the Guinea Pig
FIG. 4 demonstrates Effects of Dextromethorphan or Codeine On Citric Acid-Induced Cough in Guinea Pigs.

The effects of the compound are then assessed on the hypertussive response that occurs 72 hours post aerosol exposure to antigen or LTD4 exposure. Treatment of the animals occurs with the drug prior and/or after antigen or LTD4 challenge, but not on the day of citric acid challenge. The antigen or LTD4 induced hypertussive model is shown in FIG. 3.

Figure 4:
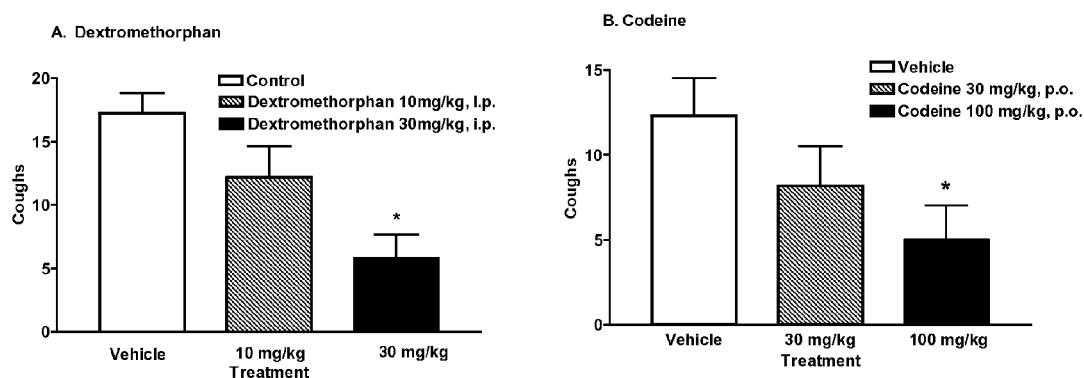

The effects of known antitussive agents, dextromethorphan and codeine on Citric Acid Induced Cough in Guinea Pigs is shown in FIG. 4.

Inhalation of citric acid (CA; 0.4% for 1 minute) induces 11 to 15 coughs during the exposure and 12-minute monitoring period in conscious guinea pigs. Exposure of sensitized animals to inhaled ovalbumin resulted in a hypertussive state (50-80% increase in CA-induced cough incidence) for several days, which positively correlated with airway eosinophilia determined by bronchoalveolar lavage.

Similarly, inhalation of LTD4 (10 ug/ml for 1 minute) increases cough incidence and airway esoinophils 72 hours after exposure. Further explanation and details may be found in PCT/US00/25386, filed 15 Sep. 2000 whose disclosure is incorporated by reference in its entirety.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere where necessary.

Mass spectra were run on an open access LC-MS system using electrospray ionization. LC conditions: 4.5% to 90% $CH_3CN$ (0.02% TFA) in 3.2 min with a 0.4 min hold and 1.4 min re-equilibration; detection by MS, UV at 214, and a light scattering detector (ELS). Column: 1×40 mm Aquasil (C18) $^1$H-NMR (hereinafter "NMR") spectra were recorded at 400 MHz using a Bruker AM 400 spectrometer or a Bruker AVANCE 400. Multiplicities indicated are: s=singlet, d=doublet, t=triplet, q=quartet, m=multiplet and br indicates a broad signal. Preparative (prep) hplc; ca 50 mg of the final products were injected in 500 uL of DMSO onto a 50×20 mm I. D. YMC CombiPrep ODS-A column at 20 mL/min with a 10 min gradient from 10% $CH_3CN$ (0.1% TFA) to 90% $CH_3CN$ (0.1% TFA) in $H_2O$ (0.1% TFA) and a 2 min hold. Flash chromatography is run over Merck Silica gel 60 (230-400 mesh).

Accepted abbreviations are used as described in the ACS Style Guide (*The ACS Style Guide. A Manual for Authors*; Dodd, J. A., Ed.; American Chemical Society: Washington, D.C., 1986; pp 47-69.). In addition the following are used:

| | |
|---|---|
| BOC | t-butoxycarbonyl |
| eq | indicates the proportion of molar equivalents of a reagent relative to the principal reagent |
| NMP | 1-methyl-2-pyrrolidinone |
| satd | saturated |
| Rt | hplc retention time |

Example 1

Preparation of 1,5-diphenyl-7-methylsulfanyl-3,4-dihydro-1H-pyrimido[4,5-d]pyrimidin-2-one a) 4-Chloro-2-methylsulfanyl-6-phenylamino-pyrimidine-5-carbonitrile 4,6-Dichloro-2-methylsulfanyl-pyrimidine-5-carbonitrile [Santilli, et al., *J. Heterocycl. Chem.* 1971, 8, 445-453] (0.222 grams (hereinafter "g"), 1.0 millimoles (hereinafter "mmol")) in EtOH (2 milliliters (hereinafter "mL")) and $Et_2O$ (1 mL) was treated with aniline (184 microliter (hereinafter "uL"), 2.0 mmol) in EtOH (1 mL). A clear solution formed initially but rapidly formed a heavy precipitate. The mixture was stirred 30 minutes (hereinafter "min") and was filtered, and the solid was washed with 1:1 $Et_2O$, EtOH and then $Et_2O$, dried to afford 162 milligrams (hereinafter "mg") (59%) of the title compound as a white solid. LC MS m/e=277 (MH+), Rt=2.32 min.

b) 2-Methylsulfanyl-4-phenyl-6-phenylamino-pyrimidine-5-carbonitrile

The product of the previous example, (162 mg, 0.59 mmol), phenylboronic acid (360 mg, 2.95 mmol), $Na_2CO_3$ (318 mg, 3 mmol), dioxane (3 mL) and $H_2O$ (1.5 mL) were combined and argon was bubbled through the mixture for 30 min $Pd[P(Ph)_3]$ (15 mg, 0.013 mmol) was added and the mixture was heated to 85° for 1.5 h, then cooled, diluted with $H_2O$ (25 mL) and extracted with EtOAc (6×50 mL). The combined extracts were washed with $H_2O$, dried ($Na_2SO_4$), concentrated and filtered through a 10 g plug of silica (Varien bond Elute®) with $CH_2Cl_2$ to afford the title compound as a white solid 185 mg (97%). LC MS m/e=319 (MH+), Rt=2.59 min.

c) (5-Aminomethyl-2-methylsulfanyl-6-phenyl-pyrimidin-4-yl)-phenylamine

The product of the previous example (151 mg, 0.47 mmol) was dissolved in warm dioxane (6 mL), cooled to 23° and 1M LAH in $Et_2O$ (1 mL, 1 mmol) was added and the resulting solution was heated to 55° for 1.5 h., diluted with EtOAc (10 mL) and then poured into 10% aq NaOH (20 mL) and extracted with more EtOAc (2×50 mL). The combined EtOAc was washed with $H_2O$, then satd aq NaCl, dried ($Na_2SO_4$) and concentrated to afford the title compound as a yellow solid. 153 mg (100%). LC MS m/e=323 (MH+), Rt=1.49 min d) 1,5-diphenyl-7-methylsulfanyl-3,4-dihydro-1H-pyrimido[4,5-d]pyrimidin-2-one The product of the previous example (4.0 g, 12.8 mmol), 2-methyl-4-fluorophenylboronic acid (Lancaster) (5.91 g, 38.4 mmol), $Na_2CO_3$ (4.04 g, 38.4 mmol), dioxane (100 mL) and $H_2O$ (50 mL) were combined and a stream of argon was passed through the mixture for 15 min $Pd[P(Ph)_3]_4$ (Aldrich) (400 mg) was added and the mixture was heated to 85° for 6 h. EtOAc (600 mL) was added and the organic phase was washed with $H_2O$ (100 mL). The aq wash was extracted with EtOAc (2×75 mL) and the combined organic phases were washed with more $H_2O$ (50 mL) and satd aq NaCl (50 mL), dried ($Na_2SO_4$), concentrated and the residue was flash chromatographed with $CH_2Cl_2$. The desired fractions were pooled and concentrated in vacuo to afford 4.16 g (84%) of a tan foam. LC MS m/z=387 (MH$^+$), Rt=2.52 min e) 5-Aminomethyl-6-(4-fluoro-2-methylphenyl)-2-methylsulfanylpyrimidin-4-yl-(2,6-difluorophenyl)amine Example 2

1-(2,6-difluorophenyl)-5-(4-fluoro-2-methylphenyl)-7-methylsulfanyl-3,4-dihydro-1H-pyrimido[4,5-d]pyrimidin-2-one a) 4-Chloro-6-(2,6-difluoro-phenylamino)-2-methylsulfanyl-pyrimidine-5-carbonitrile 2,6-di-Fluoroaniline (2.66 mL, 24 mmol), DMSO (12 mL) and NaH (0.912 g, 22.8 mmol) were combined at 23°. When the foaming ceased 4,6-Dichloro-2-methylsulfanyl-pyrimidine-5-carbonitrile [Santilli, et al., *J. Heterocycl. Chem.* 1971, 8, 445-453] (5.0 g, 22.82 mmol) was added in DMSO (12 mL). The reaction exothermed and the temperature was moderated with cold $H_2O$ bath, then stirred at 23° for 3 h. The reaction was diluted with EtOAc (300 mL) and washed with H₂O (4×) and satd aq NaCl (1×). Dried (Na₂SO₄) and concentrated to afford 6.21 g (82%) of a tan foam. LC MS m/z=313 (MH⁺), Rt=2.37 min.

b) 4-(2,6-Difluorophenylamino)-6-(4-fluoro-2-methylphenyl)-2-methylsulfanylpyrimidine-5-carbonitrile The product of the previous example (4.0 g, 12.8 mmol), 2-methyl-4-fluorophenylboronic acid (Lancaster) (5.91 g, 38.4 mmol), Na₂CO₃ (4.04 g, 38.4 mmol), dioxane (100 mL) and H₂O (50 mL) were combined and a stream of argon was passed through the mixture for 15 min. Pd[P(Ph)₃]₄ (Aldrich) (400 mg) was added and the mixture was heated to 85° for 6 h. EtOAc (600 mL) was added and the organic phase was washed with H₂O (100 mL). The aq wash was extracted with EtOAc (2×75 mL) and the combined organic phases were washed with more H₂O (50 mL) and satd aq NaCl (50 mL), dried (Na₂SO₄), concentrated and the residue was flash chromatographed with CH₂Cl₂. The desired fractions were pooled and concentrated in vacuo to afford 4.16 g (84%) of a tan foam. LC MS m/z=387 (MH⁺), Rt=2.52 min c) 5-Aminomethyl-6-(4-fluoro-2-methylphenyl)-2-methylsulfanylpyrimidin-4-yl]-(2,6-difluorophenyl) amine The product of the previous example (4.24 g, 11.0 mmol) was dissolved in Et₂O (200 mL) and 1M LAH in Et₂O (22 mL) was added dropwise. After addition the mixture was heated to Et₂O reflux for 1.5 h, cooled to 4° and quenched by the addition of H₂O (1.1 mL), then 10% aq NaOH (5.5 mL) and then more H₂O (5.5 mL), stirred 10 min then 2.5% CH₃OH in CH₂Cl₂ (400 mL) was added. Stirred 15 min and the organic layer was decanted and the residue was washed with additional 2.5% methanolic CH₂Cl₂ (200 mL). The combined organic layers were dried (Na₂SO₂) and concentrated to afford 4.02 g (94%) of a yellow foamy solid. LC MS m/z=391 (MH⁺), Rt=1.62 min.

d) 1-(2,6-difluorophenyl)-5-(4-fluoro-2-methylphenyl)-7-methylsulfanyl-3,4-dihydro-1H-pyrimido[4,5-d]pyrimidin-2-one The product of the previous example, (4.02 g, 10.4 mmol) was dissolved in THF (100 mL) and carbonyldiimidazole (2.23 g, 13.8 mmol) was added. The resulting mixture was stirred 16 h, diluted with EtOAc (1 L) and washed with H₂O (4×150 mL) and satd aq NaCl (150 mL), dried (Na₂SO₄) and concentrated to a brown foam. The residue was dissolved in CH₂Cl₂ and flash chromatographed in 0-2% CH₃OH in CH₂Cl₂ to afford 2.97 g (69%) of the title compound as an off white solid. LC MS m/z=417 (MH⁺), Rt=2.27 min.

Example 3

1-(2,6-difluorophenyl)-5-(4-fluoro-2-methylphenyl)-7-methylsulfonyl-3,4-dihydro-1H-pyrimido[4,5-d]pyrimidin-2-one The product of the preceeding example, example 2 (2.14 g, 5.14 mmol), CH₂Cl₂ (100 mL) and meta-chloroperoxybenzoic acid (57-85%) (3.102 g, 10.26 mmol if 57%) were dissolved together. After 16 h, the reaction was diluted with EtOAc (300 mL) and washed with 5% aq Na₂CO₃ (6×50 mL), H₂O (50 mL) and satd aq NaCl (50 mL), dried Na₂SO₂ and concentrated to afford 2.3 g (100%) of the title compound as a white solid. LC MS m/z=417 (MH⁺), Rt=1.94 min Example 4

1-(2,6-difluorophenyl)-5-(4-fluoro-2-methylphenyl)-7-(piperidin-4-ylamino)-3,4-dihydro-1H-pyrimido[4,5-d]pyrimidin-2-one trifluoroacetate a) 1-(2,6-difluorophenyl)-5-(4-fluoro-2-methylphenyl)-7-(1-tert-butoxycarbonyl-piperidin-4-ylamino)-3,4-dihydro-pyrimido[4,5-d]pyrimidin-2-one The product of the previous example, Example 3 (90 mg, 0.2 mmol), NMP (1 mL) and 4-amino-1-BOC-piperidine (Astatech) (200 mg, 1.0 mmol) were heated in an oil bath at 65° for 16 h. The reaction was cooled to 23°, diluted with EtOAc (75 mL) and washed with 10% aq citric acid (2×), H₂O and satd aq NaCL, dried (Na₂SO₄), and concentrated to afford 112 mg of a white solid. LC MS m/z=569 (MH⁺), Rt=2.14 min b) 1-(2,6-difluorophenyl)-5-(4-fluoro-2-methylphenyl)-7-(piperidin-4-ylamino)-3,4-dihydro-1H-pyrimido[4,5-d]pyrimidin-2-one trifluoroacetate The product of the preceding example was dissolved in TFA (5 mL) and allowed to stand for 15 min, then concentrated and purified by prep hplc to afford 56.8 mg (61%) of a white powder. LC MS m/z=469 (MH⁺), Rt=1.35 min Example 5

1-(2,6-difluorophenyl)-5-(4-fluoro-2-methylphenyl)-7-(2-dimethylaminoethylamino)-3,4-dihydro-1H-pyrimido[4,5-d]pyrimidin-2-one trifluoroacetate The product of example 3 (90 mg, 0.2 mmol) was dissolved in NMP (1 mL) and dimethylaminoethylamine (110 uL, 1.0 mmol) was added and the resulting brown soln was stirred on an oil bath heated to 65° for 16 h., diluted with EtOAc (75 mL) and washed with H₂O (3×) and satd aq NaCl, dried (Na₂SO₄) concentrated and purified by prep hplc to afford 68 mg (75%). LC MS m/z=457 (MH⁺), Rt=1.39 min Example 6

1-(2,6-difluorophenyl)-5-(4-fluoro-2-methylphenyl)-7-(1,3-dihydroxyprop-2-ylamino)-3,4-dihydro-1H-pyrimido[4,5-d]pyrimidin-2-one The product of example 3 (90 mg, 0.2 mmol) was dissolved in NMP (1 mL) and serinol (91 mg, 1.0 mmol) was added. The solution was heated to 65° for 48 h, diluted with EtOAc (75 mL) and washed with 10% aq citric acid (2×), H₂O, and satd aq NaCl, dried (Na₂SO₄), concentrated and purified by prep hplc to afford 46 mg (50%). LC MS m/z=460 (MH⁺), Rt=1.37 min The compounds in Table 1 were prepared by either the method of Example 5 (method A) or by the method of Example 6 (method B), using the appropriate amine. Note that Methods A and B differ by the absence (method A) or presence (method B) of an aqueous citric acid wash during work-up. For those examples where the reaction time and/or temperature was varied from those given in Examples 5 and 6, the changes are indicated in Table 1, below.

TABLE 1

| Example | Compound name | Method (variations) | LC MS m/z | Rt min |
|---|---|---|---|---|
| 7 | 1-(2,6-difluorophenyl)-5-(4-fluoro-2-methylphenyl)-7-(1-methylpiperazin-4-yl)-3,4-dihydro-1H-pyrimido[4,5-d]pyrimidin-2-one trifluoroacetate | A | 469 | 1.49 |
| 8 | 1-(2,6-difluorophenyl)-5-(4-fluoro-2-methylphenyl)-7-(imidazol-1yl-)-3,4-dihydro-1H-pyrimido[4,5-d]pyrimidin-2-one trifluoroacetate | A (5 h) | 437 | 1.64 |
| 9 | 1-(2,6-difluorophenyl)-5-(4-fluoro-2-methylphenyl)-7-([2-hydroxyethyl)-methylamino]-3,4-dihydro-1H-pyrimido[4,5-d]pyrimidin-2-one | B (2 h) | 444 | 1.65 |
| 10 | 1-(2,6-Difluorophenyl)-5-(4-fluoro-2-methylphenyl)-7-(4-hydroxypiperdin-1-yl)-3,4-dihydro-1H-pyrimido[4,5-d]pyrimidin-2-one | B (4 h) | 470 | 1.79 |
| 11 | 1-(2,6-difluorophenyl)-5-(4-fluoro-2-methylphenyl)-7-(4-carboethoxypiperidin-1-yl)-3,4-dihydro-1H-pyrimido[4,5-d]pyrimidin-2-one | B (1 h) | 526 | 2.42 |
| 12 | 1-(2,6-Difluorophenyl)-5-(4-fluoro-2-methylphenyl)-7-(4-hydroxymethylpiperdin-1-yl)-3,4-dihydro-1H-pyrimido[4,5-d]pyrimidin-2-one | B (1 h) | 484 | 2.49 |
| 13 | 1-(2,6-difluorophenyl)-5-(4-fluoro-2-methylphenyl)-7-di(ethan-2-ol-)amino-3,4-dihydro-1H-pyrimido[4,5-d]pyrimidin-2-one | B (24 H) | 474 | 1.55 |
| 14 | 1-(2,6-difluorophenyl)-5-(4-fluoro-2-methylphenyl)-7-(1-methylpiperidin-4-yl-amino)-3,4-dihydro-1H-pyrimido[4,5-d]pyrimidin-2-one trifluoroacetate | A | 483 | 1.37 |
| 15 | 1-(2,6-difluorophenyl)-5-(4-fluoro-2-methylphenyl)-7-(1-morpholin-4-yl)-3,4-dihydro-1H-pyrimido[4,5-d]pyrimidin-2-one | B (16 h) | 456 | 2.12 |
| 16 | 1-(2,6-difluorophenyl)-5-(4-fluoro-2-methylphenyl)-7-(2-morpholin-4-yl ethylamino)-3,4-dihydro-1H-pyrimido[4,5-d]pyrimidin-2-one trifluoroacetate | A | 499 | 1.40 |
| 17 | 1-(2,6-difluorophenyl)-5-(4-fluoro-2-methylphenyl)-7-(2-pyrrolidin-1-yl ethylamino)-3,4-dihydro-1H-pyrimido[4,5-d]pyrimidin-2-one trifluoroacetate | A | 483 | 1.50 |
| 18 | 1-(2,6-difluorophenyl)-5-(4-fluoro-2-methylphenyl)-7-(2-piperidin-1-yl ethylamino)-3,4-dihydro-1H-pyrimido[4,5-d]pyrimidin-2-one trifluoroacetate | A | 497 | 1.55 |
| 19 | 1-(2,6-difluorophenyl)-5-(4-fluoro-2-methylphenyl)-7-(2-pyridin-3-yl ethylamino)-3,4-dihydro-1H-pyrimido[4,5-d]pyrimidin-2-one trifluoroacetate | A | 491 | 1.47 |
| 20 | 1-(2,6-difluorophenyl)-5-(4-fluoro-2-methylphenyl)-7-(2-diethylamino ethylamino)-3,4-dihydro-1H-pyrimido[4,5-d]pyrimidin-2-one trifluoroacetate | A | 485 | 1.55 |
| 21 | 1-(2,6-difluorophenyl)-5-(4-fluoro-2-methylphenyl)-7-(2-pyridin-3-yl ethylamino)-3,4-dihydro-1H-pyrimido[4,5-d]pyrimidin-2-one trifluoroacetate | A | 491 | 1.47 |
| 22 | 1-(2,6-difluorophenyl)-5-(4-fluoro-2-methylphenyl)-7-(2-dimethylamino)-3,4-dihydro-1H-pyrimido[4,5-d]pyrimidin-2-one trifluoroacetate | A[1] | 414 | 1.97 |
| 23 | 1-(2,6-difluorophenyl)-5-(4-fluoro-2-methylphenyl)-7-(2-methylamino)-3,4-dihydro-1H-pyrimido[4,5-d]pyrimidin-2-one trifluoroacetate | A[2] | 400 | 1.64 |
| 24 | 1-(2,6-difluorophenyl)-5-(4-fluoro-2-methylphenyl)-7-(2-methyl-1,3-dihydroxyprop-2-ylamino)-3,4-dihydro-1H-pyrimido[4,5d]pyrimidin-2-one | B (80°, 24 h) | 474 | 1.45 |
| 25 | 1-(2,6-difluorophenyl)-5-(4-fluoro-2-methylphenyl)-7-((R)-2-hydroxy-1-methyl-ethylamino)-3,4-dihydro-1H-pyrimido[4,5-d]pyrimidin-2-one | B (2 h) | 444 | 1.55 |

TABLE 1-continued

| Example | Compound name | Method (variations) | LC MS m/z | Rt min |
|---|---|---|---|---|
| 26 | 1-(2,6-difluorophenyl)-5-(4-fluoro-2-methylphenyl)-7-((S)-2-hydroxy-1-methyl-ethylamino)-3,4-dihydro-1H-pyrimido[4,5-d]pyrimidin-2-one | B (2 h) | 444 | 1.55 |
| 27 | 1-(2,6-difluorophenyl)-5-(4-fluoro-2-methylphenyl)-7-(2-hydroxy-1,1-dimethyl-ethylamino)-3,4-dihydro-1H-pyrimido[4,5-d]pyrimidin-2-one | B (80°, 4 h) | 458 | 1.57 |
| 28 | 1-(2,6-difluorophenyl)-5-(4-fluoro-2-methylphenyl)-7-(2-hydroxy-1,1-bis-hydroxymethyl-ethylamino)-3,4-dihydro-1H-pyrimido[4,5-d]pyrimidin-2-one | B (85°, 16 h) | 490 | 1.19 |
| 29 | 1-(2,6-difluorophenyl)-5-(4-fluoro-2-methylphenyl)-7-(2-hydroxyethylamino)-3,4-dihydro-1H-pyrimido[4,5-d]pyrimidin-2-one | B (0.5 h) | 430 | 1.50 |
| 30 | 1-(2,6-difluorophenyl)-5-(4-fluoro-2-methylphenyl)-7-(2,3-dihydroxypropylamino)-3,4-dihydro-1H-pyrimido[4,5-d]pyrimidin-2-one | B (16 h) | 460 | 1.32 |

[1]Using 40% aq dimethylamine.
[2]Using 2 M methylamine in THF.

Example 31

1-(2,6-difluorophenyl)-5-(4-fluoro-2-methylphenyl)-7-methylsulfinyl-3,4-dihydro-1H-pyrimido[4,5-d]pyrimidin-2-one The product of example 2 (204 mg, 0.49 mmol) in THF was treated dropwise with Oxone® (0.307 g, 0.5 mmol) in $H_2O$ (10 mL). The mixture was stirred at 23° for 2 h, diluted with EtOAc (100 mL) and washed with $H_2O$ (2×25 mL) and satd aq NaCl (25 mL), dried ($Na_2SO_4$), and concentrated. The residue was purified by prep hplc to afford the sulfoxide as a white powder. LC MS m/z=433 (MH$^+$), Rt=1.70 min

Example 32

1-(2,6-difluorophenyl)-5-(4-fluoro-2-methylphenyl)-7-(1-methyl-1H-imidazol-2-yl-3,4-dihydro-1H-pyrimido[4,5-d]pyrimidin-2-one trifluoroacetate N-Methylimidazole (82 uL, 1.0 mmol) in dry THF was cooled to −70° and n-butyl lithium (2.5 M in hexane) (0.36 mL, 0.9 mmol) was added, the mixture was stirred 15 min and then the product of example 3 (45 mg, 0.1 mmol) was added and the reaction was warmed to 23°, and stirred 30 min. The reaction was poured into satd aq $NaHCO_3$ (20 mL) and stirred 5 min and then extracted with EtOAc (2×). The combined EtOAc was washed with $H_2O$ (3×), satd aq NaCl, dried ($Na_2SO_4$) and concentrated. The residue was purified by prep hplc to afford 11.6 mg (26%) of the title compound as a white powder. LC MS m/z=451 (MH$^+$), Rt=1.55 min.

Example 33

1-(2,6-difluorophenyl)-5-(4-fluoro-2-methylphenyl)-7-(1-piperazin-4-yl)-3,4-dihydro-1H-pyrimido[4,5-d]pyrimidin-2-one The title compound was prepared by the method of example 4 except that 1-BOC-piperazine (Fluka) was the amine. TFA deblocking of the intermediate BOC protected compound as in example 4 and prep hplc afforded the title compound as a white powder. LC MS m/z=455 (MH$^+$), Rt=1.55 min.

Example 34

1-(2,6-difluorophenyl)-5-(4-fluoro-2-methylphenyl)-7-(4-carboxypiperidin-1-yl)-3,4-dihydro-1H-pyrimido[4,5-d]pyrimidin-2-one The product of example 11 (56 mg, 0.11 mmol) was dissolved in THF (2 mL) and LiOH (24 mg, 1.0 mmol) in $H_2O$ (1.0 mL) was added, and the resulting soln was stirred for 4 h. The reaction was concentrated and redissolved in DMSO and purified by prep hplc to afford 24.8 mg (45%) of the title compound. LC MS m/z=498 (MH$^+$), Rt=1.64 min.

The sulfides in examples 35 to 37 (Table 2) were prepared by the method of Example 2, except that the boronic acid in step 2b was varied as depicted in Table 2. below.

TABLE 2

| Example | Compound name | Boronic acid | LC MS m/z | Rt (min) |
|---|---|---|---|---|
| 35 | 1-(2,6-Difluorophenyl)-5-phenyl-7-methyl-sulfanyl-3,4-dihydro-1H-pyrimido[4,5-d]pyrimidin-2-one | 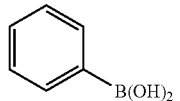 | 385 | 2.19 |

TABLE 2-continued

| Example | Compound name | Boronic acid | LC MS m/z | Rt (min) |
|---|---|---|---|---|
| 36 | 1-(2,6-Difluorophenyl)-5-(4-fluorophenyl)-7-methylsulfanyl-3,4-dihydro-1H-pyrimido[4,5-d]pyrimidin-2-one | 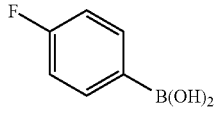 | 403 | 2.19 |
| 37 | 1-(2,6-difluorophenyl)-5-(2-methylphenyl)-7-methylsulfanyl-3,4-dihydro-1H-pyrimido[4,5-d]pyrimidin-2-one | 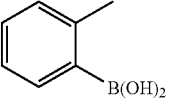 | 399 | 2.20 |

The sulfides in examples 38-44 (Table 3) were prepared by the method of Example 2 except that the amine in step 2a was varied as depicted in Table 3, below.

TABLE 3

| Example | Compound Name | Amine | LC MS m/z | Rt (min) |
|---|---|---|---|---|
| 38 | 1-((R)-1-Phenylethyl-5-(2-methyl-4-fluoro)phenyl-7-methylsulfanyl-3,4-dihydro-1H-pyrimido[4,5-d]pyrimidin-2-one | R-α-methyl-benzylamine | 409 | 2.39 |
| 39 | 1-((S)-1-Phenylethyl-5-(2-methyl-4-fluoro)phenyl-7-methylsulfanyl-3,4-dihydro-1H-pyrimido[4,5-d]pyrimidin-2-one | S-α-methyl-benzylamine | 409 | 2.39 |
| 40 | 1-(2-Chlorophenyl)-5-(2-methyl-4-fluoro)phenyl-7-methylsulfanyl-3,4-dihydro-1H-pyrimido[4,5-d]pyrimidin-2-one | 2-chloroaniline | 415 | 2.17 |
| 41 | 1-Cyclohexyl-5-(2-methyl-4-fluoro)phenyl-7-methylsulfanyl-3,4-dihydro-1H-pyrimido[4,5-d]pyrimidin-2-one | cyclohexyl-amine | 387 | 2.62 |
| 42 | 1-(2-Methylphenyl)-5-(2-methyl-4-fluoro)phenyl-7-methylsulfanyl-3,4-dihydro-1H-pyrimido[4,5-d]pyrimidin-2-one | 2-methylaniline | 395 | 2.20 |
| 43 | 1-(2,6-Dimethylphenyl)-5-(2-methyl-4-fluoro)phenyl-7-methylsulfanyl-3,4-dihydro-1H-pyrimido[4,5-d]pyrimidin-2-one | 2,6-di-methylaniline | 409 | 2.22 |
| 44 | 1-(2-Fluorophenyl)-5-(2-methyl-4-fluoro)phenyl-7-methylsulfanyl-3,4-dihydro-1H-pyrimido[4,5-d]pyrimidin-2-one | 2-fluoroaniline | 399 | 2.10 |

The sulfones in Table 4 were made by the procedure of Example 3 except that the substrate sulfides were the products of the examples indicated.

TABLE 4

| Example | Compound name | Method* | LC MS m/z | Rt (min) |
|---|---|---|---|---|
| 45 | 1-(2,6-Difluorophenyl)-5-phenyl-7-methylsulfonyl-3,4-dihydro-1H-pyrimido[4,5-d]pyrimidin-2-one | 35 | 417 | 1.75 |
| 46 | 1-(2,6-Difluorophenyl)-5-(4-fluorophenyl)-7-methylsulfonyl-3,4-dihydro-1H-pyrimido[4,5-d]pyrimidin-2-one | 36 | 436 | 1.82 |

TABLE 4-continued

| Example | Compound name | Method* | LC MS m/z | Rt (min) |
|---|---|---|---|---|
| 47 | 1-(2,6-Difluorophenyl)-5-(2-methylphenyl)-7-methylsulfonyl-3,4-dihydro-1H-pyrimido[4,5-d]pyrimidin-2-one | 37 | 431 | 1.87 |
| 48 | 1-((R))-1-Phenylethyl)-5-(2-methyl-4-fluoro)phenyl-7-methylsulfonyl-3,4-dihydro-1H-pyrimido[4,5-d]pyrimidin-2-one | 38 | 441 | 2.01 |
| 49 | 1-((S)-1-Phenylethyl)-5-(2-methyl-4-fluoro)phenyl-7-methylsulfonyl-3,4-dihydro-1H-pyrimido[4,5-d]pyrimidin-2-one | 39 | 441 | 2.01 |
| 50 | 1-(2-Chlorophenyl)-5-(2-methyl-4-fluoro)phenyl-7-methylsulfonyl-3,4-dihydro-1H-pyrimido[4,5-d]pyrimidin-2-one | 40 | 447 | 1.94 |
| 51 | 1-Cyclohexyl-5-(2-methyl-4-fluoro)phenyl-7-methylsulfonyl-3,4-dihydro-1H-pyrimido[4,5-d]pyrimidin-2-one | 41 | 419 | 2.02 |
| 52 | 1-(2-Methylphenyl)-5-(2-methyl-4-fluoro)phenyl-7-methylsulfonyl-3,4-dihydro-1H-pyrimido[4,5-d]pyrimidin-2-one | 42 | 427 | 1.82 |
| 53 | 1-(2,6-Dimethylphenyl)-5-(2-methyl-4-fluoro)phenyl-7-methylsulfonyl-3,4-dihydro-1H-pyrimido[4,5-d]pyrimidin-2-one | 43 | 441 | 1.92 |
| 54 | 1-(2-Fluorophenyl)-5-(2-methyl-4-fluoro)phenyl-7-methylsulfonyl-3,4-dihydro-1H-pyrimido[4,5-d]pyrimidin-2-one | 44 | 431 | 1.84 |

*the substrate is the product of the noted example #

Example 55

1-(2,6-Difluorophenyl)-5-phenyl-7-(4-methylpiperazin-1-yl)-3,4-dihydro-1H-pyrimido[4,5-d]pyrimidin-2-one The product of example 45 (41.6 mg, 0.1 mmol), 4-methylpiperazine (30 mg, 0.3 mmol) and NMP (1.0 mL) were dissolved together and heated to 65° for 18 h. The NMP was removed in high vacuum and the residue was purified by prep hplc to afford 17 mg of the title compound. LC MS m/z=437 (MH$^+$), Rt=1.47 min.

Example 56

1-(2,6-Difluorophenyl)-5-phenyl-7-piperazin-1-yl-3,4-dihydro-1H-pyrimido[4,5-d]pyrimidin-2-one The product of example 45 (41.6 mg, 0.1 mmol), and 1-BOC-piperazine (Fluka) were treated by the method of example 55, omitting the hplc step, to afford the BOC protected intermediate. This product was deblocked by the procedure of example 4b and purified by prep hplc to afford the title compound. LC MS m/z=422 (MH$^+$), Rt=1.37 min.

The compounds in Table 5 were prepared by either the method of Example 5, using the appropriate amine and the sulfone shown in Table 5 (Method C; includes aqueous work-up), or the method of Example 55 using the appropriate amine and the sulfone shown in Table 5 (Method D; with concentration of the crude reaction mixture, then preparation hplc), or the method of Example 33 using the appropriate sulfone (Method E; aq. work-up with citric acid, deblocking, and prep hplc) or the method of Example 56 using the appropriate sulfone as shown in Table 5 (Method F; concentration, deblocking, and prep hplc). In the table, method* is the substrate is the sulfone of the noted example.

TABLE 5

| Example | Compound name | Method* | LC MS m/z | Rt |
|---|---|---|---|---|
| 57 | 1-(2,6-difluorophenyl)-5-(2-methylphenyl)-7-(2-diethylaminoethylamino)-3,4-dihydro-1H-pyrimido[4,5-d]pyrimidin-2-one trifluoroacetate | C (47) | 467 | 1.44 |
| 58 | 1-(2,6-difluorophenyl)-5-(2-methylphenyl)-7-(1-piperazin-4-yl)-3,4-dihydro-1H-pyrimido[4,5-d]pyrimidin-2-one | E (47) | 437 | 1.50 |
| 59 | 1-(2,6-diflurorophenyl)-5-phenyl-7-(2-hydroxyethyl)methylamino-3,4-dihydro-1H-pyrimido[4,5-d]pyrimidin-2-one | D (45) | 412 | 1.60 |
| 60 | 1-(2,6-diflurorophenyl)-5-phenyl-7-(4-carboethoxypiperidin-1-yl)-3,4-dihydro-1H-pyrimido[4,5-d]pyrimidin-2-one | D (45) | 494 | 1.85 |
| 61 | 1-(2,6-diflurorophenyl)-5-phenyl-7-(4-hydroxypiperidin-1-yl)-3,4-dihydro-1H-pyrimido[4,5-d]pyrimidin-2-one | D (45) | 438 | 1.74 |

TABLE 5-continued

| Example | Compound name | Method* | LC MS m/z | Rt |
|---|---|---|---|---|
| 62 | 1-(2,6-diflurorophenyl)-5-phenyl-7-(imidazol-1-yl)-3,4-dihydro-1H-pyrimido[4,5-d]pyrimidin-2-one | D (45) | 405 | 1.47 |
| 63 | 1-(2,6-diflurorophenyl)-5-phenyl-7-(morpholin-1-yl)-3,4-dihydro-1H-pyrimido[4,5-d]pyrimidin-2-one | D (45) | 424 | 2.04 |
| 64 | 1-(2,6-Difluorophenyl)-5-(4-fluorophenyl-7-(4-methylpiperazin-1-yl)-3,4-dihydro-1H-pyrimido[4,5-d]pyrimidin-2-one | D (46) | 455 | 1.47 |
| 65 | 1-(2,6-diflurorophenyl)-5-(4-fluorophenyl)-7-(2-hydroxyethyl)methylamino-3,4-dihydro-1H-pyrimido[4,5-d]pyrimidin-2-one | D (46) | 430 | 1.72 |
| 66 | 1-(2,6-difluorophenyl)-5-(4-fluorophenyl)-7-(piperazin-1-yl)-3,4-dihydro-1H-pyrimido[4,5-d]pyrimidin-2-one | F (46) | 441 | 1.40 |
| 67 | 1-(2,6-difluorophenyl)-5-(4-fluorophenyl)-7-(4-carboethoxypiperidin-1-yl)-3,4-dihydro-1H-pyrimido[4,5-d]pyrimidin-2-one | D (46) | 512 | 2.42 |
| 68 | 1-(2,6-diflurorophenyl)-5-(4-fluorophenyl)-7-(4-hydroxypiperidin-1-yl)-3,4-dihydro-1H-pyrimido[4,5-d]pyrimidin-2-one | D (46) | 456 | 1.95 |
| 69 | 1-(2,6-diflurorophenyl)-5-(4-fluorophenyl)-7-(imidazol-1-yl)-3,4-dihydro-1H-pyrimido[4,5-d]pyrimidin-2-one | D (46) | 423 | 1.52 |
| 70 | 1-(2,6-diflurorophenyl)-5-(4-fluorophenyl)-7-(morpholin-1-yl)-3,4-dihydro-1H-pyrimido[4,5-d]pyrimidin-2-one | D (46) | 442 | 2.10 |
| 71 | 1-(2,6-diflurorophenyl)-5-(4-fluorophenyl)-7-(4-hydroxymethylpiperidin-1-yl)-3,4-dihydro-1H-pyrimido[4,5-d]pyrimidin-2-one | D (46) | 470 | 1.90 |

Example 72

1-(2,6-difluorophenyl)-5-phenyl-7-(1-methyl-1H-imidazol-2-yl-3,4-dihydro-1H-pyrimido[4,5-d]pyrimidin-2-one trifluoroacetate The product of example 45 was converted to the target compound by the procedure of example 32. LC MS m/z=419 (MH+), Rt=1.42 min Example 73

1-(2,6-difluorophenyl)-5-(4-fluorophenyl)-7-(1-methyl-1H-imidazol-2-y)1-3,4-dihydro-1H-pyrimido[4,5-d]pyrimidin-2-one trifluoroacetate The product of example 46 was converted to the target compound by the procedure of example 32. LC MS m/z=437, (MH+), Rt=1.44 min.

Example 74

1-(2,6-difluorophenyl)-5-phenyl-7-(4-carboxypiperidin-1-yl)-3,4-dihydro-1H-pyrimido[4,5-d]pyrimidin-2-one trifluoroacetate The product of example 60 was converted to the target compound by the procedure of example 34. LC MS m/z=466 (MH+), Rt=2.39 min Example 75

1-(2,6-difluorophenyl)-5-(4-fluorophenyl)-7-(4-carboxypiperidin-1-yl)-3,4-dihydro-1H-pyrimido[4,5-d]pyrimidin-2-one trifluoroacetate The product of example 67 was converted to the target compound by the procedure of example 34. LC MS m/z=484 (MH+), Rt=1.95 min Example 76

1-(2-Chlorophenyl)-5-(4-fluoro-2-methylphenyl)-7-(2-pyrrolidin-1-yl-ethylamino)-3,4-dihydro-1H-pyrimidido[4,5-d]pyrimidin-2-one The product of example 50 (75 mg, 0.168 mmol), pyrrolidin-1-yl ethylamine (57 mg, 0.5 mmol) were combined in a sealed tube at 90° for 20 h. Concentration and prep hplc afforded the title compound as an amber oil. LC MS m/z=480 (MH+), Rt=1.52 min Example 77

1-(2-Chlorophenyl)-5-(4-fluoro-2-methylphenyl)-7-(1H-tetrazol-5-ylamino)-3,4-dihydro-1H-pyrimido[4,5-d]pyrimidin-one The method of example 76 was repeated except using 5-aminotetrazole as the amine and the reaction was heated to 150° for 10 h. Concentration and prep hplc afforded the title compound as an amber oil. LC MS m/z=450 (MH+), Rt=1.94 min.

The compounds in Table 6 were prepared by either the method of Example 76 (method G) or the method of Example 77 (method H) using the appropriate amine and the sulphone of the example indicated.

TABLE 6

| Example | Compound name | Method* | LC MS m/z | Rt min |
|---|---|---|---|---|
| 78 | 1-(2-Chlorophenyl)-5-(4-fluoro-2-methylphenyl)-7-(2-piperidin-1-ylethylamino)-3,4-dihydro-1H-pyrimido[4,5-d]pyrimidin-one | (50) G | 495 | 1.63 |
| 79 | 1-(2-Chlorophenyl)-5-(4-fluoro-2-methylphenyl)-7-(2-hydroxy-1-hydroxymethyl-1-methylethylamino)-3,4-dihydro-1H-pyrimido[4,5-d]pyrimidin-one | (50) H | 472 | 1.45 |
| 80 | 1-(2-Chlorophenyl)-5-(4-fluoro-2-methylphenyl)-7-((R)-2-hydroxy-1-methylethylamino)-3,4-dihydro-1H-pyrimido[4,5-d]pyrimidin-one | (50) G | 442 | 1.62 |
| 81 | 1-(2-Chlorophenyl)-5-(4-fluoro-2-methylphenyl)-7-((S)-2-hydroxy-1-methylethylamino)-3,4-dihydro-1H-pyrimido[4,5-d]pyrimidin-one | (50) G | 442 | 1.60 |
| 82 | 1-(2-Chlorophenyl)-5-(4-fluoro-2-methylphenyl)-7-(2-hydroxy-1,1-bis-hydroxymethyl-ethylamino)-3,4-dihydro-1H-pyrimido[4,5-d]pyrimidin-one | (50) H | 488 | 1.31 |
| 83 | 1-(2-Chlorophenyl)-5-(4-fluoro-2-methylphenyl)-7-(2-hydroxy-1,1-dimethyl-ethylamino)-3,4-dihydro-1H-pyrimido[4,5-d]pyrimidin-one | (50) H | 447 | 2.26 |
| 84 | 1-(2-Chlorophenyl)-5-(4-fluoro-2-methylphenyl)-7-[(2-hydroxyethy)-methylamino]-3,4-dihydro-1H-pyrimido[4,5-d]pyrimidin-one | (50) G | 442 | 1.75 |
| 85 | 1-(2-Chlorophenyl)-5-(4-fluoro-2-methylphenyl)-7-[(racemic)-3-exo-(bicyclo[2.2.1]hept-ene-2-carboxylic acid amide)amino]-3,4-dihydro-1H-pyrimido[4,5-d]pyrimidin-one | (50) H | 519 | 1.87 |
| 86 | 1-(2-Chlorophenyl)-5-(4-fluoro-2-methylphenyl)-7-[(racemic)-3-endo-(bicyclo[2.2.1]hept-ene-2-carboxylic acid amide)amino]-3,4-dihydro-1H-pyrimido[4,5-d]pyrimidin-one | (50) G | 519 | 1.80 |
| 87 | 1-(2-Chlorophenyl)-5-(4-fluoro-2-methylphenyl)-7-{([1,3]dioxolan-2-ylmethyl)-amino}-3,4-dihydro-1H-pyrimido[4,5-d]pyrimidin-one | (50) G | 470 | 1.77 |
| 88 | 1-(2-Chlorophenyl)-5-(4-fluoro-2-methylphenyl)-7-[3-(2-oxo-pyrrolidin-1-yl) propylamino]-3,4-dihydro-1H-pyrimido[4,5-d]pyrimidin-one | (50) G | 509 | 1.69 |
| 89 | 1-(2-Chlorophenyl)-5-(4-fluoro-2-methylphenyl)-7-(2-hydroxyethylamino)-3,4-dihydro-1H-pyrimido[4,5-d]pyrimidin-one | (50) G | 427 | 1.53 |
| 90 | 1-((S)-1-Phenylethyl)-5-(4-fluoro-2-methylphenyl)-7-(2-pyrrolidin-1-yl-ethylamino)-3,4-dihydro-1H-pyrimido[4,5-d]pyrimidin-one | (49) G | 475 | 1.59 |
| 91 | 1-((S)-1-Phenylethyl)-5-(4-fluoro-2-methylphenyl)-7-(2-piperidin-1-yl ethylamino)-3,4-dihydro-1H-pyrimido[4,5-d]pyrimidin-one | (49) G | 489 | 1.65 |
| 92 | 1-((S)-1-Phenylethyl)-5-(4-fluoro-2-methylphenyl)-7-(1H-tetrazol-5-ylamino)-3,4-dihydro-1H-pyrimido[4,5-d]pyrimidin-one | (49) H | 446 | 2.10 |
| 93 | 1-((S)-1-Phenylethyl)-5-(4-fluoro-2-methylphenyl)-7-((R)-2-hydroxy-1-methyl-ethylamino)-3,4-dihydro-1H-pyrimido[4,5-d]pyrimidin-one | (49) G | 436 | 1.69 |
| 94 | 1-((S)-1-Phenylethyl)-5-(4-fluoro-2-methylphenyl)-7-[(2-hydroxyethyl)-methylamino]-3,4-dihydro-1H-pyrimido[4,5-d]pyrimidin-one | (49) G | 436 | 1.79 |
| 95 | 1-((S)-1-Phenylethyl)-5-(4-fluoro-2-methylphenyl)-7-[([1,3]dioxolan-2-ylmethyl)amino]-3,4-dihydro-1H-pyrimido[4,5-d]pyrimidin-one | (49) G | 464 | 1.85 |
| 96 | 1-((S)-1-Phenylethyl)-5-(4-fluoro-2-methylphenyl)-7-[3-(2-oxo-pyrrolidin-1-yl)-propylamino]-3,4-dihydro-1H-pyrimido[4,5-d]pyrimidin-one | (49) G | 503 | 1.80 |
| 97 | 1-((S)-1-Phenylethyl)-5-(4-fluoro-2-methylphenyl)-7-(2-hydroxyethylamino)-3,4-dihydro-1H-pyrimido[4,5-d]pyrimidin-one | (49) G | 422 | 1.63 |
| 98 | 1-((S)-1-Phenylethyl)-5-(4-fluoro-2-methylphenyl)-7-(3-pyrrolidin-1-ylpropylamino)-3,4-dihydro-1H-pyrimido[4,5-d]pyrimidin-one | (49) G | 489 | 1.47 |
| 99 | 1-Cyclohexyl-5-(4-fluoro-2-methylphenyl)-7-(2-pyrrolidin-1-yl-ethylamino)-3,4-dihydro-1H-pyrimido[4,5-d]pyrimidin-one | (51) G | 453 | 1.55 |
| 100 | 1-Cyclohexyl-5-(4-fluoro-2-methylphenyl)-7-(2-piperidin-1-yl ethylamino)-3,4-dihydro-1H-pyrimido[4,5-d]pyrimidin-one | (51) G | 467 | 1.72 |

TABLE 6-continued

| Example | Compound name | Method* | LC MS m/z | Rt min |
|---|---|---|---|---|
| 101 | 1-Cyclohexyl-5-(4-fluoro-2-methylphenyl)-7-(1H-tetrazol-5-ylamino)-3,4-dihydro-1H-pyrimido[4,5-d]pyrimidin-one | (51) H | 424 | 2.17 |
| 102 | 1-Cyclohexyl-5-(4-fluoro-2-methylphenyl)-7-(2-hydroxy-1-hydroxymethyl-1-methylethylamino)-3,4-dihydro-1H-pyrimido[4,5-d]pyrimidin-one | (51) G | 444 | 1.66 |
| 103 | 1-Cyclohexyl-5-(4-fluoro-2-methylphenyl)-7-((R)-2-hydroxy-1-methyl-ethylamino)-3,4-dihydro-1H-pyrimido[4,5-d]pyrimidin-one | (51) G | 414 | 1.68 |
| 104 | 1-Cyclohexyl-5-(4-fluoro-2-methylphenyl)-7-((S)-2-hydroxy-1-methylethylamino)-3,4-dihydro-1H-pyrimido[4,5-d]pyrimidin-one | (51) G | 428 | 2.06 |
| 105 | 1-Cyclohexyl-5-(4-fluoro-2-methylphenyl)-7-(2-hydroxy-1,1-bis-hydroxymethyl-ethylamino)-3,4-dihydro-1H-pyrimido[4,5-d]pyrimidin-one | (51) H | 460 | 1.52 |
| 106 | 1-Cyclohexyl-5-(4-fluoro-2-methylphenyl)-7-(2-hydroxy-1,1-dimethyl-ethylamino)-3,4-dihydro-1H-pyrimido[4,5-d]pyrimidin-one | (51) G | 428 | 1.85 |
| 107 | 1-Cyclohexyl-5-(4-fluoro-2-methylphenyl)-7-[([1,3]dioxolan-2-ylmethyl)amino]-3,4-dihydro-1H-pyrimido[4,5-d]pyrimidin-one | (51) G | 442 | 1.84 |
| 108 | 1-Cyclohexyl-5-(4-fluoro-2-methylphenyl)-7-[3-(2-oxo-pyrrolidin-1-yl)-propylamino]-3,4-dihydro-1H-pyrimido[4,5-d]pyrimidin-one | (51) G | 481 | 1.72 |
| 109 | 1-Cyclohexyl-5-(4-fluoro-2-methylphenyl)-7-(2-hydroxyethylamino)-3,4-dihydro-1H-pyrimido[4,5-d]pyrimidin-one | (51) G | 400 | 1.59 |
| 110 | 1-Cyclohexyl-5-(4-fluoro-2-methylphenyl)-7-(3-pyrrolidin-1-ylpropylamino)-3,4-dihydro-1H-pyrimido[4,5-d]pyrimidin-one | (51) G | 467 | 1.47 |
| 111 | 1-(2-Methylphenyl)-5-(4-fluoro-2-methylphenyl)-7-(2-pyrrolidin-1-yl-ethylamino)-3,4-dihydro-1H-pyrimido[4,5-d]pyrimidin-one | (52) G | 461 | 1.42 |
| 112 | 1-(2-Methylphenyl)-5-(4-fluoro-2-methylphenyl)-7-(2-piperidin-1-yl ethylamino)-3,4-dihydro-1H-pyrimido[4,5-d]pyrimidin-one | (52) G | 475 | 1.49 |
| 113 | 1-(2-Methylphenyl)-5-(4-fluoro-2-methylphenyl)-7-(2-hydroxy-1-hydroxymethyl-1-methyl ethylamino)-3,4-dihydro-1H-pyrimido[4,5-d]pyrimidin-one | (52) G | 452 | 1.41 |
| 114 | 1-(2-Methylphenyl)-5-(4-fluoro-2-methylphenyl)-7-((R)-2-hydroxy-1-methyl-ethylamino)-3,4-dihydro-1H-pyrimido[4,5-d]pyrimidin-one | (52) G | 421 | 1.53 |
| 115 | 1-(2-Methylphenyl)-5-(4-fluoro-2-methylphenyl)-7-((S)-2-hydroxy-1-methylethylamino)-3,4-dihydro-1H-pyrimido[4,5-d]pyrimidin-one | (52) G | 422 | 1.54 |
| 116 | 1-(2-Methylphenyl)-5-(4-fluoro-2-methylphenyl)-7-(2-hydroxy-1,1-bis-hydroxymethyl-ethylamino)-3,4-dihydro-1H-pyrimido[4,5-d]pyrimidin-one | (52) H | 468 | 1.30 |
| 117 | -(2-Methylphenyl)-5-(4-fluoro-2-methylphenyl)-7-(2-hydroxy-1,1-dimethyl-ethylamino)-3,4-dihydro-1H-pyrimido[4,5-d]pyrimidin-one | (52) G | 436 | 1.60 |
| 118 | 1-(2-Methylphenyl)-5-(4-fluoro-2-methylphenyl)-7-[(2-hydroxyethyl)-methylamino]-3,4-dihydro-1H-pyrimido[4,5-d]pyrimidin-one | (52) G | 422 | 1.66 |
| 119 | 1-(2-Methylphenyl)-5-(4-fluoro-2-methylphenyl)-7-[([1,3]dioxolan-2-ylmethyl)amino]-3,4-dihydro-1H-pyrimido[4,5-d]pyrimidin-one | (52) G | 450 | 1.70 |
| 120 | 1-(2-Methylphenyl)-5-(4-fluoro-2-methylphenyl)-7-[3-(2-oxo-pyrrolidin-1-yl)-propylamino]-3,4-dihydro-1H-pyrimido[4,5-d]pyrimidin-one | (52) G | 489 | 1.60 |
| 121 | 1-(2-Methylphenyl)-5-(4-fluoro-2-methylphenyl)-7-(2-hydroxyethylamino)-3,4-dihydro-1H-pyrimido[4,5-d]pyrimidin-one | (52) G | 408 | 1.42 |
| 122 | 1-(2,6-Dimethylphenyl)-5-(4-fluoro-2-methylphenyl)-7-(2-pyrrolidin-1-yl-ethylamino)-3,4-dihydro-1H-pyrimido[4,5-d]pyrimidin-one | (53) G | 475 | 1.48 |
| 123 | 1-(2,6-Dimethylphenyl)-5-(4-fluoro-2-methylphenyl)-7-(2-piperidin-1-yl ethylamino)-3,4-dihydro-1H-pyrimido[4,5-d]pyrimidin-one | (53) G | 489 | 1.55 |
| 124 | 1-(2,6-Dimethylphenyl)-5-(4-fluoro-2-methylphenyl)-7-(1H-tetrazol-5-ylamino)-3,4-dihydro-1H-pyrimido[4,5-d]pyrimidin-one | (53) H | 446 | 1.95 |

TABLE 6-continued

| Example | Compound name | Method* | LC MS m/z | Rt min |
|---|---|---|---|---|
| 125 | 1-(2,6-Dimthylphenyl)-5-(4-fluoro-2-methylphenyl)-7-(2-hydroxy-1-hydroxymethyl-1-methyl ethylamino)-3,4-dihydro-1H-pyrimido[4,5-d]pyrimidin-one | (53) H | 466 | 1.49 |
| 126 | 1-(2,6-Dimethylphenyl)-5-(4-fluoro-2-methylphenyl)-7-((R)-2-hydroxy-1-methyl-ethylamino)-3,4-dihydro-1H-pyrimido[4,5-d]pyrimidin-one | (53) G | 436 | 1.58 |
| 127 | 1-(2,6-Dimethylphenyl)-5-(4-fluoro-2-methylphenyl)-7-((S)-2-hydroxy-1-methylethylamino)-3,4-dihydro-1H-pyrimido[4,5-d]pyrimidin-one | (53) G | 436 | 1.60 |
| 128 | 1-(2,6-Dimethylphenyl)-5-(4-fluoro-2-methylphenyl)-7-(2-hydroxy-1,1-bis-hydroxymethyl-ethylamino)-3,4-dihydro-1H-pyrimido[4,5-d]pyrimidin-one | (53) H | 482 | 1.36 |
| 129 | -(2,6-Dimethylphenyl)-5-(4-fluoro-2-methylphenyl)-7-(2-hydroxy-1,1-dimethyl-ethylamino)-3,4-dihydro-1H-pyrimido[4,5-d]pyrimidin-one | (53) G | 450 | 1.70 |
| 130 | 1-(2,6-Dimethylphenyl)-5-(4-fluoro-2-methylphenyl)-7-[(2-hydroxyethyl)-methylamino]-3,4-dihydro-1H-pyrimido[4,5-d]pyrimidin-one | (53) G | 436 | 1.72 |
| 131 | 1-(2,6-Dimethylphenyl)-5-(4-fluoro-2-methylphenyl)-7-[([1,3]dioxolan-2-ylmethyl)amino]-3,4-dihydro-1H-pyrimido[4,5-d]pyrimidin-one | (53) G | 464 | 1.77 |
| 132 | 1-(2,6-Dimethylphenyl)-5-(4-fluoro-2-methylphenyl)-7-[3-(2-oxo-pyrrolidin-1-yl)-propylamino]-3,4-dihydro-1H-pyrimido[4,5-d]pyrimidin-one | (53) G | 503 | 1.68 |
| 133 | 1-(2,6-Dimethylphenyl)-5-(4-fluoro-2-methylphenyl)-7-piperazin-1-yl-3,4-dihydro-1H-pyrimido[4,5-d]pyrimidin-one | (53) G$^a$ | 447 | 2.76 |
| 134 | 1-(2,6-Dimethylphenyl)-5-(4-fluoro-2-methylphenyl)-7-(2-hydroxyethylamino)-3,4-dihydro-1H-pyrimido[4,5-d]pyrimidin-one | (53) G | 422 | 1.51 |
| 135 | 1-(2,6-Dimethylphenyl)-5-(4-fluoro-2-methylphenyl)-7-(3-pyrrolidin-1-ylpropylamino)-3,4-dihydro-1H-pyrimido[4,5-d]pyrimidin-one | (53) G | 489 | 1.44 |
| 136 | 1-(2-Fluorophenyl)-5-(4-fluoro-2-methylphenyl)-7-(2-pyrrolidin-1-yl-ethylamino)-3,4-dihydro-1H-pyrimido[4,5-d]pyrimidin-one | (54) G | 465 | 1.49 |
| 137 | 1-(2-Fluorophenyl)-5-(4-fluoro-2-methylphenyl)-7-(2-piperidin-1-yl ethylamino)-3,4-dihydro-1H-pyrimido[4,5-d]pyrimidin-one | (54) G | 479 | 1.53 |
| 138 | 1-(2-Fluorophenyl)-5-(4-fluoro-2-methylphenyl)-7-(2-hydroxy-1-hydroxymethyl-1-methyl ethylamino)-3,4-dihydro-1H-pyrimido[4,5-d]pyrimidin-one | (54) H | 456 | 1.45 |
| 139 | 1-(2-Fluorophenyl)-5-(4-fluoro-2-methylphenyl)-7-((R)-2-hydroxy-1-methyl-ethylamino)-3,4-dihydro-1H-pyrimido[4,5-d]pyrimidin-one | (54) G | 426 | 1.54 |
| 140 | 1-(2-Fluorophenyl)-5-(4-fluoro-2-methylphenyl)-7-((S)-2-hydroxy-1-methylethylamino)-3,4-dihydro-1H-pyrimido[4,5-d]pyrimidin-one | (54) G | 440 | 1.78 |
| 141 | 1-(2-Fluorophenyl)-5-(4-fluoro-2-methylphenyl)-7-(2-hydroxy-1,1-bis-hydroxymethyl-ethylamino)-3,4-dihydro-1H-pyrimido[4,5-d]pyrimidin-one | (54) H | 472 | 1.34 |
| 142 | 1-(2-Fluorophenyl)-5-(4-fluoro-2-methylphenyl)-7-(2-hydroxy-1,1-dimethyl-ethylamino)-3,4-dihydro-1H-pyrimido[4,5-d]pyrimidin-one | (54) G | 440 | 1.65 |
| 143 | 1-(2-Fluorophenyl)-5-(4-fluoro-2-methylphenyl)-7-[(2-hydroxyethyl)-methylamino]-3,4-dihydro-1H-pyrimido[4,5-d]pyrimidin-one | (54) G | 426 | 1.70 |
| 144 | 1-(2-Fluorophenyl)-5-(4-fluoro-2-methylphenyl)-7-[(racemic)-3-exo-(bicyclo[2.2.1]hept-ene-2-carboxylic acid amide)amino]-3,4-dihydro-1H-pyrimido[4,5-d]pyrimidin-one | (54) H | 503 | 1.82 |

TABLE 6-continued

| Example | Compound name | Method* | LC MS m/z | Rt min |
|---|---|---|---|---|
| 145 | 1-(2-Chlorophenyl)-5-(4-fluoro-2-methylphenyl)-7-[(racemic)-3-endo-(bicyclo[2.2.1]hept-ene-2-carboxylic acid amide)amino]-3,4-dihydro-1H-pyrimido[4,5-d]pyrimidin-one | (54) H | 503 | 1.79 |
| 146 | 1-(2-Fluorophenyl)-5-(4-fluoro-2-methylphenyl)-7-[([1,3]dioxolan-2-ylmethyl)amino]-3,4-dihydro-1H-pyrimido[4,5-d]pyrimidin-one | (54) G | 454 | 1.76 |
| 147 | 1-(2-Fluorophenyl)-5-(4-fluoro-2-methylphenyl)-7-(2-hydroxyethylamino)-3,4-dihydro-1H-pyrimido[4,5-d]pyrimidin-one | (54) G | 412 | 1.46 |

*the sulfone product of the exemplified example number;
aThe reactant amine was 1-Boc-piperazine. The Boc group in this case was removed during the reaction.

Example 148

1-(2-Methylphenyl)-5-(4-fluoro-2-methylphenyl)-7-(1-ethylpiperidin-4-ylamino)-3,4-dihydro-1H-pyrimido[4,5-d]pyrimidin-one The product of example 52 (75 mg, 0.17 mmol), 1-ethylpiperidin-4-ylamine hydrochloride (100 mg, 0.5 mmol), $K_2CO_3$ (83 mg, 0.6 mmol) and NMP (1 mL) were combined and heated to 150° in a sealed tube for 10 h. Concentration and prep hplc afforded the title compound as an amber oil. LC MS m/z=475 (MH+), Rt=1.42 min Example 149

1-(2-Fluorophenyl)-5-(4-fluoro-2-methylphenyl)-7-(1-methylpiperidin-4-ylamino)-3,4-dihydro-1H-pyrimido[4,5-d]pyrimidin-one The product of example 54 (75 mg, 0.17 mmol), 1-methylpiperidin-4-ylamine hydrochloride (94 mg, 0.5 mmol), $K_2CO_3$ (83 mg, 0.6 mmol) and NMP (1 mL) were combined and heated to 90° in a sealed tube for 10 h. Concentration and prep hplc afforded the title compound as an amber oil. LC MS m/z=465 (MH+), Rt=1.49 min.

The products of the examples in Table 7 are made by either the method of example 148 (Method I) or the method of example 149 (Method J) using the sulfone from Table 4 as indicated and the appropriate amine hydrochloride.

TABLE 7

| Example | Compound name | Method* | LC MS m/z | Rt min |
|---|---|---|---|---|
| 150 | 1-(2-Chlorophenyl)-5-(4-fluoro-2-methylphenyl)-7-(1-methylpiperidin-4-ylamino)-3,4-dihydro-1H-pyrimido[4,5-d]pyrimidin-one | (50) J | 481 | 1.44 |
| 151 | 1-(2-Chlorophenyl)-5-(4-fluoro-2-ethylphenyl)-7-(1-methylpiperidin-4-ylamino)-3,4-dihydro-1H-pyrimido[4,5-d]pyrimidin-one | (50) I | 495 | 1.50 |
| 152 | 1-((S)-1-Phenylethyl)-5-(4-fluoro-2-methylphenyl)-7-(1-methylpiperidin-4-ylamino)-3,4-dihydro-1H-pyrimido[4,5-d]pyrimidin-one | (49) J | 475 | 1.48 |
| 153 | 1-((S)-1-Phenylethyl)-5-(4-fluoro-2-methylphenyl)-7-(1-carboxyeth-2-ylamino)-3,4-dihydro-1H-pyrimido[4,5-d]pyrimidin-one | (49) J | 436 | 2.20 |
| 154 | 1-((S)-1-Phenylethyl)-5-(4-fluoro-2-methylphenyl)-7-(1-carboxyeth-2-ylamino)-3,4-dihydro-1H-pyrimido[4,5-d]pyrimidin-one | (49) J | 449 | 1.64 |
| 155 | 1-Cyclohexyl-5-(4-fluoro-2-methylphenyl)-7-(1-methylpiperidin-4-ylamino)-3,4-dihydro-1H-pyrimido[4,5-d]pyrimidin-one | (51) J[a] | 453 | 1.47 |
| 156 | 1-Cyclohexyl-5-(4-fluoro-2-methylphenyl)-7-(1-ethylpiperidin-4-ylamino)-3,4-dihydro-1H-pyrimido[4,5-d]pyrimidin-one | (51) I | 467 | 1.54 |
| 157 | 1-(2-Methylphenyl)-5-(4-fluoro-2-methylphenyl)-7-(1-methylpiperidin-4-ylamino)-3,4-dihydro-1H-pyrimido[4,5-d]pyrimidin-one | (52) J | 461 | 1.37 |
| 158 | 1-(2,6-Dimethylphenyl)-5-(4-fluoro-2-methylphenyl)-7-(1-methylpiperidin-4-ylamino)-3,4-dihydro-1H-pyrimido[4,5-d]pyrimidin-one | (53) J | 475 | 1.42 |
| 159 | 1-(2,6-Dimethylphenyl)-5-(4-fluoro-2-methylphenyl)-7-(1-ethylpiperidin-4-ylamino)-3,4-dihydro-1H-pyrimido[4,5-d]pyrimidin-one | (53) J | 489 | 1.47 |

TABLE 7-continued

| | | | LC MS | |
|---|---|---|---|---|
| Example | Compound name | Method* | m/z | Rt min |
| 160 | 1-(2-Fluorophenyl)-5-(4-fluoro-2-methylphenyl)-7-(1-ethylpiperidin-4-ylamino)-3,4-dihydro-1H-pyrimido[4,5-d]pyrimidin-one | (54) I | 479 | 1.49 |

*the sulfone product of the exemplified example number
<sup>a</sup>The starting amine is glycine tert-butyl ester. The ester is cleaved under the reaction conditions.

Example 161

1-(2,6-Difluorophenyl)-5-(4-fluoro-2-methylphenyl)-7-methoxy-3,4-dihydro-1H-pyrimido[4,5-d]pyrimidin-2-one The product of Example 3 (0.102 g, 0.22 mmol) was suspended in MeOH (2 mL) and stirred under argon. A 1 Molar solution of NaOMe in methanol (0.44 mL, 0.44 mmol) was added. After 10 min the solvent was removed in vacuo, and the residue partitioned between EtOAc and $H_2O$. The organic phase was washed with $H_2O$ (2×), satd aq NaCl (1×), dried over anhydrous $Na_2SO_4$, filtered, and evaporated to give the crude product. Recrystallization from EtOAc/hexane gave the title compound as a white-crystalline solid. mp 210-211° C., LC MS m/z=401 (MH+) Rt=2.0 min.

Example 162

1-(2,6-Difluorophenyl)-5-(4-fluoro-2-methylphenyl)-7-ethoxy-3,4-dihydro-1H-pyrimido[4,5-d]pyrimidin-2-one The product of Example 3 (0.0658 g, 0.147 mmol) was suspended in EtOH (2 mL) and stirred under argon. A 0.5 M solution of NaOEt in EtOH (0.587 mL, 0.294 mmol) was added. After 15 min the solvent was removed in vacuo, and the residue partitioned between EtOAc and $H_2O$. The organic phase was washed with $H_2O$ (2×), satd aq NaCl (1×), dried over anhydrous $Na_2SO_4$, filtered, and evaporated to give the crude product. Flash chromatography on silica gel eluted with 0-5% EtOAc/$CH_2Cl_2$ gave the title compound as a white-amorphous solid. mp 191-194° C., LC MS m/z=415 (MH+) Rt=2.15 min.

Example 163

1-(2,6-Difluorophenyl)-5-(4-fluoro-2-methylphenyl)-7-(2-hydroxyethoxy)-3,4-dihydro-1H-pyrimido[4,5-d]pyrimidin-2-one The product of Example 3 (0.0658 g, 0.147 mmol) was suspended in ethylene glycol (1 mL) and stirred under argon. NaH, dry, 95%, (8.0 mg, 0.32 mmol) was added. After 30 min the solvent was removed in vacuo, and the residue partitioned between EtOAc and $H_2O$. The organic phase was washed with $H_2O$ (2×), satd aq NaCl (1×), dried over anhydrous $Na_2SO_4$, filtered, and evaporated to give the crude product. Flash chromatography on silica gel eluted with 0-10% EtOAc/$CH_2Cl_2$ gave the title compound as a white-amorphous solid. mp 172-175° C., LC MS m/z=431 (MH+) Rt=1.7 min.

Example 164

1-(2,6-Difluorophenyl)-5-(4-fluoro-2-methylphenyl)-7-(1-methylpiperidin-4-yloxy)-3,4-dihydro-1H-pyrimido[4,5-d]pyrimidin-2-one trifluoroacetate A solution of 4-hydroxy-1-methylpiperidine (35.1 mg, 0.3 mmol) in DMSO (0.25 ml) was stirred under argon and NaH, dry, 95%, (7.5 mg, 0.3 mmol) was added. The mixture was stirred for 15 min, and then a solution of the product of Example 3 (0.0672 g, 0.15 mmol) dissolved in DMSO (0.25 mL) was added. After the mixture was stirred for 30 min, the reaction mixture was partitioned between EtOAc and H2O. The organic phase was washed with $H_2O$ (5×), satd aq NaCl (1×), dried over anhydrous $Na_2SO_4$, filtered, and evaporated to give the crude product. Purification by preparative hplc followed by lyophilization gave the title compound as a white-amorphous solid. LC MS m/z=484 (MH+) Rt=1.47 min.

Example 165

1-(2,6-Difluorophenyl)-5-(4-fluoro-2-methylphenyl)-7-[[bis-(2-hydroxyethyl)amino]ethoxy]-3,4-dihydro-1H-pyrimido[4,5-d]pyrimidin-2-one trifluoroacetate NaH, dry, 95%, (8 mg, 0.4 mmol) was added to triethanolamine (243 mg, 1.6 mmol), and then DMSO (0.25 ml) was added. The mixture agitated for 2 min., and then the product of Example 3 (0.0896 g, 0.2 mmol) was added. After 5 min of agitation, additional DMSO (0.25 mL) was added. After the mixture was agitated for 10 min, the reaction mixture was partitioned between EtOAc and H2O The organic phase was washed with $H_2O$ (5×), satd aq NaCl (1×), dried over anhydrous $Na_2SO_4$, filtered, and evaporated to give the crude product. Purification by preparative hplc followed by lyophilization gave the title compound as a white-amorphous solid. LC MS m/z=518 (MH+) Rt=1.25 min.

Example 166

1-(2,6-Difluorophenyl)-5-phenyl-7-methoxy-3,4-dihydro-1H-pyrimido[4,5-d]pyrimidin-2-one Following the procedure of example 161 except using the product of example 45 in place of the product of example 3 gave the title compound as a white-crystalline solid. mp 221-224° C., LC MS m/z=369 (MH+) Rt=1.92 min.

Example 167

1,5-diphenyl-7-methoxy-3,4-dihydro-1H-pyrimido[4,5-d]pyrimidin-2-one a) 1-(2,6-difluorophenyl)-5-phenyl-7-methylsulfonyl-3,4-dihydro-1H-pyrimido[4,5-d]pyrimidin-2-one Following the procedure of example 3 except for using the product of example 1 in place of the product of example 2 gave the title compound as a white solid. LC MS m/z=381 (MH+)Rt=1.78 min.

b) 1,5-diphenyl-7-methoxy-3,4-dihydro-1H-pyrimido[4,5-d]pyrimidin-2-one

Following the procedure of example 161 except using the product of example 167 (a) in place of the product of example 3 gave the title compound as a white-amorphous solid. mp 220-222° C., LC MS m/z=333 (MH+) Rt=1.94 min.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound of the formula:

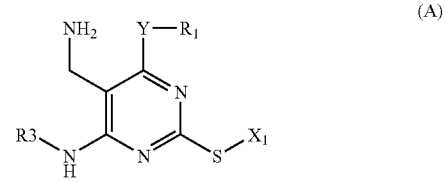

(A)

wherein $X_1$ is a $C_{1-10}$ alkyl, aryl or heteroaryl moiety;

$R_1$ is an optionally substituted aryl or -an optionally substituted heteroaryl ring;

$R_3$ is a $C_{1-10}$ alkyl, $C_{3-7}$ cycloalkyl, $C_{3-7}$cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety; and wherein each of these moieties are optionally substituted; and Y is a bond.

2. The compound according to claim 1 wherein $X_1$ is methyl.

3. The compound according to claim 1 wherein $R_1$ and $R_3$ are each an optionally substituted aryl ring.

4. The compound according to claim 3 wherein $R_1$ and $R_3$ are each an optionally substituted phenyl ring.

5. The compound according to any claim 1 wherein the $R_3$ moiety is optionally substituted one or more times independently with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_n$CN, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C$

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Epidermal Growth Factor Receptor-Derived Peptide

<400> SEQUENCE: 1

Lys Arg Glu Leu Val Glu Pro Leu Thr Pro Ser Gly Glu Ala Pro Asn
1               5                   10                  15

Gln Ala Leu Leu Arg
            20

(=NR$_{10}$)NR$_4$R$_{14}$, (CR$_{10}$R$_{20}$)$_n$OC(Z)NR$_4$R$_{14}$, (CR$_{10}$R$_{20}$)$_n$NR$_{10}$C(Z)NR$_4$R$_{14}$, or (CR$_{10}$R$_{20}$)$_n$NR$_{10}$C(Z)OR$_7$, wherein R$_7$ is C$_{1-6}$alkyl, aryl, arylC$_{1-6}$alkyl, heterocyclic, heterocyclylC$_{1-6}$ alkyl, heteroaryl, or a heteroarylC$_{1-6}$alkyl moiety; and wherein each of these moieties may be optionally substituted;

R$_4$ and R$_{14}$ are each independently selected from hydrogen, optionally substituted C$_{1-4}$ alkyl, optionally substituted aryl or optionally substituted aryl-C$_{1-4}$ alkyl, or R$_4$ and R$_{14}$ together with the nitrogen which they are attached form a heterocyclic ring of 5 to 7 members which ring optionally contains an additional heteroatom selected from oxygen, sulfur or NR$_9$, and which ring is optionally substituted;

Z is oxygen or sulfur;

R$_6$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl; and wherein each of these moieties, excluding hydrogen, may be optionally substituted;

R$_9$ is hydrogen, C(Z)R$_6$, optionally substituted C$_{1-10}$ alkyl, optionally substituted aryl or optionally substituted aryl-C$_{1-4}$ alkyl;

n is 0 or an integer having a value of 1 to 10; and

R$_{10}$ and R$_{20}$ are each independently selected from hydrogen or C$_{1-4}$ alkyl.

6. The compound according to claim 5 wherein R$_3$ is an optionally substituted phenyl ring.

7. The compound according to claim 6 wherein R$_3$ is substituted one or more times, independently with halogen.

8. The compound according to claim 1 wherein R$_3$ is phenyl, cyclohexyl, 2-chlorophenyl, 2,6-dimethylphenyl, 2-fluorophenyl, 2-methylphenyl, or 2,6-difluorophenyl.

9. The compound according to claim 1 wherein R$_1$ is an aryl optionally substituted one to four times, independently, halogen, C$_{1-4}$ alkyl, halo-substituted C$_{1-4}$ alkyl, cyano, nitro, (CR$_{10}$R$_{20}$)$_v$NR$_4$R$_{14}$, (CR$_{10}$R$_{20}$)$_v$C(Z)NR$_4$R$_{14}$, (CR$_{10}$R$_{20}$)$_v$C(Z)OR$_8$, (CR$_{10}$R$_{20}$)$_v$CORa, (CR$_{10}$R$_{20}$)$_v$C(O)H, S(O)mR$_5$, (CR$_{10}$R$_{20}$)$_v$OR$_8$, ZC(Z)R$_{11}$, NR$_{10}$C(Z)R$_{11}$, or NR$_{10}$S(O)$_2$R$_7$, and wherein Ra is C$_{1-4}$alkyl, halo-substituted C$_{1-4}$alkyl, C$_{2-4}$alkenyl, C$_{2-4}$ alkynyl, C$_{3-7}$cycloalkyl, C$_{5-7}$ cycloalkenyl, aryl, aryl C$_{1-4}$ alkyl, heteroaryl, heteroaryl C$_{1-4}$ alkyl, heterocyclyl, heterocyclylC$_{1-4}$ alkyl, (CR$_{10}$R$_{20}$)$_t$OR$_7$, (CR$_{10}$R$_{20}$)$_t$S(O)mR$_7$, (CR$_{10}$R$_{20}$)$_t$NHS(O)$_2$R$_7$, or (CR$_{10}$R$_{20}$)$_t$NR$_4$R$_{14}$, and wherein the alkyl, cycloalkyl, cycloalkenyl, aryl, arylalkyl, heterocyclyl, heterocyclylalkyl, heteroaryl, and heteroarylalkyl moieties are optionally substituted;

R$_5$ is hydrogen, C$_{1-4}$ alkyl, C$_{2-4}$ alkenyl, C$_{2-4}$ alkynyl or NR$_4$R$_{14}$, excluding the moieties SR$_5$ (wherein m is 0) being SNR$_4$R$_{14}$, S(O)$_2$R$_5$ being SO$_2$H (wherein m is 2) and S(O)R$_5$ being SOH, (wherein m is 1);

R$_7$ is C$_{1-6}$alkyl, aryl, arylC$_{1-6}$alkyl, heterocyclic, heterocyclylC$_{1-6}$ alkyl, heteroaryl, or a heteroarylC$_{1-6}$alkyl moiety; and wherein each of these moieties may be optionally substituted;

R$_8$ is hydrogen, C$_{1-4}$ alkyl, halo-substituted C$_{1-4}$ alkyl, C$_{2-4}$alkenyl, C$_{2-4}$ alkynyl, C$_{3-7}$ cycloalkyl, C$_{5-7}$ cycloalkenyl, aryl, arylC$_{1-4}$ alkyl, heteroaryl, heteroarylC$_{1-4}$ alkyl, heterocyclyl, heterocyclylC$_{1-4}$ alkyl, (CR$_{10}$R$_{20}$)$_t$OR$_7$, (CR$_{10}$R$_{20}$)$_t$S(O)$_m$R$_7$, (CR$_{10}$R$_{20}$)$_t$NHS(O)$_2$R$_7$, or (CR$_{10}$R$_{20}$)$_t$NR$_4$R$_{14}$; and wherein the alkyl, cycloalkyl, cycloalkenyl, aryl, arylalkyl, heterocyclyl, heterocyclyl alkyl, heteroaryl, and heteroaryl alkyl moieties, may be optionally substituted;

R$_{10}$ and R$_{20}$ are each independently selected from hydrogen or C$_{1-4}$ alkyl;

R$_{11}$ is C$_{1-4}$ alkyl, halo-substituted C$_{1-4}$ alkyl, C$_{2-4}$ alkenyl, C$_{2-4}$alkynyl, C$_{3-7}$ cycloalkyl, C$_{5-7}$ cycloalkenyl, aryl, arylC$_{1-4}$ alkyl, heteroaryl, heteroarylC$_{1-4}$ alkyl, heterocyclyl, heterocyclylC$_{1-4}$ alkyl, (CR$_{10}$R$_{20}$)$_t$OR$_7$, (CR$_{10}$R$_{20}$)$_t$S(O)$_m$R$_7$, (CR$_{10}$R$_{20}$)$_t$NHS(O)$_2$R$_7$, or (CR$_{10}$R$_{20}$)$_v$NR$_4$R$_{14}$; and wherein the alkyl, cycloalkyl, cycloalkenyl, aryl, arylalkyl, heterocyclyl, heterocyclylalkyl, heteroaryl, and heteroaryl alkyl moieties may be optionally substituted;

t is an integer having a value of 1 to 3; and v is 0 or an integer having a value of 1 or 2.

10. The compound according to claim 9 wherein R$_1$ is an optionally substituted phenyl ring.

11. The compound according to claim 10 wherein X$_1$ is methyl.

12. The compound according to claim 11 wherein R$_3$ is an optionally substituted phenyl ring.

13. The compound according to claim 4 wherein X$_1$ is methyl.

14. The compound according to claim 1 wherein R$_1$ is a phenyl ring substituted by halogen or alkyl.

15. The compound according to claim 1 wherein R$_3$ is 2,6-difluorophenyl.

16. The compound according to claim 1 which is:

(5-Aminomethyl-2-methylsulfanyl-6-phenyl-pyrimidin-4-yl)-phenylamine; or

5-Aminomethyl-6-(4-fluoro-2-methylphenyl)-2-methylsulfanylpyrimidin-4-yl-(2,6-difluorophenyl)amine.

* * * * *